United States Patent
Hyde et al.

(10) Patent No.: US 10,245,393 B2
(45) Date of Patent: Apr. 2, 2019

(54) METHODS, SYSTEMS, AND DEVICES RELATED TO A SUPPLEMENTAL INHALER

(71) Applicant: Elwha LLC, Bellevue, WA (US)

(72) Inventors: Roderick A. Hyde, Redmond, WA (US); Leif T. Stordal, Newcastle, WA (US)

(73) Assignee: Elwha LLC, Bellevue, WA (US)

( * ) Notice: Subject to any disclaimer, the term of this patent is extended or adjusted under 35 U.S.C. 154(b) by 736 days.

(21) Appl. No.: 14/485,460

(22) Filed: Sep. 12, 2014

(65) Prior Publication Data

US 2016/0045685 A1 Feb. 18, 2016

Related U.S. Application Data

(63) Continuation-in-part of application No. 14/459,075, filed on Aug. 13, 2014.

(51) Int. Cl.
*A61M 15/00* (2006.01)
*A61M 16/00* (2006.01)

(52) U.S. Cl.
CPC .... *A61M 15/0021* (2014.02); *A61M 15/0003* (2014.02); *A61M 15/007* (2014.02); *A61M 15/008* (2014.02); *A61M 15/009* (2013.01); *A61M 15/002* (2014.02); *A61M 2016/0027* (2013.01); *A61M 2016/0039* (2013.01); *A61M 2205/13* (2013.01); *A61M 2205/3303* (2013.01); *A61M 2205/3306* (2013.01); *A61M 2205/3334* (2013.01); *A61M 2205/3375* (2013.01); *A61M 2205/3553* (2013.01); *A61M 2205/3569* (2013.01); *A61M 2205/3584* (2013.01); *A61M 2205/3592* (2013.01); *A61M 2205/505* (2013.01); *A61M 2205/507* (2013.01);

(Continued)

(58) Field of Classification Search
CPC ............ A61M 15/0003; A61M 15/002; A61M 15/009; A61M 15/00; A61M 15/0021; A61M 15/0065; A61M 15/0066; A61M 15/008; A61M 15/0091; A61M 2016/0015; A61M 2016/0018; A61M 2016/0027; A61M 2016/003; A61M 2016/0033; A61M 2016/0039; A61M 2205/3306; A61M 2205/3334; A61M 11/02; A61M 2230/40; A61M 3/00; A61M 3/02; A61K 9/008; A61K 9/124
See application file for complete search history.

(56) References Cited

U.S. PATENT DOCUMENTS 5,333,106 A * 7/1994 Lanpher .................. G09B 5/02
128/200.12
5,347,998 A 9/1994 Hodson et al.
(Continued)

FOREIGN PATENT DOCUMENTS

EP 1005916 A1 7/2000
WO WO 2014/068504 A2 5/2014

OTHER PUBLICATIONS

PCT International Search Report; International App. No. PCT/US2015/044773; dated Nov. 13, 2015; pp. 1-4.
(Continued)

*Primary Examiner* — Jan Christopher L Merene
*Assistant Examiner* — Joseph D Boecker

(57) ABSTRACT

The present disclosure relates to devices, systems, and methods that may be used to supplement inhaler use.

33 Claims, 27 Drawing Sheets

(52) U.S. Cl.
CPC . *A61M 2205/581* (2013.01); *A61M 2205/582* (2013.01); *A61M 2205/583* (2013.01); *A61M 2230/40* (2013.01)

(56) References Cited

U.S. PATENT DOCUMENTS

| | | | |
|---|---|---|---|
| 5,392,768 A * | 2/1995 | Johansson | A61M 15/00 128/200.14 |
| 5,497,764 A | 3/1996 | Ritson et al. | |
| 5,540,934 A | 7/1996 | Touitou | |
| 5,672,581 A | 9/1997 | Rubsamen et al. | |
| 6,142,146 A | 11/2000 | Abrams et al. | |
| 6,197,333 B1 | 3/2001 | Onyuksel et al. | |
| 6,221,385 B1 | 4/2001 | Camu et al. | |
| 6,316,024 B1 | 11/2001 | Allen et al. | |
| 6,335,267 B1 | 1/2002 | Iwamatsu et al. | |
| 6,354,516 B1 | 3/2002 | Patel et al. | |
| 6,534,018 B1 | 3/2003 | Baker et al. | |
| 6,543,443 B1 | 4/2003 | Klimowicz et al. | |
| 6,623,671 B2 | 9/2003 | Coe et al. | |
| 6,684,880 B2 | 2/2004 | Trueba | |
| 6,739,333 B1 | 5/2004 | Hoelz et al. | |
| 6,759,057 B1 | 7/2004 | Weiner et al. | |
| 6,770,291 B2 | 8/2004 | Smyth-Templeton et al. | |
| 6,855,296 B1 | 2/2005 | Baker et al. | |
| 6,890,555 B1 | 5/2005 | Desai et al. | |
| 7,958,887 B2 | 6/2011 | Kelliher et al. | |
| 8,414,915 B2 | 4/2013 | Cipolla et al. | |
| 8,539,945 B2 | 9/2013 | Solomon et al. | |
| 8,662,381 B2 | 3/2014 | Kaar et al. | |
| 8,689,785 B2 | 4/2014 | Wright et al. | |
| 2002/0168322 A1* | 11/2002 | Clark | A61M 15/00 424/45 |
| 2003/0101991 A1 | 6/2003 | Trueba | |
| 2004/0084044 A1 | 5/2004 | Childers et al. | |
| 2005/0133024 A1* | 6/2005 | Coifman | A61B 5/087 128/200.14 |
| 2005/0150488 A1 | 7/2005 | Dave | |
| 2005/0196345 A1 | 9/2005 | Diederichs et al. | |
| 2005/0247312 A1 | 11/2005 | Davies | |
| 2005/0251289 A1 | 11/2005 | Bonney et al. | |
| 2005/0274378 A1 | 12/2005 | Bonney et al. | |
| 2007/0157931 A1* | 7/2007 | Parker | A61M 11/005 128/204.23 |
| 2007/0240712 A1 | 10/2007 | Fleming et al. | |
| 2008/0138397 A1 | 6/2008 | Schuster et al. | |
| 2008/0308101 A1 | 12/2008 | Spandorfer | |
| 2011/0182831 A1 | 7/2011 | Gonda | |
| 2012/0136270 A1 | 5/2012 | Leuthardt et al. | |
| 2012/0183949 A1 | 7/2012 | Hyde et al. | |
| 2012/0282328 A1 | 11/2012 | Cipolla et al. | |
| 2012/0305011 A1 | 12/2012 | Gonda | |
| 2013/0104624 A1 | 5/2013 | Devine | |
| 2013/0112199 A1 | 5/2013 | Von Sckuckmann et al. | |
| 2013/0186398 A1 | 7/2013 | Baillet et al. | |
| 2013/0206141 A1 | 8/2013 | Thoemmes et al. | |
| 2014/0007873 A1 | 1/2014 | Smutney et al. | |
| 2014/0007874 A1 | 1/2014 | Ellwanger et al. | |
| 2014/0014105 A1 | 1/2014 | Berenshteyn et al. | |
| 2014/0053838 A1 | 2/2014 | Berenshteyn et al. | |
| 2014/0053839 A1 | 2/2014 | Nakamura et al. | |
| 2014/0083421 A1 | 3/2014 | Smutney et al. | |
| 2014/0190496 A1* | 7/2014 | Wensley | A24F 47/008 131/273 |
| 2014/0251330 A1 | 9/2014 | Collins et al. | |
| 2015/0122257 A1* | 5/2015 | Winkler | A61M 11/02 128/203.15 |
| 2015/0196060 A1* | 7/2015 | Wensley | A61M 11/042 392/390 |
| 2017/0106153 A1* | 4/2017 | Davidson | A61K 9/007 |

OTHER PUBLICATIONS

European Patent Office, Extended European Search Report, Pursuant to Rule 62 EPC; App. No. EP 15831963.2; dated Mar. 27, 2018; pp. 1-7.
"Evaluating Transdermal Alcohol Measuring Devices: Final Report"; U.S. Department of Transportation; Nov. 2007, pp. i-87; National Highway Traffic Safety Administration (NHTSA).
"Guidelines for Spray Nozzle Selection"; Spraying Systems Co.; www.spray.com; 2014, p. 1-4.
"Merck Index"; Merck and Co., 2001, 13$^{th}$ edition; Whitehouse Station, NJ, USA.
"Physicians' Desk Reference"; Thomson PDR, 2004. 58th edition; Montvale, NJ, USA.
Bhalaria, M.K.; Naik, Sachin; Misra, A.N.; "Ethosomes: A novel delivery system for antifungal drugs in the treatment of topical fungal diseases"; Indian Journal of Experimental Biology; May 2009, p. 368-375, vol. 47; India.
Coates, Matthew S.; Chan, Ham-Kin; Fletcher, David F.; Raper, Judy A.; "Effect of Design on the Performance of a Dry Powder Inhaler Using Computational Fluid Dynamics"; Journal of Pharmaceutical Sciences, Jun. 2006, p. 1382-1392, vol. 95, No. 6; USA.
Copley, Mark; "Assessing dry powder inhalers"; Copley Science; Jan. 2010; p. 1-8; USA.
Dave, Vivek; Kumar, Dhirendra; Lewis, Shaila; Paliwal, Sarvesh; "Ethosome for Enhanced Transdermal Drug Delivery of Aceclofenac"; International Journal of Drug Delivery; 2010, p. 81-92; http://www.arjounrals.org/ijdd.html.
Newman, Stephen P., PHD; "Principles of Metered-Dose Inhaler Design"; Respiratory Care, Sep. 2005, p. 1177-1190, vol. 50 No. 9; USA.
Nielsen, K.G.; Skov, M.; Klug, B.; Ifversen, M.; Bisgaard, H.; "Flow-dependent effect of formoterol dry-powder inhaled from the Aerolizer®"; European Respiratory Journal; 1997, p. 2105-2109, vol. 10; United Kingdom.
Sheth, Ketan K., MD., MBA.; George, Maureen R., MSN., RN., CS.; Kelly, H. William, Pharmd; "Dry Powder Inhalers in the Treatment of Asthma: A continuing education monograph for physicians, nurses, pharmacists, physician assistants, and respiratory therapists."; Meniscus Limited; 2002; USA.
Terzano, C.; "Metered dose inhalers and spacer devices"; European Review for Medical and Pharmacological Sciences; 1999, p. 159-169, vol. 3; Department of Cardiovascular and Respiratory Sciences, "La Sapienza" University; Rome, Italy.
Troy, David B.; Beringer, Paul; "Remington: The Science and Practice of Pharmacy"; Lippincott, Williams & Wilkins; 2000, 20$^{th}$ edition; Baltimore, MD, USA.
Webster, Gregory D.; Gabler, Hampton C.; "Feasibility of Transdermal Ethanol Sensing for the Detection of Intoxicated Drivers"; Center for Injury Biomechanics; Oct. 2007, pp. 449-464; Virginia Polytechnic and State University; Blacksburg, VA, USA.

* cited by examiner

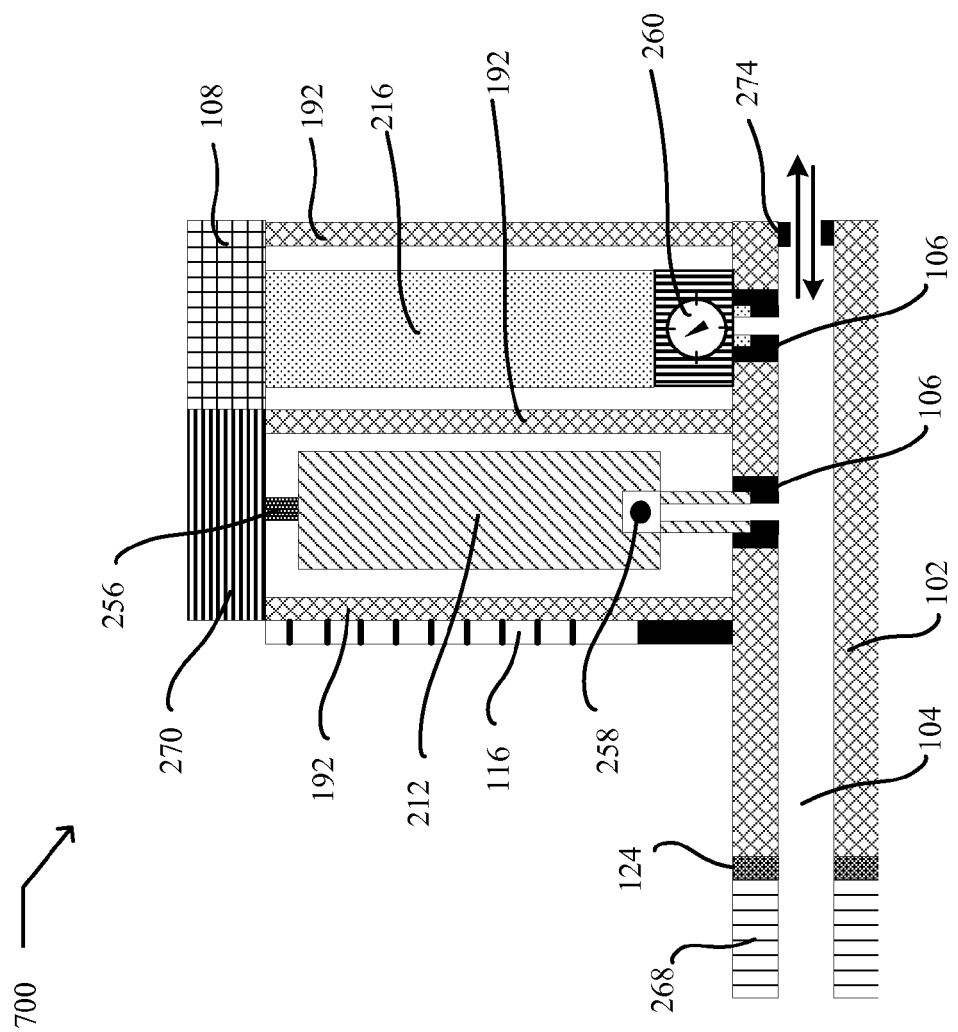

METHODS, SYSTEMS, AND DEVICES RELATED TO A SUPPLEMENTAL INHALER

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

U.S. patent application Ser. No. 14/459,075, entitled SYSTEMS, METHODS, AND DEVICES TO INCENTIVIZE INHALER USE, naming Jesse R. Cheatham, III, Roderick A. Hyde, Robert C. Petroski, Lowell L. Wood, Jr., and Victoria Y. H. Wood as inventors, filed 13 Aug. 2014, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In one aspect, an inhaler includes, but is not limited to, a housing having at least one flow channel disposed therein, at least one port disposed in the housing operably coupled to the at least one flow channel and configured to provide fluid communication between at least one agent reservoir and at least one propellant reservoir and the at least one flow channel; at least one sensor operably coupled with the at least one flow channel; at least one actuator configured to facilitate at least partial release from either or both of the at least one agent reservoir and the at least one propellant reservoir when the at least one agent reservoir and the at least one propellant reservoir are operably coupled to the at least one port; and at least one control unit configured to receive information from the at least one sensor and direct the at least one actuator to facilitate at least partial release from either or both of the at least one agent reservoir and the at least one propellant reservoir. In some embodiments, an inhaler may optionally include at least one agent reservoir operably coupled to the at least one port. In some embodiments, an inhaler may optionally include at least one propellant reservoir operably coupled to the at least one port. In some embodiments, an inhaler may optionally include at least one dose counter. In some embodiments, an inhaler may optionally include at least one flow indicator. In some embodiments, an inhaler may optionally include at least one controllable flow valve operably coupled with the at least one flow channel. In addition to the foregoing, other inhaler aspects are described in the claims, drawings, and text forming a part of the present disclosure.

In one aspect, a method includes, but is not limited to, assessing one or more parameters associated with flow through at least one flow channel disposed within an inhaler used by a subject to obtain at least one assessed flow value; calculating an amount of propellant that will increase flow through the at least one flow channel to meet or exceed a threshold flow value if the at least one assessed flow value is below the threshold flow value; and dispensing at least one agent with the amount of propellant that will cause the flow through the at least one flow channel to meet or exceed the threshold flow value. In some embodiments, a method may optionally include displaying the at least one assessed value. In some embodiments, a method may optionally include dispensing at least one additional agent. In addition to the foregoing, other method aspects are described in the claims, drawings, and text forming a part of the present disclosure.

In one aspect, a system includes, but is not limited to, circuitry configured to assess one or more parameters associated with flow through at least one flow channel disposed within an inhaler used by a subject to obtain at least one assessed flow value; circuitry configured to calculate an amount of propellant that will increase flow through the at least one flow channel to meet or exceed a threshold flow value if the at least one assessed flow value is below the threshold flow value; and circuitry configured to dispense at least one agent with the amount of propellant that will cause the flow through the at least one flow channel to meet or exceed the threshold flow value. In some embodiments, a system may optionally include circuitry configured to display the at least one assessed value. In some embodiments, a system may optionally include circuitry configured to select and dispense at least one additional agent. In addition to the foregoing, other system aspects are described in the claims, drawings, and text forming a part of the present disclosure.

In one aspect, a system includes, but is not limited to, means for assessing one or more parameters associated with flow through at least one flow channel disposed within an inhaler used by a subject to obtain at least one assessed flow value; means for calculating an amount of propellant that will increase flow through the at least one flow channel to meet or exceed a threshold flow value if the at least one assessed flow value is below the threshold flow value; and means for dispensing at least one agent with the amount of propellant that will cause the flow through the at least one flow channel to meet or exceed the threshold flow value. In some embodiments, a system may optionally include means for displaying the at least one assessed value. In some embodiments, a system may optionally include means for dispensing at least one additional agent. In addition to the foregoing, other system aspects are described in the claims, drawings, and text forming a part of the present disclosure.

In one aspect, a system includes, but is not limited to, a non-transitory signal-bearing medium bearing one or more instructions that, when executed by one or more processing components, direct performance of operations that include at least: assessing one or more parameters associated with flow through at least one flow channel disposed within an inhaler used by a subject to obtain at least one assessed flow value; calculating an amount of propellant that will increase flow through the at least one flow channel to meet or exceed a threshold flow value if the at least one assessed flow value is below the threshold flow value; and dispensing at least one agent with the amount of propellant that will cause the flow through the at least one flow channel to meet or exceed the threshold flow value. In some embodiments, a system may optionally include one or more instructions that direct performance of an operation that includes at least displaying the at least one assessed value. In some embodiments, a system may optionally include one or more instructions that direct performance of an operation that includes at least dispensing at least one additional agent. In some embodiments, a system may optionally include a non-transitory signal-bearing medium that includes at least a computer-readable medium. In some embodiments, a system may optionally include a non-transitory signal-bearing medium that includes at least a recordable medium. In some embodiments, a system may optionally include a non-transitory signal-bearing medium that includes at least a communications medium. In addition to the foregoing, other system aspects are described in the claims, drawings, and text forming a part of the present disclosure.

In one or more various aspects, means include but are not limited to circuitry and/or programming for effecting the herein referenced functional aspects; the circuitry and/or programming can be numerous combinations of hardware, software, and/or firmware configured to effect the herein referenced functional aspects depending upon the design choices of the system designer. In addition to the foregoing, other system aspects means are described in the claims, drawings, and/or text forming a part of the present disclosure.

In one or more various aspects, related systems include but are not limited to circuitry and/or programming for effecting the herein-referenced method aspects; the circuitry and/or programming can be numerous combinations of hardware, software, and/or firmware configured to effect the herein referenced method aspects depending upon the design choices of the system designer. In addition to the foregoing, other system aspects are described in the claims, drawings, and/or text forming a part of the present application.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 7 illustrates a cross-sectional partial side view of an example inhaler 700 in which embodiments may be implemented.

DETAILED DESCRIPTION

Figure 1:
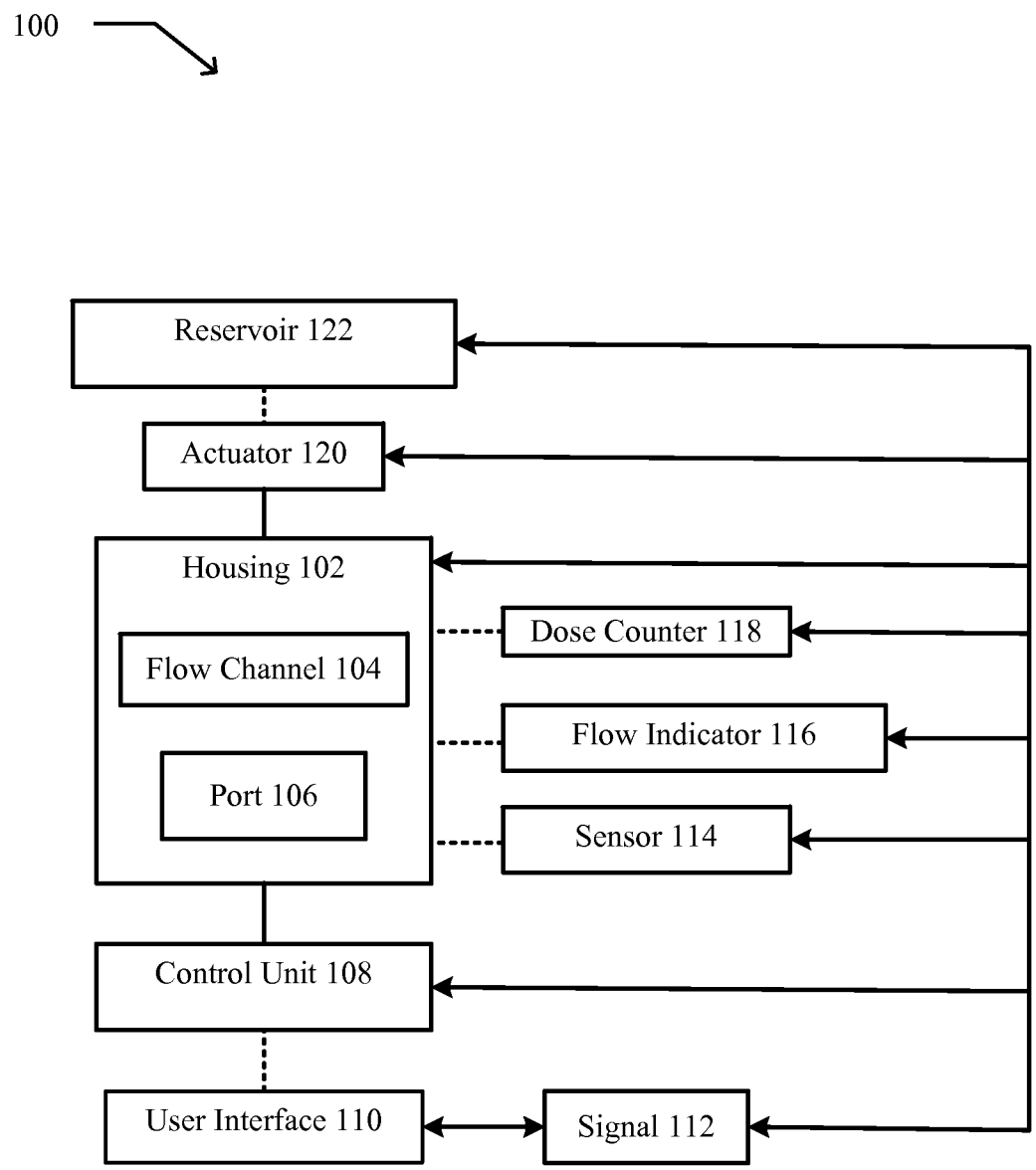
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example system 100 in which numerous embodiments may be implemented. In some embodiments, system 100 may be implemented as an inhaler. In some embodiments, system 100 may include a housing 102 having at least one flow channel 104 disposed therein. In some embodiments, system 100 may include at least one port 106 disposed in the housing 102 and operably coupled to at least one flow channel 104 and configured to provide fluid communication between at least two reservoirs 122 and at least one flow channel 104. In some embodiments, system 100 may include one or more actuators 120. In some embodiments, system 100 may include one or more reservoirs 122. In some embodiments, system 100 may include one or more dose counters 118. In some embodiments, system 100 may include one or more flow indicators 116. In some embodiments, system 100 may include one or more control units 108. In some embodiments, system 100 may include one or more sensors 114. In some embodiments, system 100 may include one or more user interfaces 110. In some embodiments, system 100 may include one or more signals 112.

Figure 2:
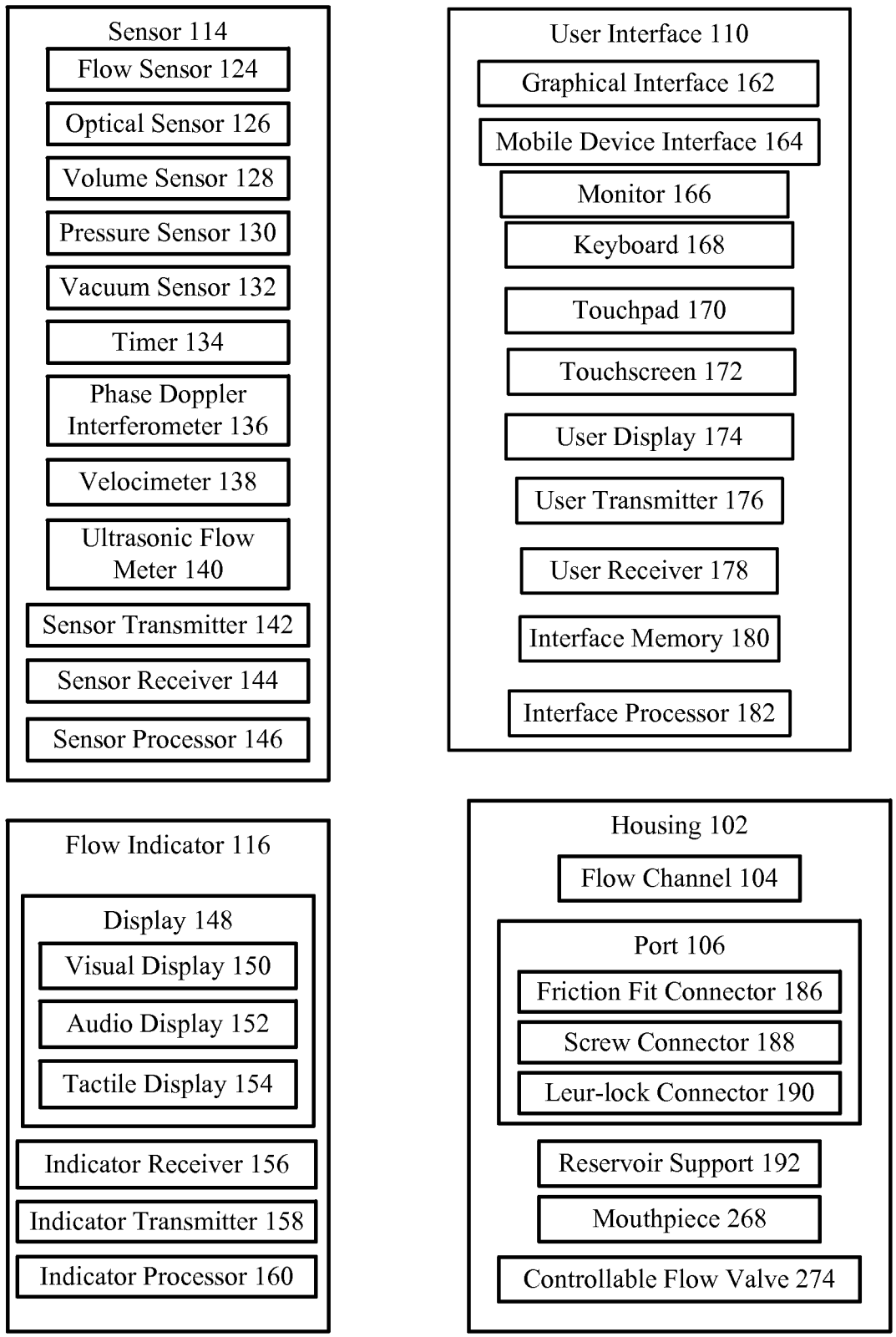
FIG. 2 illustrates example components of system 100 in which embodiments may be implemented.

FIG. 2 illustrates example embodiments of components that may be included in system 100. The illustrated components include a sensor 114, a flow indicator 116, a user interface 110, and a housing 102.

Figure 3:
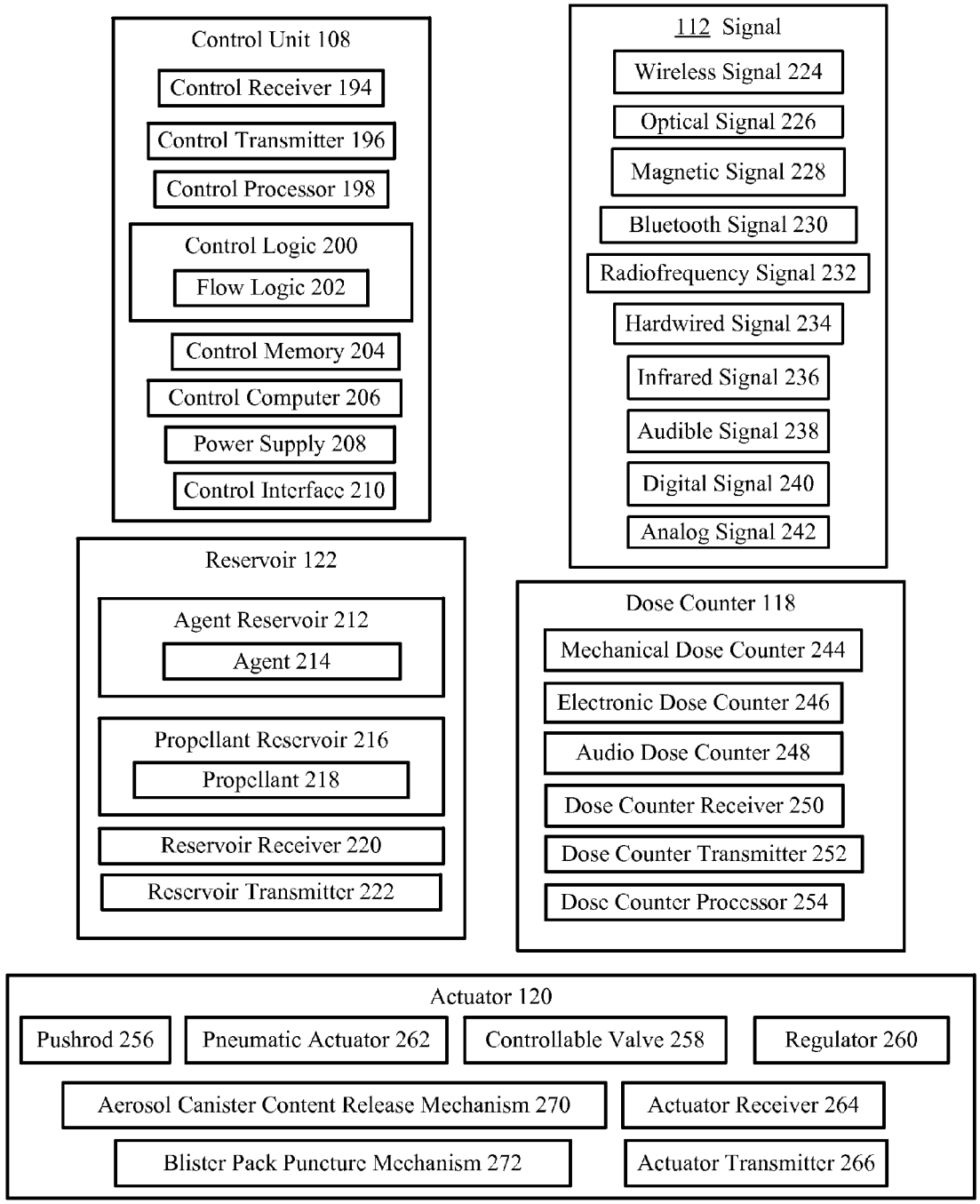
FIG. 3 illustrates example components of system 100 in which embodiments may be implemented.

FIG. 3 illustrates example embodiments of components that may be included in system 100. The illustrated components include a control unit 108, a signal 112, a dose counter 118, an actuator 120, and a reservoir 122.

Housing

With reference to FIGS. 1-3, in some embodiments, system 100 may include one or more housings 102. A housing 102 may be configured in numerous ways. In some embodiments, a housing may be configured for inclusion within an inhaler. In some embodiments, a housing 102 may include one or more flow channels 104 disposed therein. In some embodiments, a housing 102 may include a single flow channel 104 disposed therein. In some embodiments, a housing 102 may include a plurality of flow channels 104 disposed therein. For example, in some embodiments, a housing 102 may include a first flow channel 104 disposed therein that is configured to direct a first agent 214 to a subject using the inhaler, and a second flow channel 104 disposed therein that is configured to direct a second agent 214 to the subject.

In some embodiments, a housing 102 may include one or more ports 106 disposed therein. In some embodiments, a housing 102 may include at least one port 106 disposed within the housing 102 and operably coupled to at least one flow channel 104 and configured to provide fluid communication between at least one reservoir 122 and at least one flow channel 104. Accordingly, in some embodiments, a port 106 may be configured to operably couple with one or more reservoirs 122 and direct contents released from the one or more reservoirs 122 into one or more flow channels 104 disposed within a housing 102. In some embodiments, a port 106 may be configured to facilitate delivery of one or more powdered agents 214 from an agent reservoir 212 into a flow channel 104. In some embodiments, a port 106 may be configured to facilitate delivery of propellant 218 from a propellant reservoir 216 into a flow channel 104. In some embodiments, a port 106 may be aligned with an actuator 120 that is configured to propel a powdered formulation into a flow channel 106. For example, in some embodiments, a port 106 may be configured to allow a pushrod actuator 256 to pass through the port 106 in order to propel a powdered formulation from a reservoir 122 into a flow channel 104. In some embodiments, a port 106 may be configured to facilitate delivery of one or more aerosolized formulations from a reservoir 122 into a flow channel 104.

For example, in some embodiments, a port 106 may be configured to operably couple with an aerosol canister that includes a canister body and a valve stem that extends from the canister body and into a port 106 that is aligned with a flow channel 104. In some embodiments, a housing 102 may include at least one port 106 disposed in the housing 102 and operably coupled to at least one flow channel 104 and configured to receive one or more reservoirs 122. In some embodiments, a housing 102 may include two or more ports 106 disposed within the housing 102 that are each operably coupled to at least one flow channel 104 and are each configured to receive a reservoir 122. In some embodiments, a housing 102 may include one port 106 disposed in the housing 102 that is operably coupled to at least one flow channel 104 and configured to receive two or more reservoirs 122. A port 106 may include numerous types of connectors that allow one or more reservoirs 122 to be operably coupled to the port 106. Examples of such connectors include, but are not limited to, friction fit connectors 186, screw connectors 188, Leur-lock connectors 190, and the like.

In some embodiments, a port 106 may include an actuator 120 that is operable to facilitate at least partial release of contents from one or more operably coupled reservoirs 122. For example, in some embodiments, a port 106 may include a controllable valve 258 that may be opened and closed to facilitate at least partial release of contents from an operably coupled reservoir 122. In some embodiments, such a controllable valve 258 may be operably coupled with a control unit 108 that is configured to control the operation of the controllable valve 258. In some embodiments, such a controllable valve 258 may be operably coupled with a sensor 114. In some embodiments, such a controllable valve 258 may be operably coupled with a sensor 114 that is configured to control the operation of the controllable valve 258. In some embodiments, such a controllable valve 258 may be operably coupled with a control unit 108 and a sensor 114 that are configured to control operation of the controllable valve 258. In some embodiments, a port 106 may include a controllable valve 258 that may be opened and closed to facilitate at least partial release of contents from an agent reservoir 212. In some embodiments, a port 106 may include a controllable valve 258 that may be opened and closed to facilitate at least partial release of contents from a propellant reservoir 216.

In some embodiments, a port 106 may include a regulator 260 that may be configured to facilitate at least partial release of contents from an operably coupled reservoir 122. In some embodiments, a port 106 may include a regulator 260 that may be opened and closed to facilitate at least partial release of contents from an agent reservoir 212. In some embodiments, a port 106 may include a regulator 260 that may be opened and closed to facilitate at least partial release of contents from a propellant reservoir 216. In some embodiments, such a regulator 260 may be operably coupled with a control unit 108 that is configured to control the operation of the regulator 260. In some embodiments, such a regulator 260 may be operably coupled with a sensor 114. In some embodiments, such a regulator 260 may be operably coupled with a sensor 114 that is configured to control the operation of the regulator 260. In some embodiments, such a regulator 260 may be operably coupled with a control unit 108 and a sensor 114 that are configured to control operation of the regulator 260. Accordingly, a port 106 may be configured in numerous ways.

In some embodiments, a housing 102 may include at least one reservoir support 192. For example, in some embodiments, a housing 102 may include at least one reservoir support 192 that is configured to support at least one aerosol canister that includes a canister body and a valve stem that extends from the canister body with the valve stem being receivable by a port 106. In some embodiments, a housing 102 may include at least one reservoir support 192 that is configured to support at least one agent reservoir 212 that includes a conveyor with at least one conveying drive configured to advance a blister strip that includes a plurality of blister packs that are filled with an agent 214. In some embodiments, a housing 102 may include at least one reservoir support 192 that is configured to support at least one propellant reservoir 216. For example, in some embodiments, a housing 102 may include at least one reservoir support 192 that is configured to support a propellant reservoir 216 that is configured as a compressed gas cylinder.

In some embodiments, a housing 102 may include at least one mouthpiece 268 that is operably coupled with one or more flow channels 104. In some embodiments, a mouthpiece 268 may be operably coupled with one or more sensors 114. A mouthpiece 268 may be operably coupled with numerous types of sensors 114. Examples of such sensors 114 include, but are not limited to, optical sensors 126, volume (or flow rate) sensors 128, pressure sensors 130, vacuum sensors 132, timers 134, phase Doppler interferometers 136, velocimeters 138, ultrasonic flow meters 140, and the like. In some embodiments, a mouthpiece 268 may include a sensor 14 that is configured to assess the quality of physical contact between the mouth of a subject and the mouthpiece 268. For example, in some embodiments, a pressure sensor (e.g., strain gauge, stress gauge, deformation sensor, and the like) may be configured to assess the quality of physical contact between the mouth of a subject and the mouthpiece 268.

Reservoir

With continued reference to FIGS. 1-3, in some embodiments, system 100 may include one or more reservoirs 122. A reservoir 122 may be configured in numerous ways. In some embodiments, a reservoir 122 may be built-in to the housing. In some embodiments, a reservoir 122 may be detachably coupled to the housing, e.g., via reservoir support 192. In some embodiments a reservoir 122 may contain multiple different agents. In some embodiments, system 100 may include multiple reservoirs 122, each holding at least one separate agent. In some embodiments, a reservoir 122 may include one or more reservoir receivers 220. In some embodiments, a reservoir 122 may include one or more reservoir transmitters 222. Accordingly, in some embodiments, a reservoir 122 may transmit one or more signals 112. In some embodiments, a reservoir 122 may receive one or more signals 112.

In some embodiments, a reservoir 122 may be operably coupled with a control unit 108. In some embodiments, a reservoir 122 may be operably coupled with a control unit 108 that controls operation of the reservoir 122. For example, in some embodiments, a control unit 108 may direct an agent reservoir 212 that includes a conveyor with at least one conveying drive to advance a blister strip that includes a plurality of blister packs that are filled with a powdered agent 214. In some embodiments, a reservoir 122 may be operably coupled with a sensor 114. In some embodiments, a reservoir 122 may be operably coupled with a sensor 114 that controls operation of the reservoir 122. For example, in some embodiments, a sensor 114 may detect a quantity of an agent 214 released from an agent reservoir 212 and then direct a conveying drive in an agent reservoir 212 to advance a blister strip that includes a plurality of blister packs that are filled with a powdered agent 214. In some embodiments, an agent reservoir 122 may be operably coupled with a sensor 114 that detects a quantity of agent 214 contained within the agent reservoir 212. In some embodiments, a propellant reservoir 216 may be operably coupled with a sensor 114 that detects a quantity of propellant 218 contained within the propellant reservoir 216. In some embodiments, an agent reservoir 212 may be operably coupled with a sensor 114 that detects a quantity of an agent 214 contained within the agent reservoir 212 and a dose counter 118 that displays the amount of agent 214 contained within the agent reservoir 212. In some embodiments, a propellant reservoir 216 may be operably coupled with a sensor 114 that detects a quantity of propellant 218 contained within the propellant reservoir 216 and a dose counter 118 that displays the amount of propellant 218 contained within the propellant reservoir 216.

An agent reservoir 212 may contain numerous types of agents 214. Examples of such agents 214 include, but are not limited to, surfactant lipids, steroids, anti-inflammatory drugs, bronchodilators, leukotriene modifiers, long-acting beta antagonists, 1,3-dimethylxanthine, short-acting beta agonists, [8-methyl-8-(1-methylethyl)-8-azoniabicyclo [3.2.1]oct-3-yl]3-hydroxy-2-phenyl-propanoate, antibodies, and the like (see e.g., *Remingtion: The Science and Practice of Pharmacy*, Lippincott, Williams & Wilkins, 20th edition, Baltimore, Md., USA (2000), *Physicians' Desk Reference*, Thomson PDR, 58th edition, Montvale, N.J. (2004); *Merck Index*, Merck and Co., 13th edition., Whitehouse Station, N.J. (2001); the relevant portions of which are hereby incorporated by reference).

A propellant reservoir 216 may contain numerous types of propellants 218. Examples of such propellants 218 include, but are not limited to, chlorofluorocarbons, hydrofluoroalkanes, compressed gases (e.g., air, nitrogen, oxygen), and the like. In some embodiments, a propellant reservoir 216 may include a combination of propellants 218.

Agents 214 may be included in numerous types of formulations. In some embodiments, a formulation may be a liquid formulation. Accordingly, in some embodiments, a formulation may include a carrier fluid. In some embodiments, a formulation may be an aerosolized formulation. In some embodiments, a formulation may be a powdered formulation. In some embodiments, a formulation may be a powdered inhalation formulation. Accordingly, in some embodiments, a formulation may include a carrier powder. In some embodiments, a formulation may include one agent 214. In some embodiments, a formulation may include more than one agent 214. Accordingly, in some embodiments, a formulation may include numerous combinations of agents 214.

In some embodiments, a reservoir 122 may be configured to contain a liquid formulation. For example, in some embodiments, an agent reservoir 212 may be configured as an aerosol canister that includes a canister body and a valve stem that extends from the canister body. In some embodiments, contents may be at least partially released from an aerosol canister by depressing the valve stem relative to the canister body. In some embodiments, a reservoir 122 may be configured to contain a powdered formulation. For example, in some embodiments, an agent reservoir 212 may include a conveyor with at least one conveying drive configured to advance a blister strip that includes a plurality of blister packs that are filled with a powdered agent 214.

Actuator

With continued reference to FIGS. 1-3, in some embodiments, system 100 may include one or more actuators 120. System 100 may include numerous types of actuators 120 and combinations of actuators 102. In some embodiments, an actuator 120 may be configured to facilitate at least partial release of contents from one or more reservoirs 122. For example, in some embodiments, an actuator 120 may be configured to facilitate at least partial release of one or more agents 214 from one or more agent reservoirs 212. In some embodiments, an actuator 120 may be configured to facilitate at least partial release of propellant 218 from one or more propellant reservoirs 216.

Examples of actuators 120 include, but are not limited to, controllable valves 258, pushrod actuators 258, regulators 260, pneumatic actuators 262, and the like (e.g. linkages, rockers, electro-magnets, switches, etc.). In some embodiments, an actuator 120 may be configured as an aerosol canister content release mechanism 270 that includes a pushrod actuator 256 that can depress an aerosol canister to open a controllable valve 258 and release contents of the aerosol canister. In some embodiments, an actuator 256 may be configured as a blister pack puncture mechanism 270 that includes a pushrod actuator 256 that can puncture a blister pack. In some embodiments, an actuator 120 may be configured as a blister pack puncture mechanism that includes a pushrod actuator 256 that can puncture a blister pack and propel a powdered inhalation formulation 214 from the blister pack into the at least one flow channel 104.

In some embodiments, an actuator 120 may include one or more actuator receivers 264. In some embodiments, an actuator 120 may include one or more actuator transmitters 266. Accordingly, in some embodiments, an actuator 120 may transmit one or more signals 112. In some embodiments, an actuator 120 may receive one or more signals 112. In some embodiments, an actuator 120 may be operably coupled to one or more sensors 114. Accordingly, in some embodiments, an actuator 120 may be controlled in response to one or more parameters that are detected by one or more sensors 114. For example, in some embodiments, a sensor 114 may detect a quantity of an agent 214 flowing through a flow channel 104 and control the operation of one or more operably coupled actuators 120 in response to the quantity of agent 214 detected. In some embodiments, a sensor 114 may detect a quantity of propellant 218 flowing through a flow channel 104 and control the operation of one or more operably coupled actuators 120 in response to the quantity of propellant 218 detected. In some embodiments, a sensor 114 may detect when a subject using an inhaler is inhaling and activate one or more operably coupled actuators 120 to facilitate at least partial release from a reservoir 122 during the inhalation cycle. In some embodiments, a sensor 114 may detect when a subject using an inhaler is exhaling and deactivate one or more operably coupled actuators 120 to halt release from a reservoir 122 during the exhalation cycle. In some embodiments, a sensor 114 may detect when a subject using an inhaler is holding their breath and deactivate one or more operably coupled actuators 120 to halt release from a reservoir 122 during the breath holding cycle.

Dose Counter

As further shown in FIGS. 1-3, in some embodiments, system 100 may include one or more dose counters 118. Dose counters 118 may be configured in numerous ways. In some embodiments, a dose counter 118 may include one or more dose counter receivers 250. In some embodiments, a dose counter 118 may include one or more dose counter transmitters 252. Accordingly, in some embodiments, a dose counter 118 may transmit one or more signals 112. In some embodiments, a dose counter 118 may receive one or more signals 112.

In some embodiments, a dose counter 118 may be a mechanical dose counter 244. For example, in some embodiments, a mechanical dose 244 counter may include a ratchet mechanism that advances a numerical indicator every time that an inhaler is activated to dispense an agent 214 (see e.g., Wright et al., Dispending apparatus, U.S. Pat. No. 8,689,785 and Kaar et al., Dose counter for a metered-dose inhaler, U.S. Pat. No. 8,662,381; herein incorporated by reference). In some embodiments, a mechanical dose 244 counter may include a ratchet mechanism that advances a numerical indicator every time that an inhaler is activated to release propellant 218. In some embodiments, a dose counter 118 may be an electronic dose counter 246 that includes an electronic display that displays the number of times that an inhaler is activated to dispense an agent 214 and/or release propellant 218 (e.g., Solomon et al., Dose counter and recording method, U.S. Pat. No. 8,539,945; herein incorporated by reference). In some embodiments, a dose counter 118 may be an audio dose counter 248 that includes an audio display. In some embodiments, an audio display may be configured to indicate the number of times that an inhaler is activated to dispense an agent 214 and/or propellant 218. For example, in some embodiments, an audio dose counter 248 may receive information associated with the number of times that an inhaler has been activated to release an agent 214 and/or propellant 218 and provide an audio display in the form of a human voice to report the information.

In some embodiments, a dose counter 118 may be operably coupled with and receive information from one or more sensors 114. In some embodiments, a dose counter 118 may be operably coupled with and receive information from one or more control units 108. In some embodiments, a dose counter 118 may receive information associated with the quantity of an agent 214 or propellant 218 that is contained within an agent reservoir 212 or a propellant reservoir 216 and then display the information. In some embodiments, a dose counter 118 may receive information associated with the quantity of an agent 214 or propellant 218 that is released through one or more flow channels 104 and then display the information.

Flow Indicator

With continued reference to FIGS. 1-3, in some embodiments, system 100 may include one or more flow indicators 116. Flow indicators 116 may be configured in numerous ways. In some embodiments, a flow indicator 116 may include one or more indicator receivers 156. In some embodiments, a flow indicator 116 may include one or more indicator transmitters 158. Accordingly, in some embodiments, a flow indicator 116 may transmit one or more signals 112. In some embodiments, a flow indicator 116 may receive one or more signals 112. In some embodiments, a flow indicator 116 may include one or more indicator processors 160. Accordingly, in some embodiments, a flow indicator 116 may process information.

In some embodiments, a flow indicator 116 may include a display 148. A flow indicator 116 may include numerous types of displays 148. Examples of such displays 148 include, but are not limited to, visual displays 150, audio displays 152, tactile (or touch screen) displays 154, and the like. Examples of visual displays 150 include, but are not limited to, electronic visual displays 150 such as active displays and passive displays. In some embodiments, a visual display 150 may be contained within a mobile device such as a cellular telephone, a personal digital assistant, a notepad computer, a tablet, a laptop, and the like. Accordingly, in some embodiments, a control unit 108 may be configured to transmit flow information that is received by and displayed on a mobile device. In some embodiments, a sensor 114 may be configured to transmit flow information that is received by and displayed on a mobile device. In some embodiments, flow information may be displayed on a head mounted display 148 such as an optical head-mounted display 148.

In some embodiments, a flow indicator 116 may include a tactile display 154 that is configured to vibrate. For example, in some embodiments, a flow indicator 116 may vibrate with an intensity that is related to flow through one or more flow channels 104 disposed within an inhaler. In some embodiments, a flow indicator 116 may include an audio display 152 that is configured to emit one or more sounds. For example, in some embodiments, a flow indicator 116 may have a tone that is related to the intensity of flow through one or more flow channels 104 disposed within an inhaler. A flow indicator 116 may display information that is related to numerous parameters associated with flow through one or more flow channels 104 disposed within an inhaler. For example, in some embodiments, a flow indicator 116 may indicate one or more levels of flow of an agent 214 through a flow channel 104. In some embodiments, a flow indicator 116 may indicate one or more levels of a vacuum applied to a flow channel 104 by a subject using the inhaler. In some embodiments, a flow indicator 116 may indicate a volume of gas flowing through a flow channel 104. In some embodiments, a flow indicator 116 may indicate a velocity with which gas flows through a flow channel 104. Accordingly, a flow indicator 116 may be configured to display information that is related to numerous parameters.

In some embodiments, a flow indicator 116 may be operably coupled with one or more control units 108. In some embodiments, a flow indicator 116 may be operably coupled with one or more sensors 114. In some embodiments, a flow indicator 116 may be operably coupled with one or more control units 108 and one or more sensors 114. In some embodiments, a flow indicator 116 may be configured to display processed information that is received from a control unit 108. For example, in some embodiments, a flow indicator 116 may indicate a quantity of an agent 214 that flows through a flow channel 104. In some embodiments, a flow indicator 116 may indicate a quantity of an agent 214 to be released to reach a predetermined dosage level.

Sensor

As further shown in FIGS. 1-3, in some embodiments, system 100 may include one or more sensors 114. System 100 may include numerous types of sensors 114. Examples of sensors 114 include, but are not limited to, flow sensors 124 such as gas flow sensors 124 and liquid flow sensors 124, volume (or flow rate) sensors 128, optical sensors 126, pressure sensors 130, vacuum sensors 132, timers 134, phase Doppler interferometers 136, velocimeters 138, ultrasonic flow meters 140, and the like.

In some embodiments, a sensor 114 may include one or more sensor receivers 144. In some embodiments, a sensor 114 may include one or more sensor transmitters 142. In some embodiments, a sensor 114 may receive one or more signals 112. In some embodiments, a sensor 114 may transmit one or more signals 112. In some embodiments, a sensor 114 may include one or more sensor processors 146. Accordingly, in some embodiments, a sensor 114 may process information.

In some embodiments, one or more sensors 114 may be operably coupled with one or more flow channels 104 that are disposed within a housing 102. In some embodiments, a sensor 114 may be configured to measure the velocity with which gas flows through a flow channel 104. In some embodiments, a sensor 114 may be configured to measure the velocity with which liquid flows through a flow channel 104. In some embodiments, a volume sensor 128 may be used to measure a volume of gas flowing through a flow channel 104. In some embodiments, a volume sensor 128 may be used to measure a volume of liquid flowing through a flow channel 104. In some embodiments, a sensor 114 may be configured to measure a quantity of an agent 214 that flows through a flow channel 104. In some embodiments, a vacuum sensor 132 may be used to measure an amount of vacuum pressure applied to a flow channel 104. In some embodiments, a pressure sensor 130 may be used to measure an amount of gas pressure applied to a flow channel 104. In some embodiments, a timer 134 may be configured to measure an amount of time related to a respiration parameter. For example, in some embodiments, a timer 134 may be used to determine a time period during one or more of an inhalation cycle, an exhalation cycle, or a breath hold cycle occurring during use of an inhaler. In some embodiments, a pressure sensor 130 may be operably coupled to a mouthpiece 268 of an inhaler and configured to assess the quality of physical contact between the mouth of a subject and the mouthpiece. Accordingly, in some embodiments, such a pressure sensor 130 may be configured to measure stress and/or strain on the mouthpiece 268.

In some embodiments, a sensor 114 may be operably coupled with one or more control units 108. Accordingly, in some embodiments, a control unit 108 may be configured to control the operation of one or more operably coupled sensors 114. In some embodiments, a sensor 114 may be operably coupled with one or more actuators 120 that are configured to facilitate at least partial release of contents from one or more reservoirs 122. For example, in some embodiments, a sensor 114 may be operably coupled to an actuator 120 and configured to facilitate at least partial release of one or more agents 214 from an agent reservoir 212 in a manner that is dependent on the quantity of an agent 214 detected flowing through a flow channel 104. In some embodiments, a sensor 114 may be coupled to a control unit 108 and to an actuator 120. Accordingly, in some embodiments, a control unit 108 may receive detected information from one or more sensors 114 and then control one or more actuators 120 in response to the information.

User Interface

With continued reference to FIGS. 1-3, in some embodiments, system 100 may include one or more user interfaces 110. System 100 may include numerous types of user interfaces 110. Examples of user interfaces 110 include, but are not limited to, graphical interfaces 162, monitors 166, touchscreens 172, touchpads 170, keyboards 168, mobile device interfaces 164, and the like. In some embodiments, a user interface 110 may include one or more user transmitters 176. In some embodiments, a user interface 110 may include one or more user receivers 178. In some embodiments, a user interface 110 may include one or more interface processors 182. Accordingly, in some embodiments, a user interface 110 may transmit one or more signals 112, receive one or more signals 112, and process one or more signals 112.

In some embodiments, a user interface 110 may transmit one or more signals 112 that are received by one or more control units 108. In some embodiments, a user interface 110 may transmit one or more signals 112 that are received by one or more sensors 114. In some embodiments, a user interface 110 may transmit one or more signals 112 that are received by one or more flow indicators 116. In some embodiments, a user interface 110 may transmit one or more signals 112 that are received by one or more dose counters 118. In some embodiments, a user interface 110 may transmit one or more signals 112 that are received by one or more actuators 120.

In some embodiments, a user interface 110 may receive one or more signals 112 that are transmitted by one or more control units 108. In some embodiments, a user interface 110 may receive one or more signals 112 that are transmitted by one or more sensors 114. In some embodiments, a user interface 110 may receive one or more signals 112 that are transmitted by one or more flow indicators 116. In some embodiments, a user interface 110 may receive one or more signals 112 that are transmitted by one or more dose counters 118.

In some embodiments, a subject may enter information into a user interface 110 that transmits one or more signals 112 that include the information that are received by one or more control units 108. Examples of such information include, but are not limited to, information related to a subject's height, weight, age, allergies, respiration parameters, physical fitness level, information related to one or more maladies associated with the subject, information related to drugs used by the subject, and the like.

Signal

Numerous types of signals 112 may be used within system 100. Examples of such signals 112 include, but are not limited to, wireless signals 224, optical signals 226, magnetic signals 228, radiofrequency signals 232, hardwired signals 234, infrared signals 236, audible signals 238, analog signals 242, digital signals 240, Bluetooth signals 230, and the like. Accordingly, system 100 may include receivers, transmitters, and processors that are configured to receive, transmit, and process numerous types of signals 112. A signal 112 may include numerous types of information. For example, in some embodiments, a signal 112 may include information associated with one or more respiration parameters. In some embodiments, a signal 112 may include information associated with release of one or more agents 214 from an agent reservoir 212. In some embodiments, a signal 112 may include information associated with release of propellant 218 from a propellant reservoir 216.

Control Unit

As further depicted in FIGS. 1-3, in some embodiments, system 100 may include one or more control units 108. In some embodiments, a control unit 108 may include one or more control computers 206. In some embodiments, a control unit 108 may include one or more control receivers 194. In some embodiments, a control unit 108 may include one or more control transmitters 196. In some embodiments, a control unit 108 may include one or more control processors 198 (e.g. digital processing devices, programmable components, Application Specific Integrated Circuits (ASICs), etc.). In some embodiments, a control unit 108 may include control memory 204. In some embodiments, a control unit 108 may include control logic 200. In some embodiments, a control unit 108 may include flow logic 202. In some embodiments, a control unit 108 may include one or more power supplies 208. In some embodiments, a control unit 108 may include one or more control interfaces 210.

In some embodiments, a control unit 108 may receive one or more signals 112 that are transmitted by one or more user interfaces 110. In some embodiments, a control unit 108 may receive one or more signals 112 that are transmitted by one or more sensors 114. In some embodiments, a control unit 108 may receive one or more signals 112 that are transmitted by one or more flow indicators 116. In some embodiments, a control unit 108 may receive one or more signals 112 that are transmitted by one or more dose counters 118. In some embodiments, a control unit 108 may receive one or more signals 112 that are transmitted by one or more actuators 120.

In some embodiments, a control unit 108 may transmit one or more signals 112 that are received by one or more user interfaces 110. In some embodiments, a control unit 108 may transmit one or more signals 112 that are received by one or more sensors 114. In some embodiments, a control unit 108 may transmit one or more signals 112 that are received by one or more actuators 120. In some embodiments, a control unit 108 may transmit one or more signals 112 that are received by one or more flow indicators 116. In some embodiments, a control unit 108 may transmit one or more signals 112 that are received by one or more dose counters 118.

In some embodiments, a control unit 108 may transmit one or more signals 112 that direct the operation of one or more actuators 120. For example, in some embodiments, a control unit 108 may transmit one or more signals 112 that direct an actuator 120 to at least partially release contents from one or more reservoirs 122. In some embodiments, a control unit 108 may transmit one or more signals 112 that direct an actuator 120 not to release contents from one or more reservoirs 122. For example, in some embodiments, a control unit 108 may receive information from one or more sensors 114 that is related to inhalation and exhalation through a flow channel 104 by a subject using an inhaler. The control unit 108 may then direct one or more actuators 120 to at least partially release contents from one or more reservoirs 122 during an inhalation cycle through an inhaler and then direct the one or more actuators 120 to not release contents from the one or more reservoirs 122 during an exhalation cycle through an inhaler. In some embodiments, a control unit 108 may direct the operation of more than one actuator 120. For example, in some embodiments, a control unit 108 may direct a first actuator 120 to at least partially release an agent 214 from an agent reservoir 212 and then direct a second actuator 120 to at least partially release propellant 218 from a propellant reservoir 216. In some embodiments, a control unit 108 may direct a first actuator 120 to at least partially release an agent 214 from an agent reservoir 212 and direct a second actuator 120 to at least partially release propellant 218 from a propellant reservoir 216 at substantially the same time.

In some embodiments, a control unit 108 may transmit one or more signals 112 that are received by one or more flow indicators 116. For example, in some embodiments, a control unit 108 may receive one or more signals 112 from a sensor 114 that include information related to respiration by a subject using an inhaler. The control unit 108 may then transmit one or more signals 112 that are received by a flow indicator 116 that direct the flow indicator 116 to indicate the level of assessed respiration. In some embodiments, a control unit 108 may receive one or more signals 112 from one or more sensors 114 that include information related to a quantity of an agent 214 that flowed through a flow channel 104. In some embodiments, the control unit 108 may then transmit one or more signals 112 that are received by one or more flow indicators 116 that direct the one or more flow indicators 116 to indicate the quantity of the agent 214 that flowed through a flow channel 104. In some embodiments, a control unit 108 may transmit one or more signals 112 that are received by one or more flow indicators 116 that direct the one or more flow indicators 116 to indicate a quantity of an agent 214 that needs to be released from an agent reservoir 212 to reach a predetermined dosage.

In some embodiments, a control unit 108 may receive one or more signals 112 that are transmitted by one or more dose counters 118. For example, in some embodiments, a control unit 108 may receive one or more signals 112 that include information related to the number of doses (or fraction or percentage of a dose) of an agent 214 that have been released from an agent reservoir 212. In some embodiments, a control unit 108 may receive one or more signals 112 that were transmitted by a dose counter 118 that include information related to the number of doses of an agent 214 that are contained in an agent reservoir 212. In some embodiments, a control unit 108 may receive one or more signals 112 that were transmitted by a dose counter 118 that include information related to the quantity of propellant 218 that is contained in a propellant reservoir 216.

In some embodiments, a control unit 108 may compare one or more parameters to one or more threshold levels that are associated with the one or more parameters. For example, in some embodiments, a control unit 108 may receive one or more assessed values from one or more sensors 114 that are associated with a volume of flow through one or more flow channels 104 disposed within an inhaler. The control unit 108 may compare the one or more assessed values to one or more threshold values that are associated with a volume of flow through a flow channel 104 to determine if the one or more assessed values meet or exceed the one or more threshold values. In some embodiments, a control unit 108 may compare one or more assessed values that are related to one or more parameters to one or more ranges of levels associated with the one or more parameters. In some embodiments, a control unit 108 may compare one or more assessed values that are related to one or more parameters to one or more ranges of levels associated with the one or more parameters to determine in the one or more assessed values are within the one or more ranges of levels associated with the one or more parameters.

For example, in some embodiments, a control unit 108 may receive one or more signals 112 transmitted by one or more sensors 114 that include one or more assessed values associated with a volume of flow through one or more flow channels 104 disposed within an inhaler. The control unit 108 may compare the one or more assessed values to one or more ranges of values that are associated with a volume of flow through a flow channel to determine if the one or more assessed values are within the one or more ranges of values. Exemplary ranges of flow through one or more flow channels 104 disposed within an inhaler include, but are not limited to, about 5 liters per minute and about 200 liters per minute, about 30 liters per minute and about 150 liters per minute, about 50 liters per minute and about 100 liters per minute, about 20 liters per minute and about 60 liters per minute, about 30 liters per minute and about 50 liters per minute, about 50 liters per minute and about 200 liters per minute, about 75 liters per minute and about 200 liters per minute, about 100 liters per minute and about 200 liters, about 125 liters per minute and about 200 liters per minute, about 150 liters per minute and about 200 liters per minute, about 175 liters per minute and about 200 liters per minute, about 50 liters per minute and about 150 liters per minute, about 60 liters per minute and about 150 liters per minute, and about 60 liters per minute and about 120 liters per minute.

Numerous threshold values may be assigned to a parameter. In some embodiments, a threshold value may be determined based in the age of a subject using an inhaler. For example, in some embodiments, a threshold value associated with the velocity of flow through a flow channel 104 during an inhalation cycle of a child using an inhaler may be selected to provide for adequate delivery of an agent 214 to the child. In some embodiments, a threshold value associated with the velocity of flow through a flow channel 104 during an inhalation cycle of an adult using an inhaler may be selected to provide for adequate delivery of an agent 214 to the adult. Accordingly, threshold values may be selected with regard to numerous parameters. Examples of such parameters include, but are not limited to, age or weight of a subject, identity of an agent 214 that is to be delivered, location within the respiratory tract where an agent 214 is to be delivered, quantity of an agent 214 that is to be delivered, and the like. Accordingly, a control unit 108 may compare numerous types of parameters to threshold levels that are associated with the one or more parameters. In some embodiments, a threshold value may be selected by a health care provider.

In some embodiments, a control unit 108 may compare a threshold value to a determined value associated with flow through one or more flow channels 104 and then calculate a quantity of propellant 218 to be released to achieve or exceed the threshold value. Accordingly, in some embodiments, a control unit 108 may control one or more actuators 120 that are configured to facilitate at least partial release of propellant 218 from one or more propellant reservoirs 216 to supplement flow through one or more flow channels 104. For example, in some embodiments, flow through one or more flow channels 104 disposed within an inhaler used by a subject may be determined to be below a threshold value needed for effective delivery of an agent 214 to the subject. A control unit 108 may compare the determined flow value to a threshold flow value and then calculate a quantity of propellant 218 for release that will increase flow through the one or more flow channels 104 to meet or exceed the threshold flow value needed for effective delivery of an agent 214 to the subject. Accordingly, in some embodiments, the control unit 108 may then control one or more actuators 120 to facilitate at least partial release of propellant 218 from one or more propellant reservoirs 216 to supplement flow through the one or more flow channels 104 to meet or exceed a threshold flow value. In some embodiments, such supplemental flow may be used to assist in the delivery of one or more agents 214 to a subject having impaired respiratory function. For example, in some embodiments, such supplemental flow may be used to deliver one or more agents 214 to a subject experiencing an asthma attack.

Figure 4:
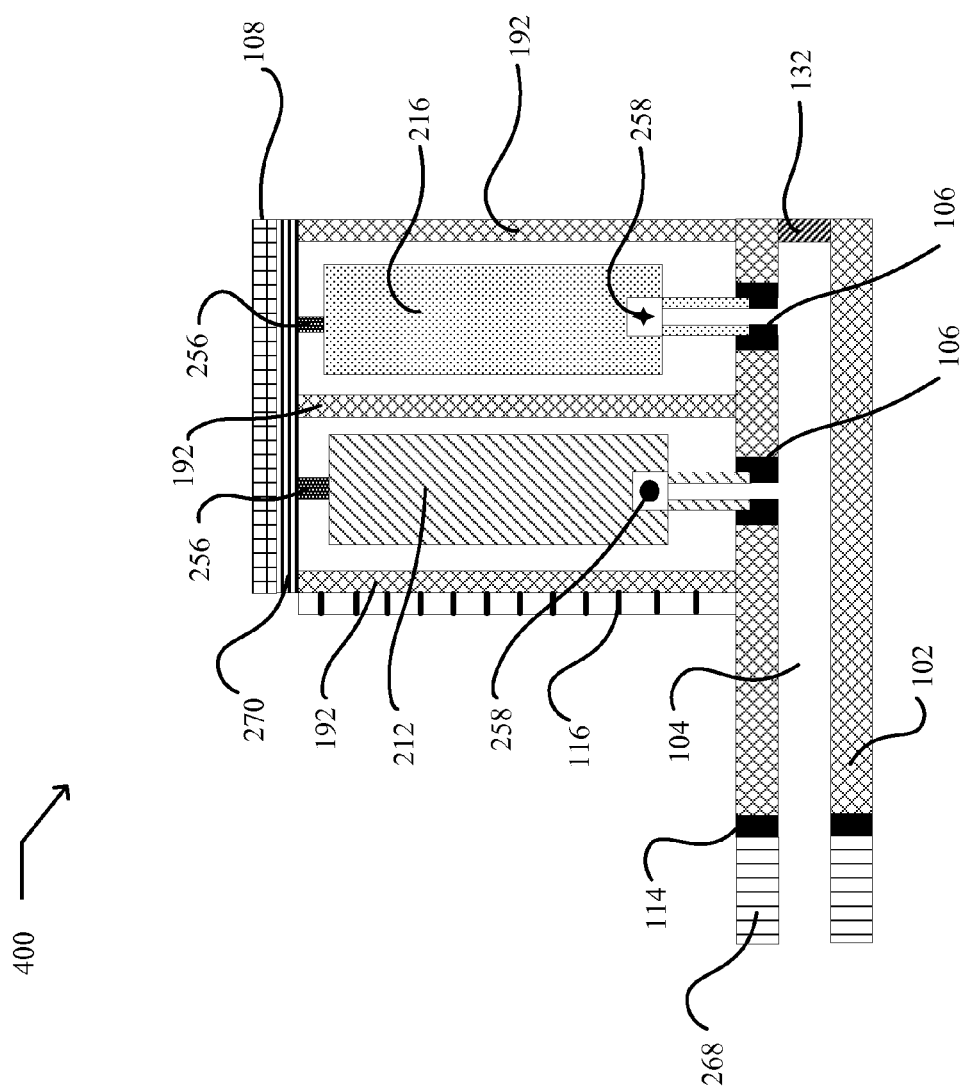
FIG. 4 illustrates a cross-sectional partial side view of an example inhaler 400 in which embodiments may be implemented.

FIG. 4 illustrates a partial cross-sectional side view of system 400 that is configured as an embodiment of an inhaler. System 400 includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 and the propellant reservoir 216 are both configured as aerosol canisters that include a canister body and a valve stem that extends from the canister body into each of the ports 106. The agent reservoir 212 includes a controllable valve 258. The propellant reservoir 216 also includes a controllable valve 258. Both of the controllable valves 258 are illustrated as being closed as indicated by a closed circle and a closed star.

As further shown in FIG. 4, a vacuum sensor 132 is operably coupled to the flow channel 104 and configured to detect pressure that is applied to the flow channel 104. An aerosol canister content release mechanism 270 is illustrated with a pushrod actuator 256 operably coupled with each of the agent reservoir 212 and the propellant reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the agent reservoir 212 and the propellant reservoir 216. The control unit 108 is operably coupled with the vacuum sensor 132. Accordingly, in some embodiments, the control unit 108 may be configured to facilitate at least partial release from one or both of the agent reservoir 212 and the propellant reservoir 216 during an inhalation cycle when a vacuum is applied to the inhaler by a subject (e.g. suction by a mouth of the subject). In some embodiments, the control unit 108 may be configured to halt at least partial release from one or both of the agent reservoir 212 and the propellant reservoir 216 during an exhalation cycle. In some embodiments, the control unit 108 may be configured to facilitate at least partial release from an agent reservoir 212 and then facilitate at least partial release from a propellant reservoir 216. In some embodiments, the control unit 108 may be configured to facilitate at least partial release from both the agent reservoir 212 and from the propellant reservoir 216 at substantially the same time. In some embodiments, sensor 114 may be configured to detect a quantity of an agent 214 that flows through the flow channel 104 during use of the inhaler by a subject. Accordingly, in some embodiments, such information may be transmitted to the control unit 108 that may use the information to calculate a quantity of agent 214 that needs to be administered to the subject to reach a predetermined dosage. The control unit 108 may then control operation of the aerosol canister content release mechanism 270 to administer an additional quantity of agent 214 to reach the predetermined dosage. A flow indicator 116 is illustrated as showing a lack of flow through the flow channel 104 disposed within the inhaler.

Figure 4A:
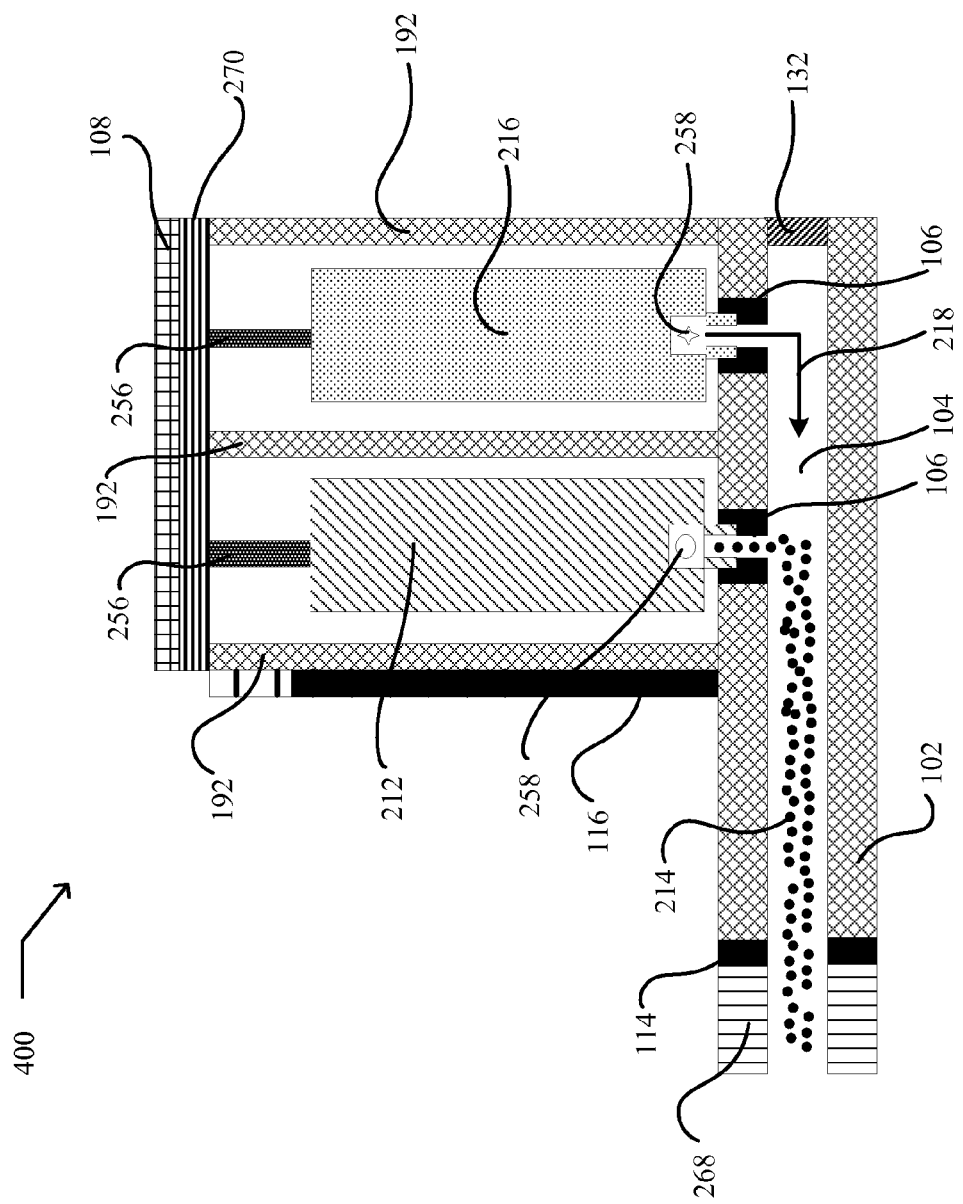
FIG. 4A illustrates a cross-sectional partial side view of an example inhaler 400 in which embodiments may be implemented.

FIG. 4A illustrates a partial cross-sectional side view of system 400 that is configured as an embodiment of an inhaler that is illustrated as being activated to at least partially release an agent 214 from the agent reservoir 212 and propellant 218 from the propellant reservoir 216. System 400 is shown as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 and the propellant reservoir 216 are both configured as aerosol canisters that include a canister body and a valve stem that extends from the canister body into each of the ports 106. The agent reservoir 212 includes a controllable valve 258. The propellant reservoir 216 also includes a controllable valve 258. The controllable valves 258 that are operably coupled to the agent reservoir 212 and the propellant reservoir 216 are illustrated as being open as indicated by an open circle and an open star. Flow through the flow channel 104 is illustrated by an arrow indicating right to left flow of propellant 218 toward the mouthpiece 268 through the flow channel 104.

An aerosol canister content release mechanism 270 is illustrated with a pushrod actuator 256 operably coupled with each of the agent reservoir 212 and the propellant reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the agent reservoir 212 and the propellant reservoir 216. The control unit 108 is operably coupled with sensor 114. The pushrod actuators 256 that are operably associated with the agent reservoir 212 and the propellant reservoir 216 are illustrated as being in an activated state. In the activated state, the pushrod actuators 256 compress the canister bodies of the agent reservoir 212 and the propellant reservoir 216 that are configured as aerosol canisters toward the valve stems that extend from the canister bodies to facilitate at least partial release of agent 214 from the agent reservoir 212 and propellant 218 from the propellant reservoir 216 through ports 106 and into the flow channel 104. A flow indicator 116 is illustrated as showing a high level of flow through the flow channel 104 disposed within the inhaler.

Figure 5:
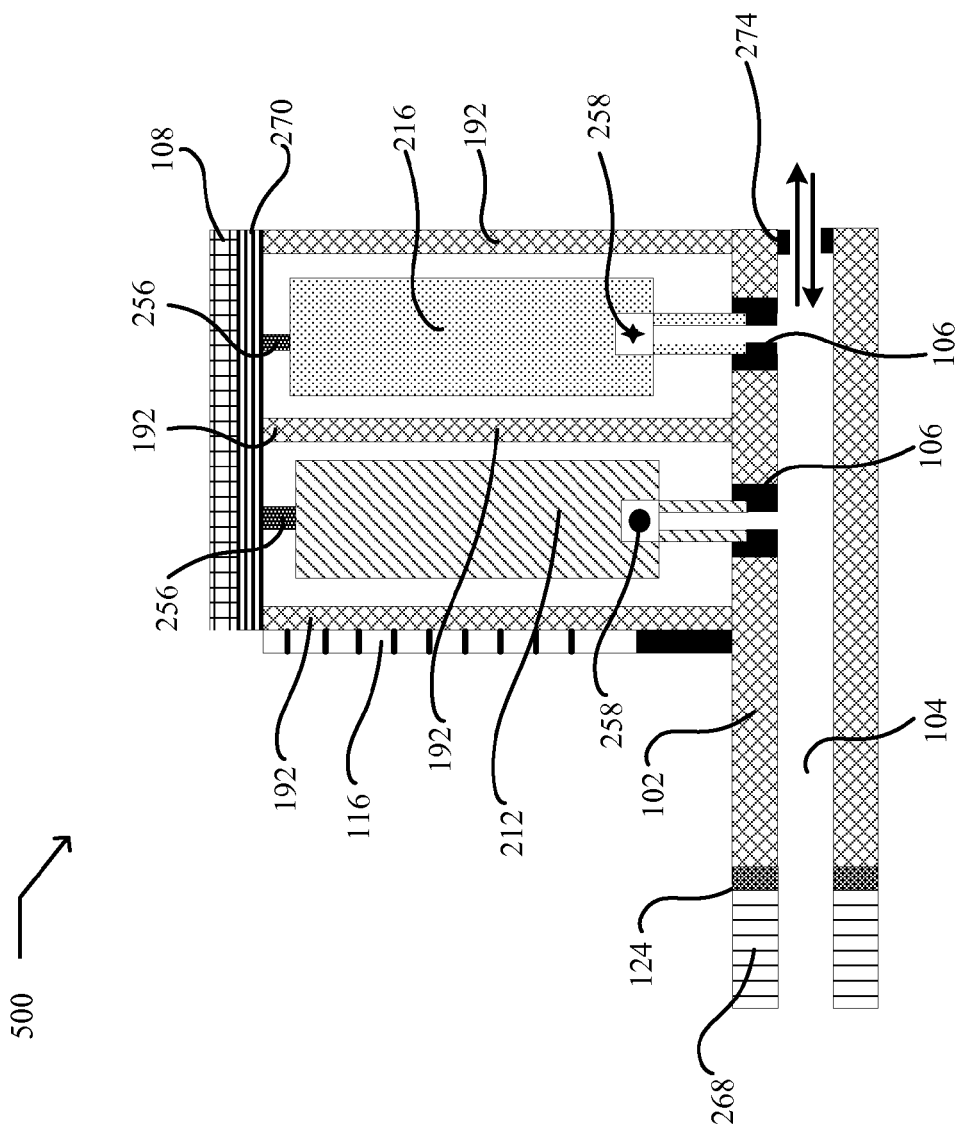
FIG. 5 illustrates a cross-sectional partial side view of an example inhaler 500 in which embodiments may be implemented.

FIG. 5 illustrates a partial cross-sectional side view of system 500 that is configured as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 and the propellant reservoir 216 are both configured as aerosol canisters that include a canister body and a valve stem that extends from the canister body into each of the ports 106. The agent reservoir 212 includes a controllable valve 258. The propellant reservoir 216 also includes a controllable valve 258.

In FIG. 5, the controllable valve 258 that is operably coupled to the agent reservoir 212 is illustrated as being closed as indicated by a closed circle. The controllable valve 258 that is operably coupled to the propellant reservoir 216 is illustrated as being closed as indicated by a closed star. Flow through the flow channel 104 is illustrated by two arrows pointing in opposite directions indicating bidirectional flow through the flow channel 104. A flow sensor 124 is operably coupled to the flow channel 104 and configured to detect flow through the flow channel 104. An aerosol canister content release mechanism 270 is illustrated with a pushrod actuator 256 operably coupled with each of the agent reservoir 212 and the propellant reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the agent reservoir 212 and the propellant reservoir 216. The control unit 108 is operably coupled with flow sensor 124. A flow indicator 116 is illustrated as showing a moderate level of flow through the flow channel 104 disposed within the inhaler. A controllable flow valve 274 is illustrated as being in an open state to allow flow through the flow channel 104 disposed within the inhaler. The controllable flow valve 274 is operably coupled with control unit 108.

Figure 5A:
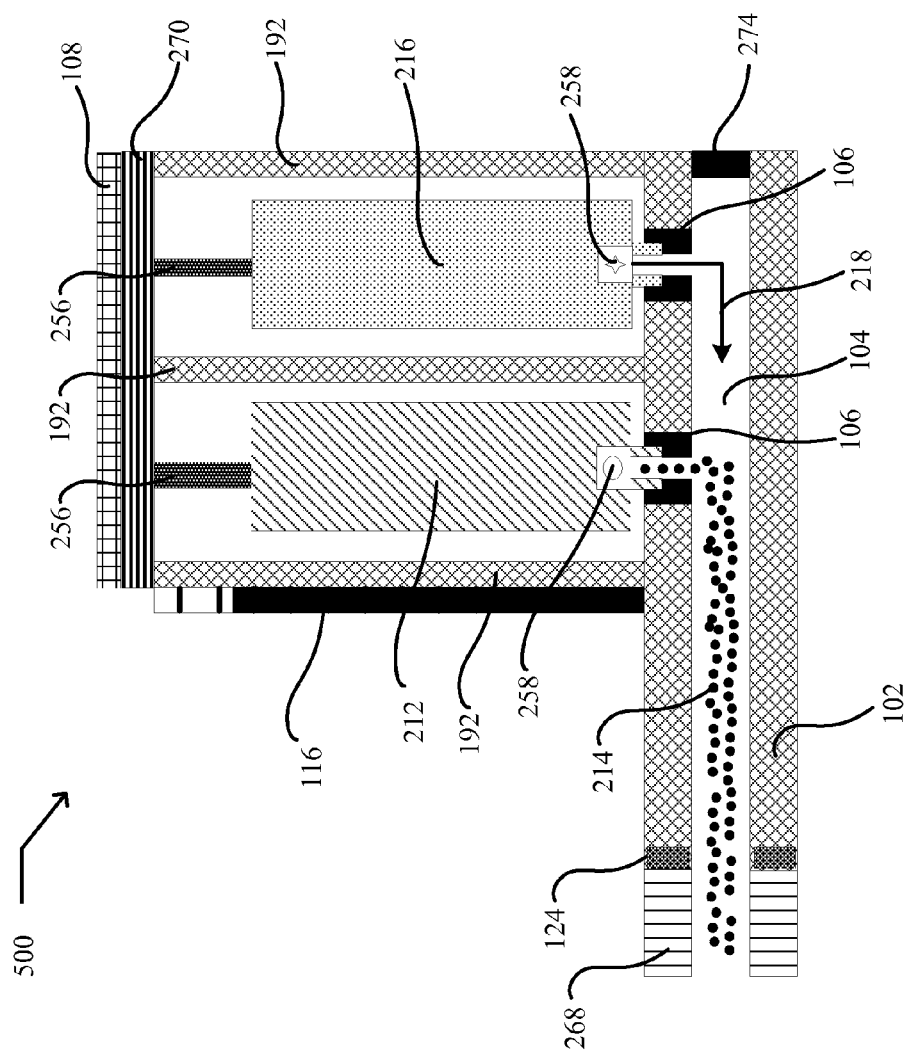
FIG. 5A illustrates a cross-sectional partial side view of an example inhaler 500 in which embodiments may be implemented.

FIG. 5A illustrates a partial cross-sectional side view of system 500 that is configured as an embodiment of an inhaler in an activated state to release an agent 214 from an agent reservoir 212 and propellant 218 from a propellant reservoir 216. The inhaler includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 and the propellant reservoir 216 are both configured as aerosol canisters that include a canister body and a valve stem that extends from the canister body into each of the ports 106. The agent reservoir 212 includes a controllable valve 258. The propellant reservoir 216 also includes a controllable valve 258.

In FIG. 5A, the controllable valve 258 that is operably coupled to the agent reservoir 212 is illustrated as being open as indicated by an open circle. The controllable valve 258 that is operably coupled to the propellant reservoir 216 is illustrated as being open as indicated by an open star. Flow of propellant 218 through the flow channel 104 is illustrated by an arrow pointing from right to left through the flow channel 104 toward the mouthpiece 268. A flow sensor 124 is operably coupled to the flow channel 104 and configured to detect flow through the flow channel 104. An aerosol canister content release mechanism 270 is illustrated with a pushrod actuator 256 operably coupled with each of the agent reservoir 212 and the propellant reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the agent reservoir 212 and the propellant reservoir 216. The control unit 108 is operably coupled with flow sensor 124. A flow indicator 116 is illustrated as showing a high level of flow through the flow channel 104 disposed within the inhaler. A controllable flow valve 274 is illustrated as being in a closed state to direct flow of agent 214 and propellant 218 through the flow channel 104 disposed within the inhaler toward the mouthpiece 268. In some embodiments, the controllable flow valve 274 may be operably coupled with a control unit 108. In some embodiments, the controllable flow valve 274 may be operably coupled with sensor 124. In some embodiments, the controllable flow valve 274 may be operably coupled with control unit 108 and sensor 124.

Figure 6:
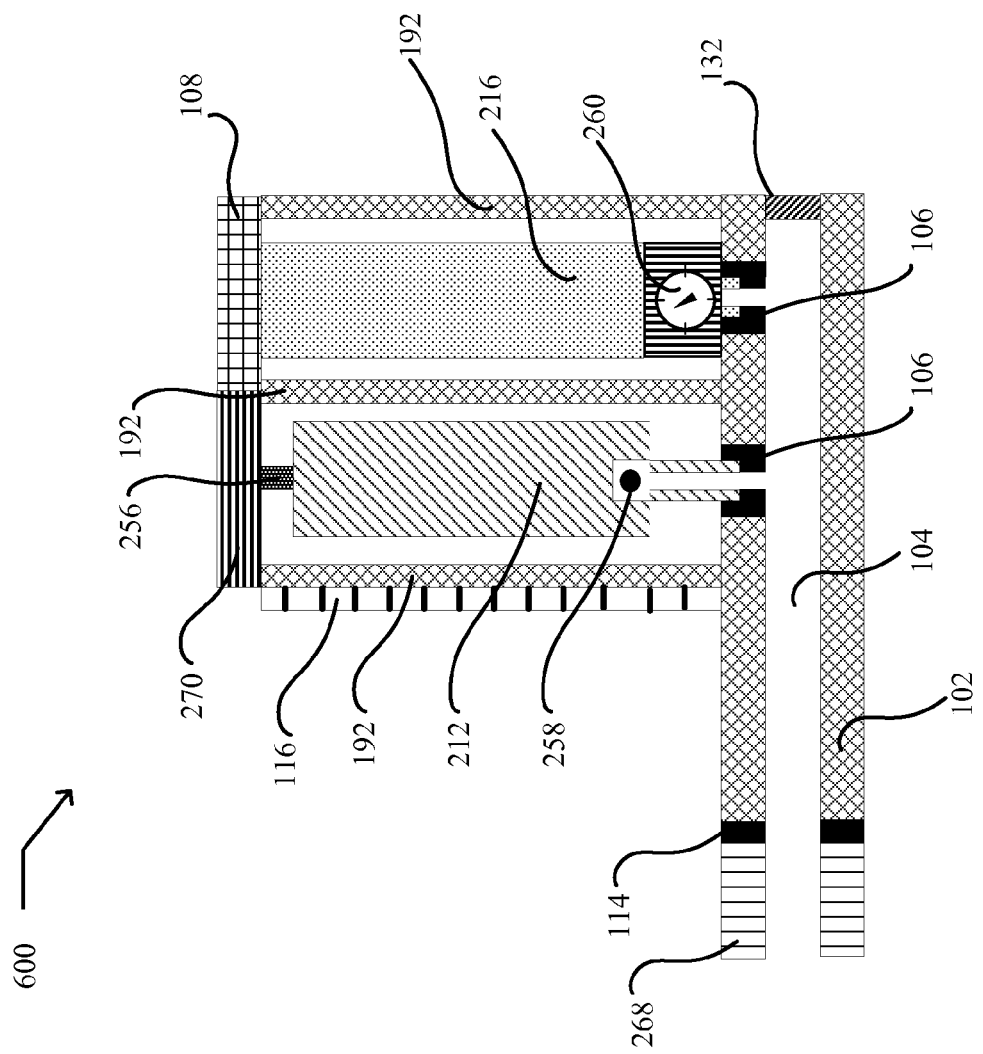
FIG. 6 illustrates a cross-sectional partial side view of an example inhaler 600 in which embodiments may be implemented.

FIG. 6 illustrates a partial cross-sectional side view of system 600. System 600 is shown as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 is configured as an aerosol canister that includes a canister body and a valve stem that extends from the canister body into port 106. The agent reservoir 212 includes a controllable valve 258. The controllable valve 258 that is operably coupled with the agent reservoir is illustrated as being closed as indicated by a closed circle. The propellant reservoir 216 is configured as a compressed gas cylinder that is operably coupled to a regulator 260. In some embodiments, the regulator 260 may be operably coupled with control unit 108. In some embodiments, the regulator 260 may be operably coupled with vacuum sensor 134. In some embodiments, the regulator 260 may be operably coupled with control unit 108 and vacuum sensor 134.

Accordingly, in some embodiments, control unit 108 may control operation of regulator 260 to facilitate at least partial release of propellant 218 from propellant reservoir 216. In some embodiments, control unit 108 may control operation of regulator 260 to facilitate at least partial release of propellant 218 from propellant reservoir 216 in response to vacuum applied to a flow channel 104 disposed within the inhaler by a subject using the inhaler (e.g. during inhalation). An aerosol canister content release mechanism 270 is illustrated with a pushrod actuator 256 operably coupled with the agent reservoir 212. The aerosol canister content release mechanism 270 is operably coupled with a control unit 108. The control unit 108 is configured to direct operation of the aerosol canister content release mechanism 270 to control the pushrod actuator 256 to facilitate at least partial release from the agent reservoir 212. The control unit 108 is operably coupled with the vacuum sensor 132. Accordingly, in some embodiments, the control unit 108 may be configured to facilitate at least partial release from one or both of the agent reservoir 212 and the propellant reservoir 216 during an inhalation cycle when a vacuum is applied to the inhaler by a subject. In some embodiments, the control unit 108 may be configured to halt at least partial release from one or both of the agent reservoir 212 and the propellant reservoir 216 during an exhalation cycle. In some embodiments, the control unit 108 may be configured to facilitate at least partial release from an agent reservoir 212 and then facilitate at least partial release from a propellant reservoir 216. In some embodiments, the control unit 108 may be configured to facilitate at least partial release from both the agent reservoir 212 and from the propellant reservoir 216 at substantially the same time.

In some embodiments, sensor 114 may be configured to detect a quantity of an agent 214 that flows through the flow channel 104 during use of the inhaler by a subject. Accordingly, in some embodiments, such information may be transmitted to the control unit 108 that may use the information to calculate a quantity of agent 214 that needs to be administered to the subject to reach a predetermined dosage. The control unit 108 may then control operation of the aerosol canister content release mechanism 270 to administer an additional quantity of agent 214 to reach the predetermined dosage. A flow indicator 116 is illustrated as showing a lack of flow through the flow channel 104 disposed within the inhaler.

Figure 6A:
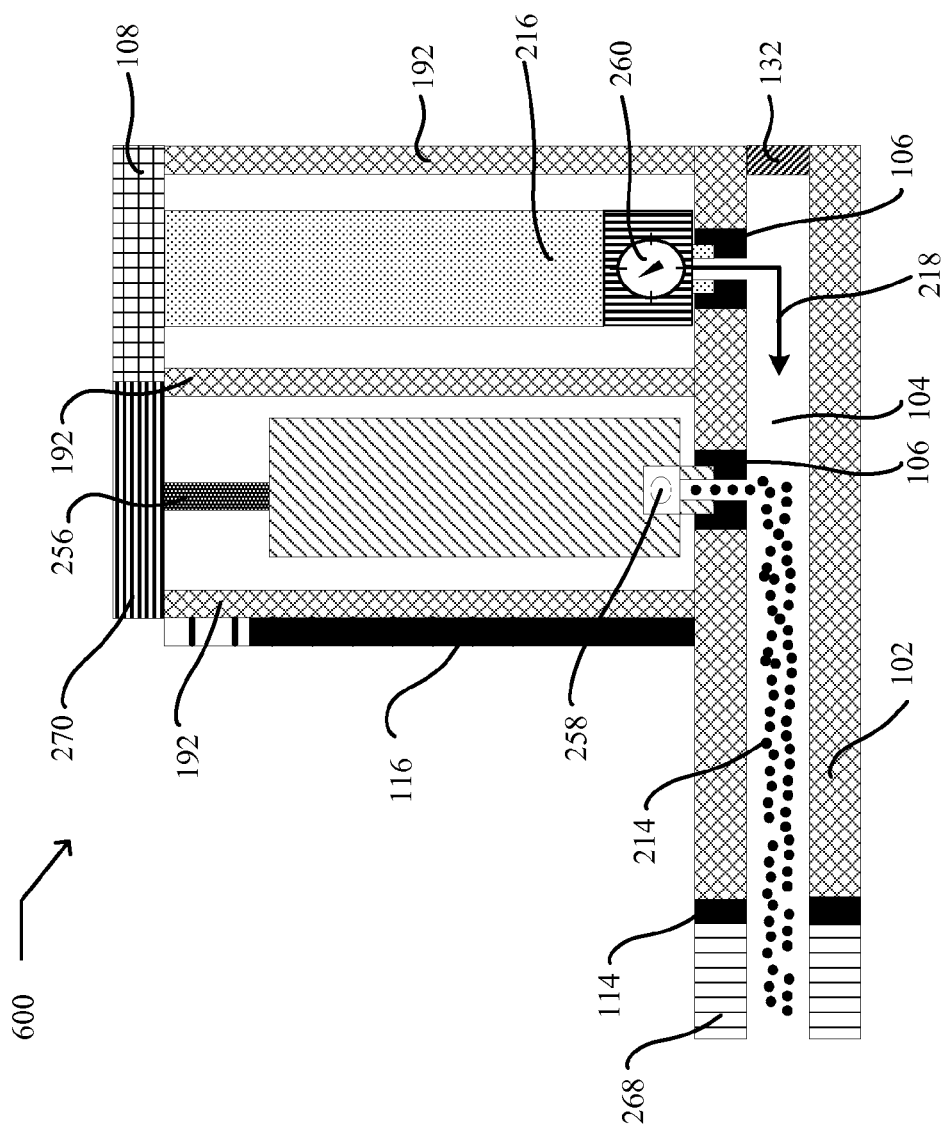
FIG. 6A illustrates a cross-sectional partial side view of an example inhaler 600 in which embodiments may be implemented.

FIG. 6A illustrates a partial cross-sectional side view of system 600. System 600 is shown as an embodiment of an inhaler in an activated state to release an agent 214 and propellant 218. The inhaler includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 is configured as an aerosol canister that includes a canister body and a valve stem that extends from the canister body into port 106. The agent reservoir 212 includes a controllable valve 258. The controllable valve 258 that is operably coupled with the agent reservoir is illustrated as being open as indicated by an open circle. The propellant reservoir 216 is configured as a compressed gas cylinder that is operably coupled to a regulator 260. The propellant reservoir 216 is illustrated as at least partially releasing propellant 218 that flows from right to left toward the mouthpiece 268 as indicated by the arrow. In some embodiments, the regulator 260 may be operably coupled with control unit 108. In some embodiments, the regulator 260 may be operably coupled with vacuum (or pressure) sensor 134. In some embodiments, the regulator 260 may be operably coupled with control unit 108 and vacuum sensor 134. Accordingly, in some embodiments, control unit 108 may control operation of regulator 260 to facilitate at least partial release of propellant 218 from propellant reservoir 216. In some embodiments, control unit 108 may control operation of regulator 260 to facilitate at least partial release of propellant 218 from propellant reservoir 216 in response to vacuum (or reduced pressure) applied to a flow channel 104 disposed within the inhaler by a subject using the inhaler.

An aerosol canister content release mechanism 270 is illustrated with a pushrod actuator 256 operably coupled with the agent reservoir 212. The pushrod actuator 256 is illustrated as depressing the aerosol canister to at least partially release the agent 214. The aerosol canister content release mechanism 270 is operably coupled with a control unit 108. The control unit 108 is configured to direct operation of the aerosol canister content release mechanism 270 to control the pushrod actuator 256 to facilitate at least partial release from the agent reservoir 212. The control unit 108 is operably coupled with the vacuum sensor 132. Accordingly, in some embodiments, the control unit 108 may be configured to facilitate at least partial release from one or both of the agent reservoir 212 and the propellant reservoir 216 during an inhalation cycle when a vacuum is applied to the inhaler by a subject. In some embodiments, the control unit 108 may be configured to halt at least partial release from one or both of the agent reservoir 212 and the propellant reservoir 216 during an exhalation cycle.

In some embodiments, the control unit 108 may be configured to facilitate at least partial release from an agent reservoir 212 and then facilitate at least partial release from a propellant reservoir 216. In some embodiments, the control unit 108 may be configured to facilitate at least partial release from both the agent reservoir 212 and from the propellant reservoir 216 at substantially the same time. In some embodiments, sensor 114 may be configured to detect a quantity of an agent 214 that flows through the flow channel 104 during use of the inhaler by a subject. Accordingly, in some embodiments, such information may be transmitted to the control unit 108 that may use the information to calculate a quantity of agent 214 that needs to be administered to the subject to reach a predetermined dosage. The control unit 108 may then control operation of the aerosol canister content release mechanism 270 to administer an additional quantity of agent 214 to reach the predetermined dosage. A flow indicator 116 is illustrated as showing a high level of flow through the flow channel 104 disposed within the inhaler.

Figure 7A:
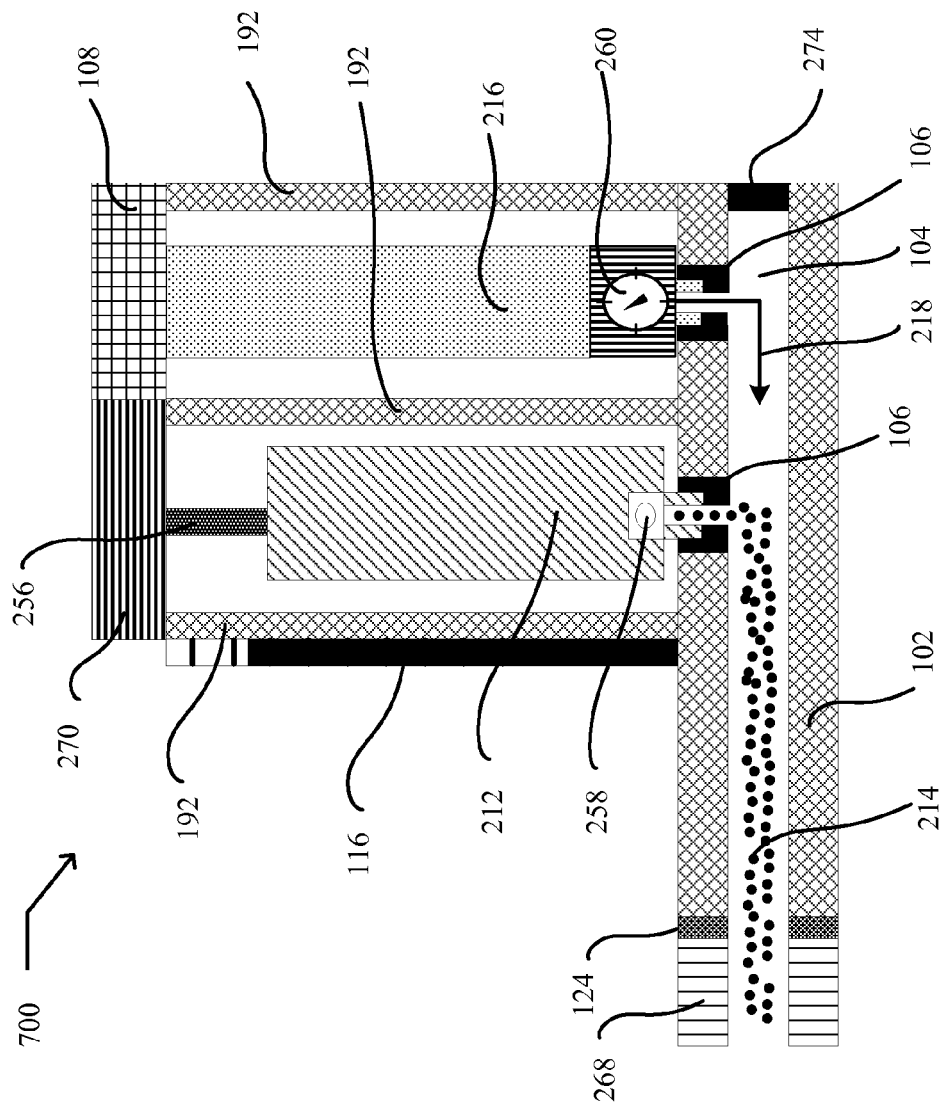
FIG. 7A illustrates a cross-sectional partial side view of an example inhaler 700 in which embodiments may be implemented.
Figure 8:
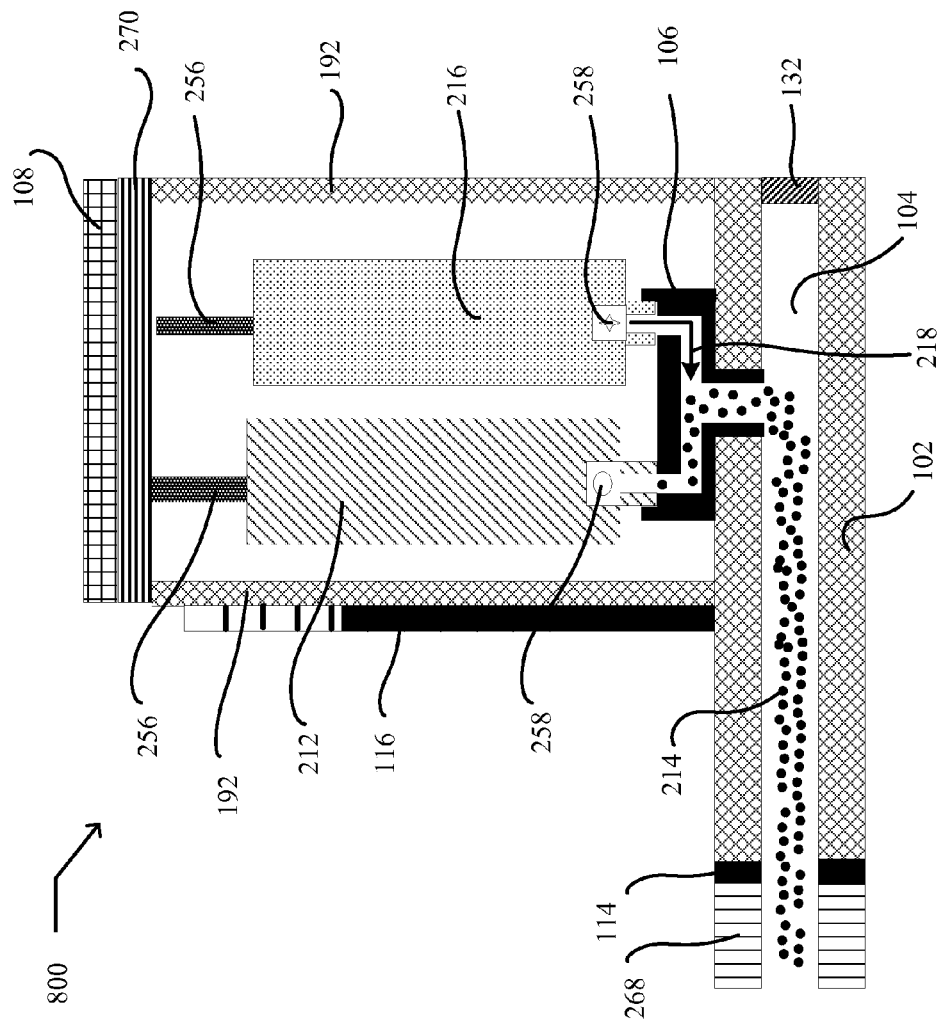
FIG. 8 illustrates a cross-sectional partial side view of an example inhaler 800 in which embodiments may be implemented.
Figure 9:
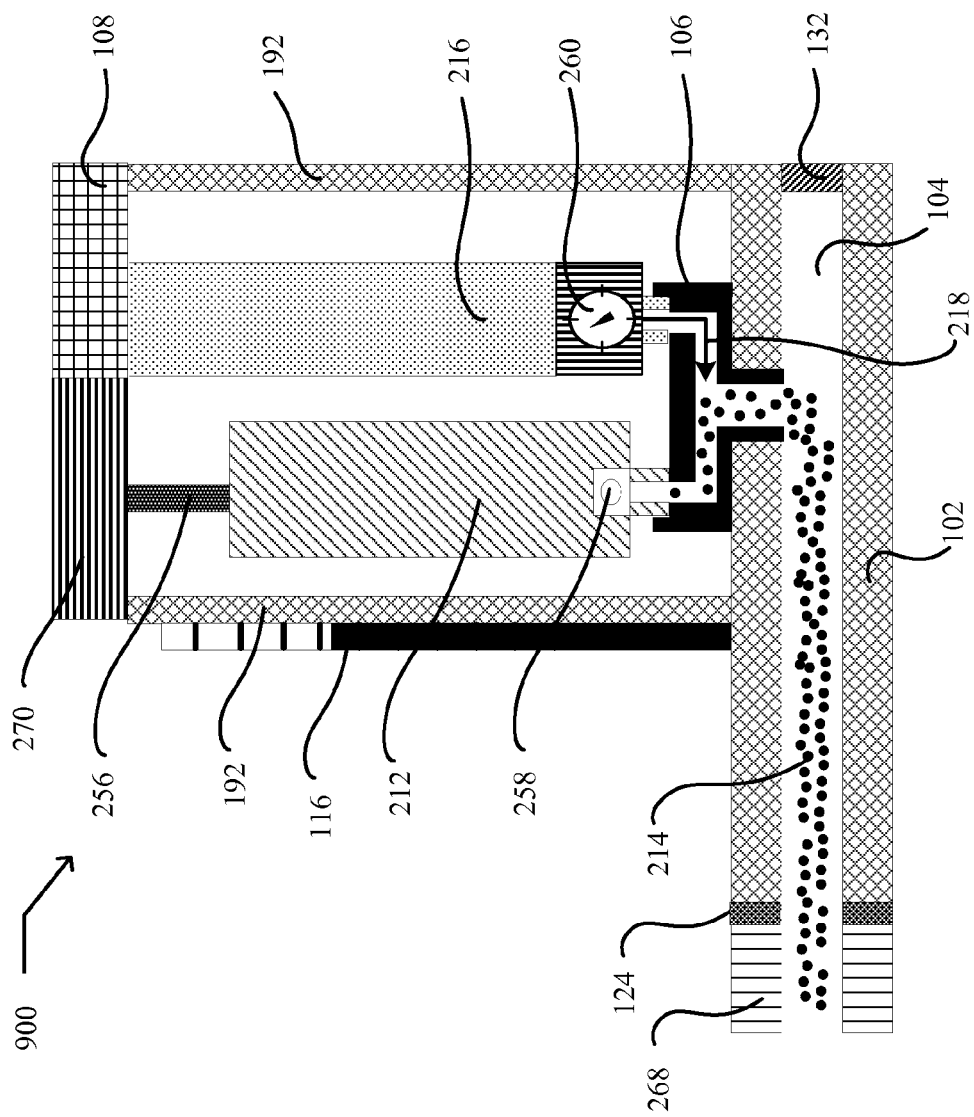
FIG. 9 illustrates a cross-sectional partial side view of an example inhaler 900 in which embodiments may be implemented.

FIG. 7 illustrates a partial cross-sectional side view of system 700 that is configured as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 is configured as aerosol canister that includes a canister body and a valve stem that extends from the canister body into a port 106. The agent reservoir 212 includes a controllable valve 258. The controllable valve 258 that is operably coupled to the agent reservoir 212 is illustrated as being closed as indicated by a closed circle. The propellant reservoir 216 is configured as a compressed gas cylinder that is operably coupled to a regulator 260. In some embodiments, the regulator 260 may be operably coupled with control unit 108. In some embodiments, the regulator 260 may be operably coupled with flow sensor 124. In some embodiments, the regulator 260 may be operably coupled with control unit 108 and flow sensor 124.

Accordingly, in some embodiments, control unit 108 may control operation of regulator 260 to facilitate at least partial release of propellant 218 from propellant reservoir 216. In some embodiments, control unit 108 may control operation of regulator 260 to facilitate at least partial release of propellant 218 from propellant reservoir 216 in response to flow through flow channel 104 disposed within the inhaler during use of the inhaler by a subject. Flow through the flow channel 104 is illustrated by two arrows pointing in opposite directions indicating bidirectional flow through flow channel 104. A flow sensor 124 is operably coupled to flow channel

104 and configured to detect flow through the flow channel 104. An aerosol canister content release mechanism 270 is illustrated with a pushrod actuator 256 operably coupled with the agent reservoir 212. The aerosol canister content release mechanism 270 is operably coupled with a control unit 108. The control unit 108 is configured to direct operation of the aerosol canister content release mechanism 270 to control the pushrod actuator 256 to facilitate at least partial release from the agent reservoir 212. The control unit 108 is operably coupled with flow sensor 124. A flow indicator 116 is illustrated as showing a moderate level of flow through the flow channel 104 disposed within the inhaler. A controllable flow valve 274 is illustrated as being in an open state to allow flow through the flow channel 104 disposed within the inhaler. The controllable flow valve 274 is operably coupled with control unit 108.

FIG. 7A illustrates a partial cross-sectional side view of system 700 that is configured as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 is configured as aerosol canister that includes a canister body and a valve stem that extends from the canister body into a port 106. The agent reservoir 212 includes a controllable valve 258. The controllable valve 258 that is operably coupled to the agent reservoir 212 is illustrated as being open as indicated by an open circle. The propellant reservoir 216 is configured as a compressed gas cylinder that is operably coupled to a regulator 260.

In some embodiments, the regulator 260 may be operably coupled with control unit 108. In some embodiments, the regulator 260 may be operably coupled with flow sensor 124. In some embodiments, the regulator 260 may be operably coupled with control unit 108 and flow sensor 124. Accordingly, in some embodiments, control unit 108 may control operation of regulator 260 to facilitate at least partial release of propellant 218 from propellant reservoir 216. In some embodiments, control unit 108 may control operation of regulator 260 to facilitate at least partial release of propellant 218 from propellant reservoir 216 in response to flow through flow channel 104 disposed within the inhaler during use of the inhaler by a subject. Flow through the flow channel 104 is illustrated by an arrow pointing from right to left indicating flow of propellant 218 through the flow channel 104 toward the mouthpiece 268. A flow sensor 124 is operably coupled to the flow channel 104 and configured to detect flow through the flow channel 104.

As further shown in FIG. 7A, an aerosol canister content release mechanism 270 is illustrated with a pushrod actuator 256 operably coupled with the agent reservoir 212. The aerosol canister content release mechanism 270 is operably coupled with a control unit 108. The control unit 108 is configured to direct operation of the aerosol canister content release mechanism 270 to control the pushrod actuator 256 to facilitate at least partial release from the agent reservoir 212. The control unit 108 is operably coupled with flow sensor 124. A flow indicator 116 is illustrated as showing a high level of flow through the flow channel 104 disposed within the inhaler. A controllable flow valve 274 is illustrated as being in a closed state to direct flow through the flow channel 104 disposed within the inhaler toward the mouthpiece 268. The controllable flow valve 274 is operably coupled with control unit 108.

FIG. 8 illustrates a partial cross-sectional side view of system 800 that is configured as an embodiment of an inhaler that is illustrated as being activated to at least partially release an agent 214 from the agent reservoir 212 and propellant 218 from the propellant reservoir 216. System 800 is shown as an embodiment of an inhaler that includes a housing 102 having a flow channel 104 disposed therein. Also illustrated is a port 106 disposed in the housing 102 in fluid communication with the flow channel 104. An agent reservoir 212 and a propellant reservoir 216 are illustrated as being operably coupled to the port 106. The agent reservoir 212 and the propellant reservoir 216 are illustrated as being held within a reservoir support 192. The agent reservoir 212 and the propellant reservoir 216 are both configured as aerosol canisters that include a canister body and a valve stem that extends from the canister body into the port 106. The agent reservoir 212 includes a controllable valve 258. The propellant reservoir 216 also includes a controllable valve 258. The controllable valves 258 that are operably coupled to the agent reservoir 212 and the propellant reservoir 216 are illustrated as being open as indicated by an open circle and an open star. Flow through the flow channel 104 is illustrated by an arrow indicating right to left flow of propellant 218 toward the mouthpiece 268 through the flow channel 104. An aerosol canister content release mechanism 270 is illustrated with a pushrod actuator 256 operably coupled with each of the agent reservoir 212 and the propellant reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the agent reservoir 212 and the propellant reservoir 216. The control unit 108 is operably coupled with sensor 114.

In FIG. 8, the pushrod actuators 256 that are operably associated with the agent reservoir 212 and the propellant reservoir 216 are illustrated as being in an activated state. In the activated state, the pushrod actuators 256 compress the canister bodies of the agent reservoir 212 and the propellant reservoir 216 that are configured as aerosol canisters toward the valve stems that extend from the canister bodies to facilitate at least partial release of agent 214 from the agent reservoir 212 and propellant 218 from the propellant reservoir 216 through port 106 and into the flow channel 104. A flow indicator 116 is illustrated as showing a high level of flow through the flow channel 104 disposed within the inhaler. A vacuum (or pressure) sensor 132 in operably coupled with the flow channel 104 disposed within the housing 102. The control unit 108 is operably coupled with the vacuum sensor 132. Accordingly, in some embodiments, the control unit 108 may be configured to facilitate at least partial release from one or both of the agent reservoir 212 and the propellant reservoir 216 during an inhalation cycle when a vacuum is applied to the inhaler by a subject. In some embodiments, the control unit 108 may be configured to halt at least partial release from one or both of the agent reservoir 212 and the propellant reservoir 216 during an exhalation cycle.

FIG. 9 illustrates a partial cross-sectional side view of system 900 that is configured as an embodiment of an inhaler that is illustrated as being activated to at least partially release an agent 214 from the agent reservoir 212 and propellant 218 from the propellant reservoir 216. System 900 is shown as an embodiment of an inhaler that includes a housing 102 having a flow channel 104 disposed therein. Also illustrated is a port 106 disposed in the housing 102 in fluid communication with the flow channel 104. An agent reservoir 212 and a propellant reservoir 216 are illustrated as being operably coupled to the port 106. The agent reservoir 212 and the propellant reservoir 216 are illustrated as being held within a reservoir support 192. The agent reservoir 212 is configured as an aerosol canister that includes a canister body and a valve stem that extends from the canister body into the port 106. The agent reservoir 212 includes a controllable valve 258. The controllable valve 258 that is operably coupled to the agent reservoir 212 is illustrated as being open as indicated by an open circle. The propellant reservoir 216 is configured as a compressed gas cylinder that is operably coupled to a regulator 260. In some embodiments, the regulator 260 may be operably coupled with control unit 108. In some embodiments, the regulator 260 may be operably coupled with a vacuum sensor 132. In some embodiments, the regulator 260 may be operably coupled with control unit 108 and vacuum sensor 134.

Accordingly, in some embodiments, control unit 108 may control operation of regulator 260 to facilitate at least partial release of propellant 218 from propellant reservoir 216. In some embodiments, control unit 108 may control operation of regulator 260 to facilitate at least partial release of propellant 218 from propellant reservoir 216 in response to vacuum applied to a flow channel 104 disposed within the inhaler during use of the inhaler by a subject. Flow through the flow channel 104 is illustrated by an arrow pointing from right to left indicating flow of propellant 218 through the flow channel 104 toward the mouthpiece 268. A flow sensor 124 is operably coupled to the flow channel 104 and configured to detect flow through the flow channel 104. An aerosol canister content release mechanism 270 is illustrated with a pushrod actuator 256 operably coupled with the agent reservoir 212. The aerosol canister content release mechanism 270 is operably coupled with a control unit 108. The control unit 108 is configured to direct operation of the aerosol canister content release mechanism 270 to control the pushrod actuator 256 to facilitate at least partial release from the agent reservoir 212. The control unit 108 is operably coupled with flow sensor 124. A flow indicator 116 is illustrated as showing a high level of flow through the flow channel 104 disposed within the inhaler.

Figure 10:
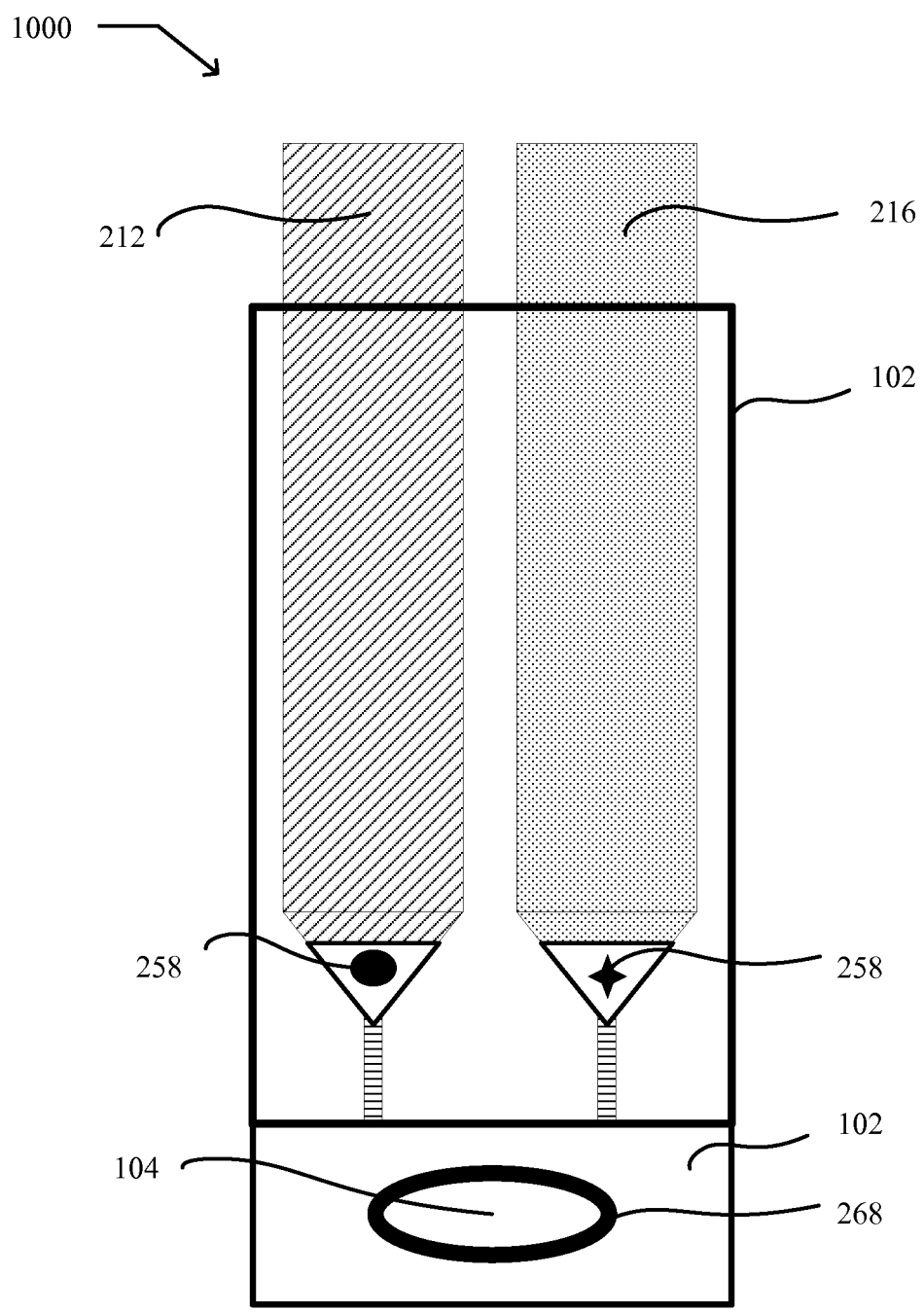
FIG. 10 illustrates a cross-sectional partial front view of an example inhaler 1000 in which embodiments may be implemented.

FIG. 10 illustrates a partial cross-sectional front view of system 1000. System 1000 is shown as an embodiment of a metered dose inhaler that includes a housing 102 having a flow channel 104 disposed therein. A mouthpiece 268 is operably coupled with the housing 102. An agent reservoir 212 and a propellant reservoir 216 are each operably coupled with a port 106 (not shown) in fluid communication with the flow channel 104. The agent reservoir 212 and the propellant reservoir 216 are both configured as aerosol canisters that include a canister body and a valve stem that extends from the canister body into port 106 (not shown). The agent reservoir 212 includes a controllable valve 258. The propellant reservoir 216 also includes a controllable valve 258. In FIG. 10, the controllable valves 258 that are operably coupled to the agent reservoir 212 and the propellant reservoir 216 are illustrated as being closed as indicated by a closed circle and a closed star.

Figure 10A:
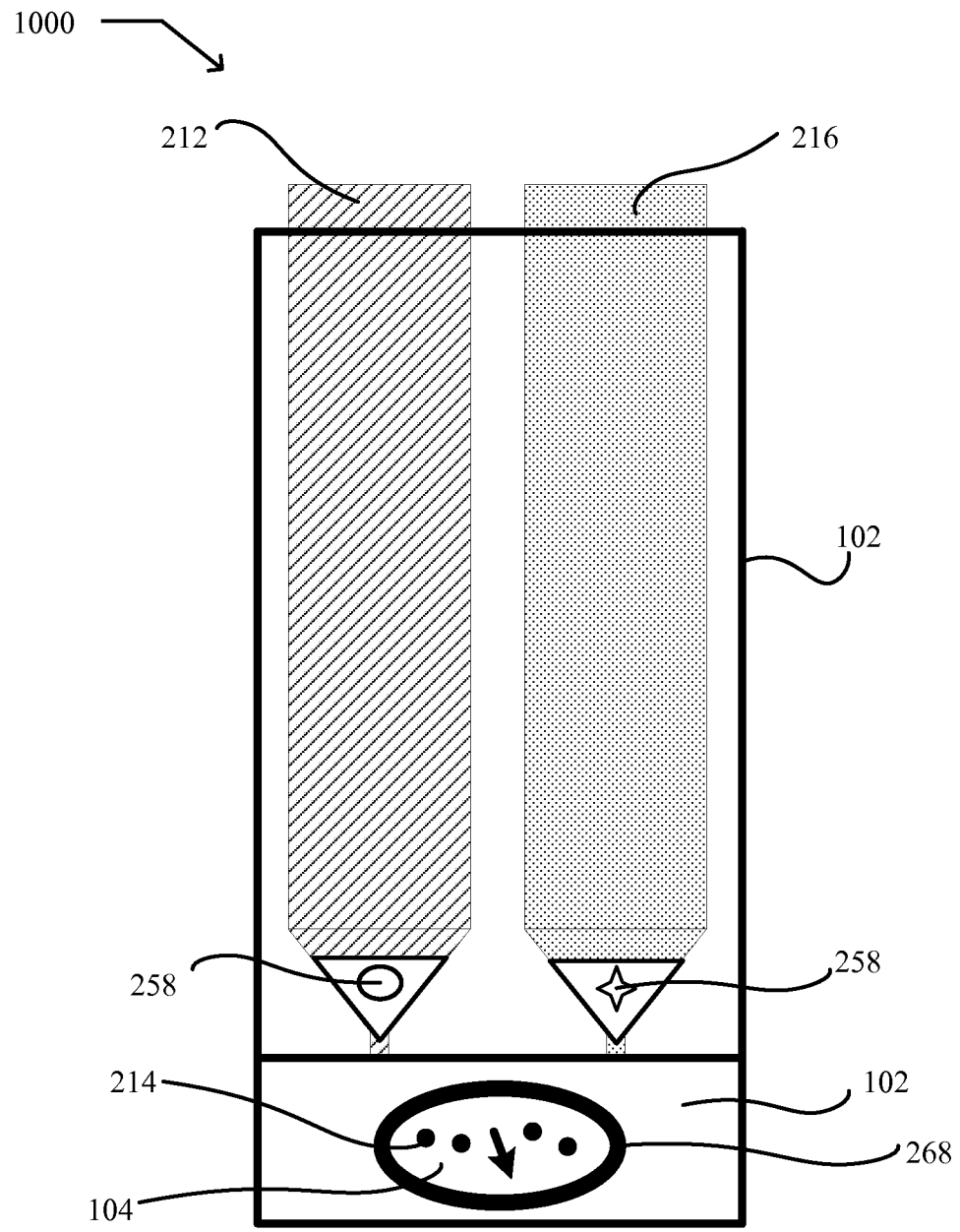
FIG. 10A illustrates a cross-sectional partial front view of an example inhaler 1000 in which embodiments may be implemented.

FIG. 10A illustrates a partial cross-sectional front view of system 1000. System 1000 is shown as an embodiment of a metered dose inhaler that includes a housing 102 having an flow channel 104 disposed therein. A mouthpiece 268 is operably coupled with the housing 102. An agent reservoir 212 and a propellant reservoir 216 are each operably coupled with a port 106 (not shown) in fluid communication with the flow channel 104. The agent reservoir 212 and the propellant reservoir 216 are both configured as aerosol canisters that include a canister body and a valve stem that extends from the canister body into port 106 (not shown). The agent reservoir 212 includes a controllable valve 258. The propellant reservoir 216 also includes a controllable valve 258. The controllable valves 258 that are operably coupled to the agent reservoir 212 and the propellant reservoir 216 are illustrated as being open as indicated by an open circle and an open star. Agent 214 is illustrated as flowing through the flow channel 102 disposed within the housing 102 as indicated by the arrow. System 1000 is configured as a metered dose inhaler that provides agent 214 released from an agent reservoir 212 and supplemental propellant 218 from a propellant reservoir 216.

Figure 10B:
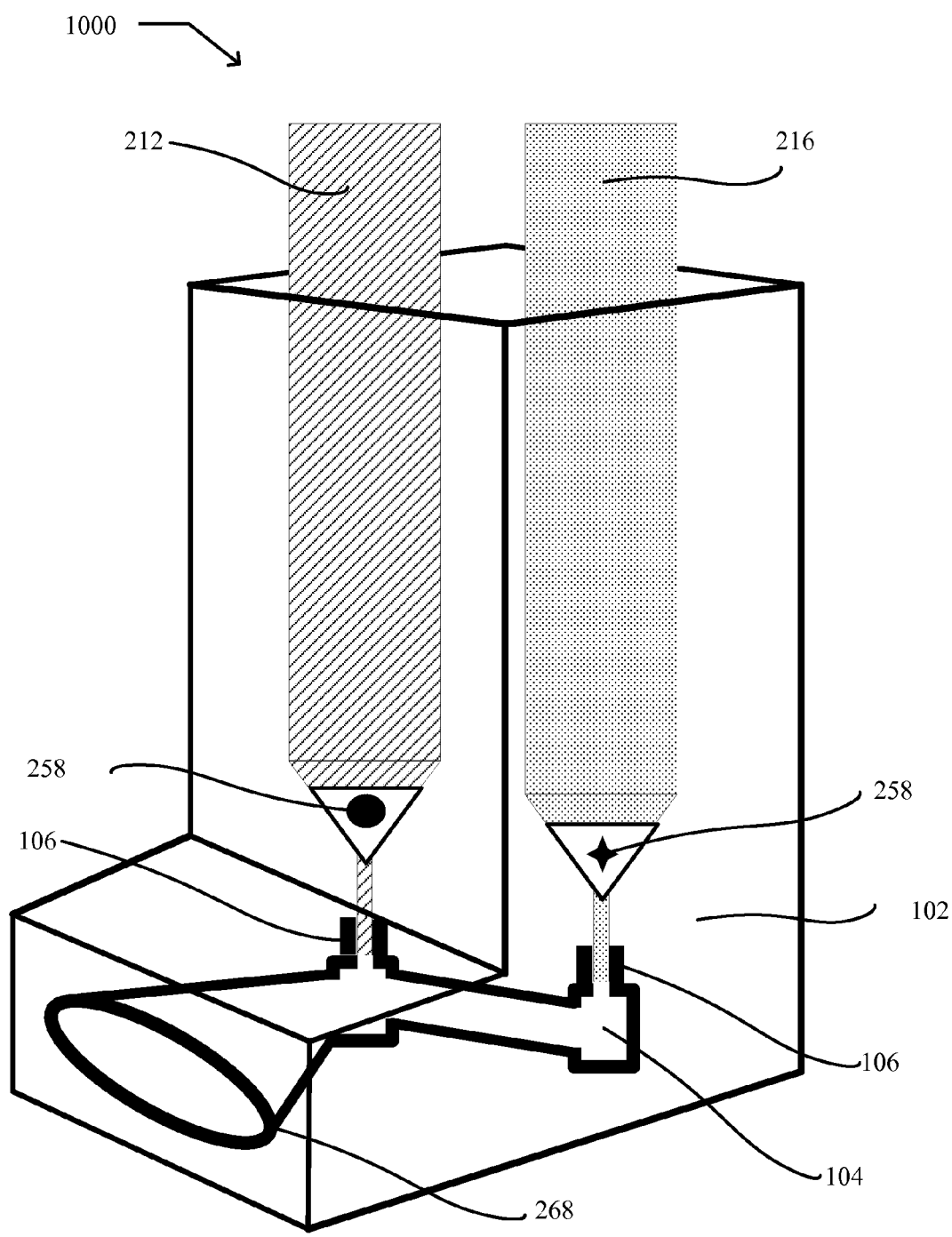
FIG. 10B illustrates a cross-sectional partial side view of an example inhaler 1000 in which embodiments may be implemented.

FIG. 10B illustrates a partial cross-sectional side view of system 1000. System 1000 is shown as an embodiment of a metered dose inhaler that includes a housing 102 having a flow channel 104 disposed therein. A mouthpiece 268 is operably coupled with the housing 102. An agent reservoir 212 and a propellant reservoir 216 are each operably coupled with a port 106 that are in fluid communication with the flow channel 104. The agent reservoir 212 and the propellant reservoir 216 are both configured as aerosol canisters that include a canister body and a valve stem that extends from the canister body into a port 106. The agent reservoir 212 includes a controllable valve 258. The propellant reservoir 216 also includes a controllable valve 258. The controllable valves 258 that are operably coupled to the agent reservoir 212 and the propellant reservoir 216 are illustrated as being closed as indicated by a closed circle and a closed star. System 1000 is configured as a metered dose inhaler that provides agent 214 released from an agent reservoir 212 and supplemental propellant 218 from a propellant reservoir 216.

Figure 10C:
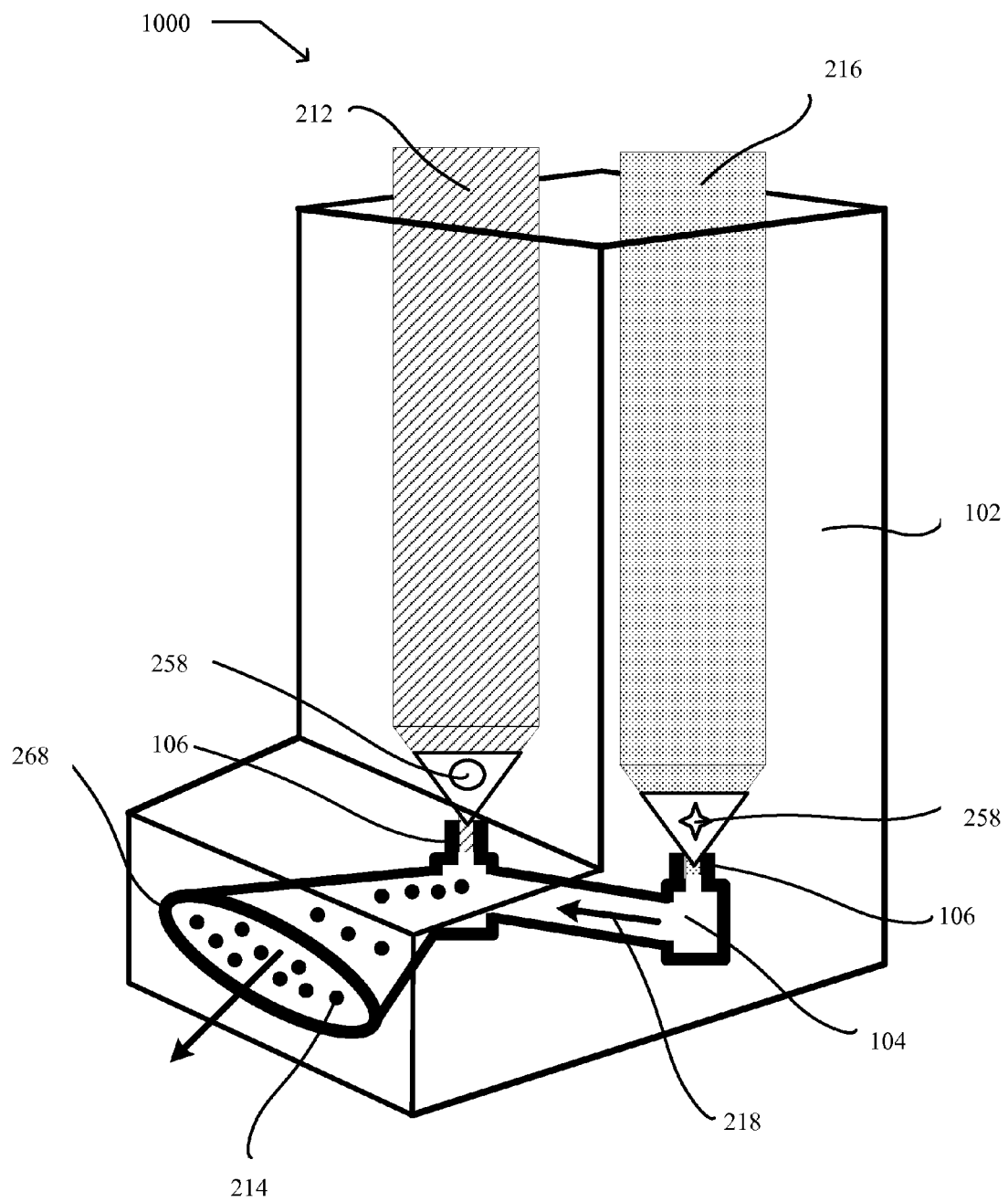
FIG. 10C illustrates a cross-sectional partial side view of an example inhaler 1000 in which embodiments may be implemented.

FIG. 10C illustrates a partial cross-sectional side view of system 1000. System 1000 is shown as an embodiment of a metered dose inhaler that includes a housing 102 having a flow channel 104 disposed therein. A mouthpiece 268 is operably coupled with the housing 102. An agent reservoir 212 and a propellant reservoir 216 are each operably coupled with a port 106 that are in fluid communication with the flow channel 104. The agent reservoir 212 and the propellant reservoir 216 are both configured as aerosol canisters that include a canister body and a valve stem that extends from the canister body into a port 106. The agent reservoir 212 includes a controllable valve 258. The propellant reservoir 216 also includes a controllable valve 258. The controllable valves 258 that are operably coupled to the agent reservoir 212 and the propellant reservoir 216 are illustrated as being open as indicated by an open circle and an open star. Agent 214 is illustrated as flowing through the flow channel 104 disposed within the housing 102 and through the mouthpiece 268. The direction of flow is indicated by an arrow. System 1000 is configured as a metered dose inhaler that provides agent 214 released from an agent reservoir 212 and supplemental propellant 218 from a propellant reservoir 216. A subject using the inhaler may press down on the agent reservoir 212 and on the propellant reservoir 216 to facilitate release of agent 214 and propellant 218.

Figure 11:
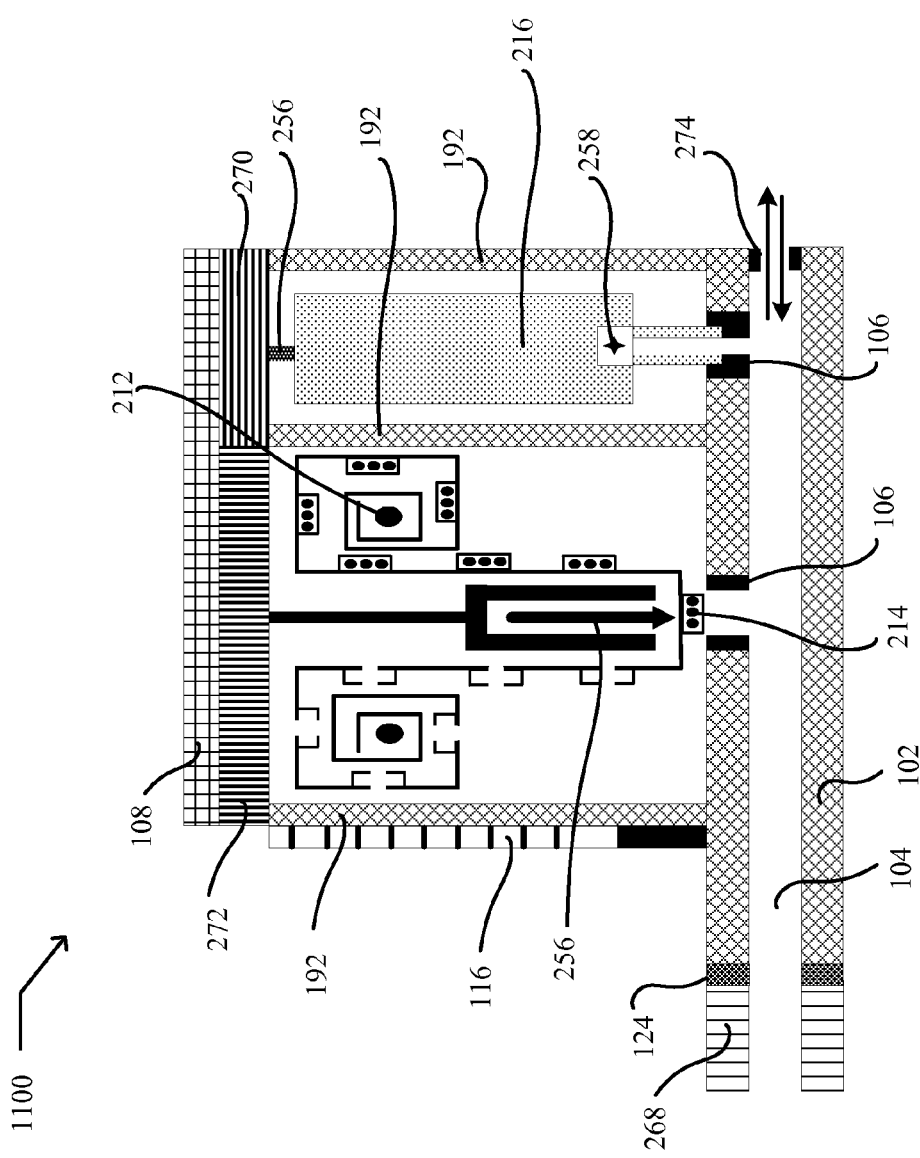
FIG. 11 illustrates a cross-sectional partial side view of an example inhaler 1100 in which embodiments may be implemented.

FIG. 11 illustrates a partial cross-sectional side view of system 1100 that is configured as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 includes a conveyor with a conveying drive configured to advance a blister strip that includes a plurality of blister packs that are filled with a powdered agent 214. The conveyor of the agent reservoir 212 is configured to advance the blister packs past a blister pack puncture mechanism 272 that includes a pushrod actuator 256 that is configured to puncture a blister pack and propel the powdered agent 214 contained within the blister pack through port 106 and into the flow channel 104. The propellant reservoir 216 is configured as an aerosol canister that includes a canister body and a valve stem that extends from the canister body into port 106. The propellant reservoir 216 includes a controllable valve 258. The controllable valve 258 that is operably coupled to the propellant reservoir 216 is illustrated as being closed as indicated by a closed star. Flow through the flow channel 104 is illustrated by two arrows pointing in opposite directions indicating bidirectional flow through the flow channel 104. A flow sensor 124 is operably coupled to the flow channel 104 and configured to detect flow through the flow channel 104. An aerosol canister content release mechanism 270 is illustrated with a pushrod actuator 256 operably coupled with the propellant reservoir 216. The aerosol canister content release mechanism 270 is operably coupled with a control unit 108. The control unit 108 is configured to direct operation of the aerosol canister content release mechanism 270 to control the pushrod actuator 256 to facilitate at least partial release from the propellant reservoir 216. The control unit 108 is operably coupled with flow sensor 124. A flow indicator 116 is illustrated as showing a moderate level of flow through the flow channel 104 disposed within the inhaler. A controllable flow valve 274 is illustrated as being in an open state to allow flow through the flow channel 104 disposed within the inhaler. The controllable flow valve 274 is operably coupled with control unit 108.

Figure 11A:
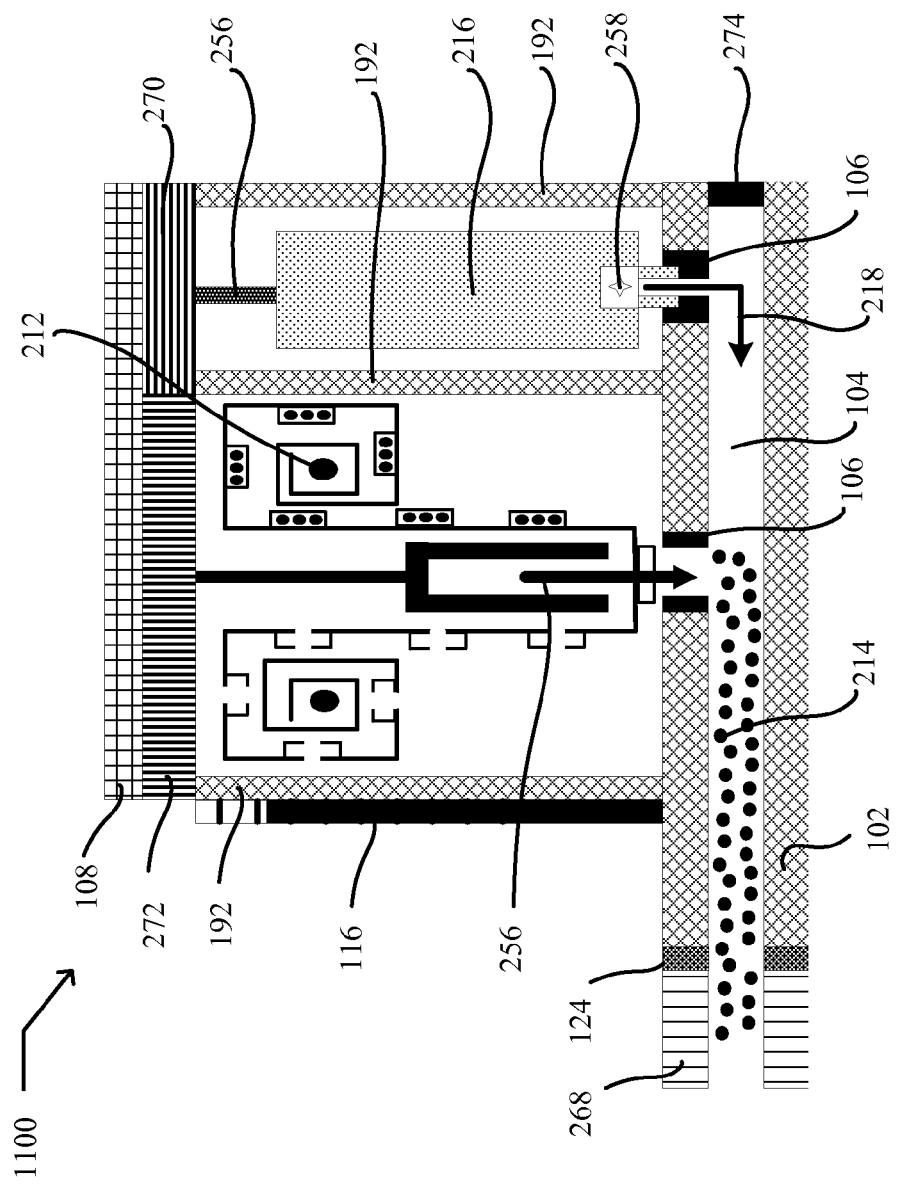
FIG. 11A illustrates a cross-sectional partial side view of an example inhaler 1100 in which embodiments may be implemented.

FIG. 11A illustrates a partial cross-sectional side view of system 1100 that is configured as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 includes a conveyor with a conveying drive configured to advance a blister strip that includes a plurality of blister packs that are filled with a powdered agent 214. The conveyor of the agent reservoir 212 is configured to advance the blister packs past a blister pack puncture mechanism 272 that includes a pushrod actuator 256 that is configured to puncture a blister pack and propel the powdered agent 214 contained within the blister pack through port 106 and into the flow channel 104. The propellant reservoir 216 is configured as an aerosol canister that includes a canister body and a valve stem that extends from the canister body into port 106. The propellant reservoir 216 includes a controllable valve 258. The controllable valve 258 that is operably coupled to the propellant reservoir 216 is illustrated as being open as indicated by an open star. Flow through the flow channel 104 is illustrated by an arrow pointing from right to left indicating flow through the flow channel 104 toward the mouthpiece 268. A flow sensor 124 is operably coupled to the flow channel 104 and configured to detect flow through the flow channel 104. An aerosol canister content release mechanism 270 is illustrated with a pushrod actuator 256 operably coupled with the propellant reservoir 216. The aerosol canister content release mechanism 270 is operably coupled with a control unit 108. The control unit 108 is configured to direct operation of the aerosol canister content release mechanism 270 to control the pushrod actuator 256 to facilitate at least partial release from the propellant reservoir 216. The control unit 108 is operably coupled with flow sensor 124. A flow indicator 116 is illustrated as showing a high level of flow through the flow channel 104 disposed within the inhaler. A controllable flow valve 274 is illustrated as being in a closed state to direct flow through the flow channel 104 disposed within the inhaler toward the mouthpiece 268. The controllable flow valve 274 is operably coupled with control unit 108.

Figure 12:
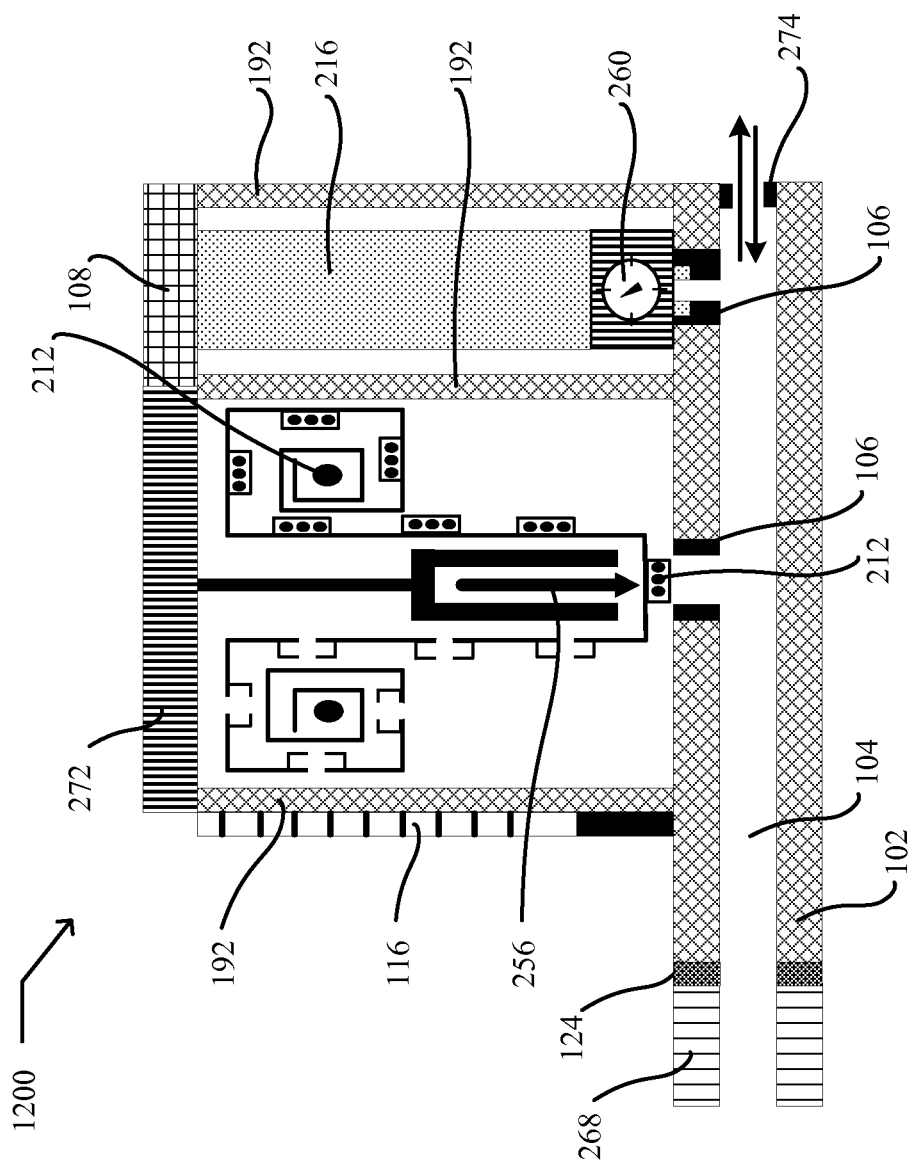
FIG. 12 illustrates a cross-sectional partial side view of an example inhaler 1200 in which embodiments may be implemented.

FIG. 12 illustrates a partial cross-sectional side view of system 1200 that is configured as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 includes a conveyor with a conveying drive configured to advance a blister strip that includes a plurality of blister packs that are filled with a powdered agent 214. The conveyor of the agent reservoir 212 is configured to advance the blister packs past a blister pack puncture mechanism 272 that includes a pushrod actuator 256 that is configured to puncture a blister pack and propel the powdered agent 214 contained within the blister pack through port 106 and into the flow channel 104. In some embodiments, the agent reservoir 212 may be operably coupled with control unit 108. In some embodiments, the agent reservoir 212 may be operably coupled with a flow sensor 124. In some embodiments, the agent reservoir 212 may be operably coupled with control unit 108 and flow sensor 124. Accordingly, in some embodiments, control unit 108 may control operation of the agent reservoir 212 to facilitate at least partial release of agent 214 from the agent reservoir 212. The propellant reservoir 216 is configured as a compressed gas cylinder that is operably coupled to a regulator 260. In some embodiments, the regulator 260 may be operably coupled with control unit 108. In some embodiments, the regulator 260 may be operably coupled with a flow sensor 124. In some embodiments, the regulator 260 may be operably coupled with control unit 108 and flow sensor 124. Accordingly, in some embodiments, control unit 108 may control operation of regulator 260 to facilitate at least partial release of propellant 218 from propellant reservoir 216. In some embodiments, control unit 108 may control operation of regulator 260 to facilitate at least partial release of propellant 218 from propellant reservoir 216 in response to flow through a flow channel 104 disposed within the inhaler during use of the inhaler by a subject. In FIG. 12, flow through the flow channel 104 is illustrated by two arrows pointing in opposite directions indicating bidirectional flow through the flow channel 104. A flow sensor 124 is operably coupled to the flow channel 104 and configured to detect flow through the flow channel 104. An aerosol canister content release mechanism 270 is illustrated with a pushrod actuator 256 operably coupled with the propellant reservoir 216. The aerosol canister content release mechanism 270 is operably coupled with a control unit 108. The control unit 108 is configured to direct operation of the aerosol canister content release mechanism 270 to control the pushrod actuator 256 to facilitate at least partial release from the propellant reservoir 216. The control unit 108 is operably coupled with flow sensor 124. A flow indicator 116 is illustrated as showing a moderate level of flow through the flow channel 104 disposed within the inhaler. A controllable flow valve 274 is illustrated as being in an open state to allow flow through the flow channel 104 disposed within the inhaler. The controllable flow valve 274 is operably coupled with control unit 108.

Figure 12A:
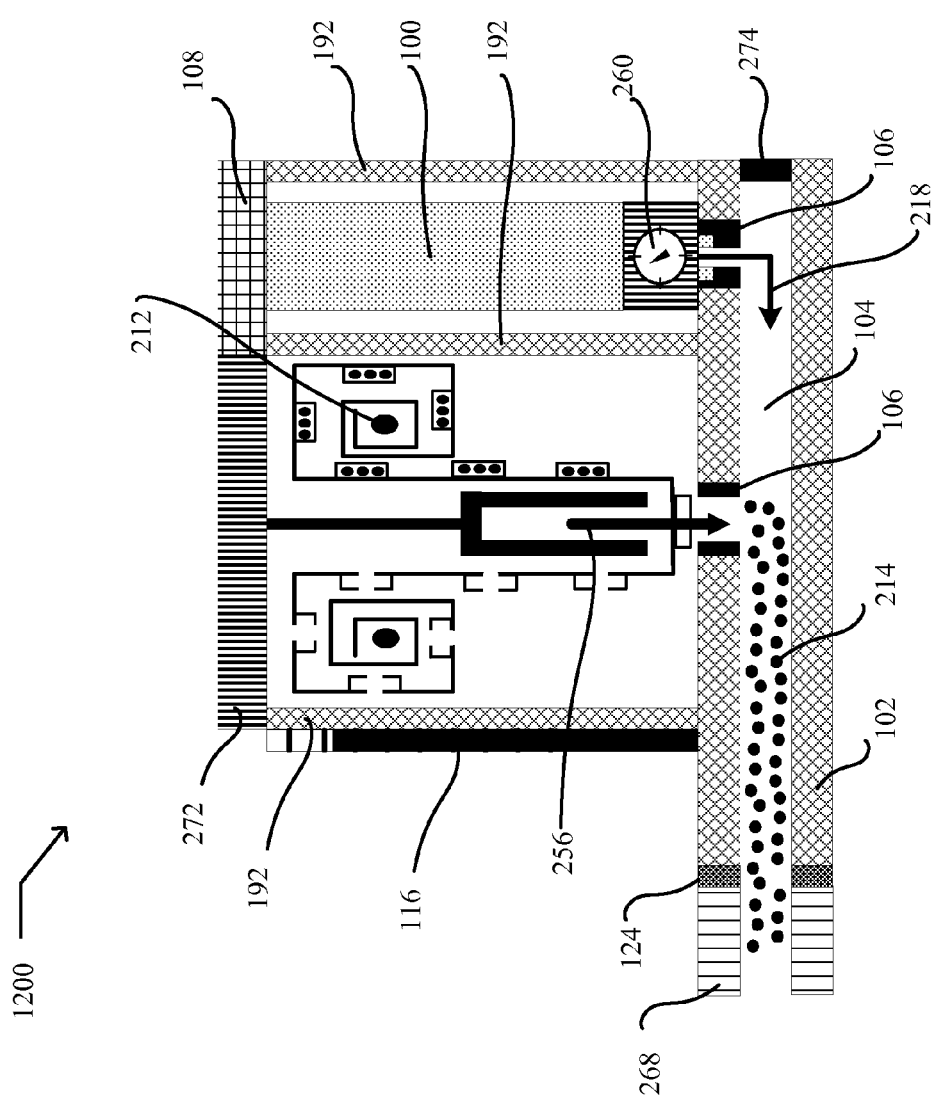
FIG. 12A illustrates a cross-sectional partial side view of an example inhaler 1200 in which embodiments may be implemented.

FIG. 12A illustrates a partial cross-sectional side view of system 1200 that is configured as an embodiment of an inhaler that includes a housing 102 having a flow channel 104 disposed therein. Also illustrated are two ports 106 disposed in the housing 102 in fluid communication with the flow channel 104. An agent reservoir 212 is illustrated as being operably coupled to one of the ports 106. A propellant reservoir 216 is illustrated as being operably coupled to the other port 106. The agent reservoir 212 and the propellant reservoir 216 are illustrated as being held within a reservoir support 192. The agent reservoir 212 includes a conveyor with a conveying drive configured to advance a blister strip that includes a plurality of blister packs that are filled with a powdered agent 214. The conveyor of the agent reservoir 212 is configured to advance the blister packs past a blister pack puncture mechanism 272 that includes a pushrod actuator 256 that is configured to puncture a blister pack and propel the powdered agent 214 contained within the blister pack through port 106 and into the flow channel 104. The propellant reservoir 216 is configured as a compressed gas cylinder that is operably coupled to a regulator 260. Flow through the flow channel 104 is illustrated by an arrow pointing from right to left that indicates directional flow of propellant 218 through the flow channel 104 toward the mouthpiece 268. A flow sensor 124 is operably coupled to the flow channel 104 and configured to detect flow through the flow channel 104. A flow indicator 116 is illustrated as showing a high level of flow through the flow channel 104 disposed within the inhaler. A controllable flow valve 274 is illustrated as being in a closed state to direct flow of agent 214 and propellant 218 through the flow channel 104 disposed within the inhaler toward the mouthpiece 268. The controllable flow valve 274 is operably coupled with control unit 108.

FIG. 13 illustrates a partial cross-sectional side view of system 1300 that is configured as an embodiment of an inhaler that includes a housing 102 having a flow channel 104 disposed therein. Also illustrated are three ports 106 disposed in the housing 102 in fluid communication with the flow channel 104. A first agent reservoir 212 is illustrated as being operably coupled to one of the ports 106. A second agent reservoir 212A is illustrated as being operably coupled to one of the ports 106. A propellant reservoir 216 is illustrated as being operably coupled to one of the ports 106. The first agent reservoir 212, second agent reservoir 212A, and the propellant reservoir 216 are illustrated as being held within a reservoir support 192. The first agent reservoir 212 includes a conveyor with a conveying drive configured to advance a blister strip that includes a plurality of blister packs that are filled with a powdered agent 214. The conveyor of the first agent reservoir 212 is configured to advance the blister packs past a blister pack puncture mechanism 272 that includes a pushrod actuator 256 that is configured to puncture a blister pack and propel the powdered agent 214 contained within the blister pack through port 106 and into the flow channel 104. In some embodiments, the first agent reservoir 212 may be operably coupled with control unit 108. In some embodiments, the first agent reservoir 212 may be operably coupled with a flow sensor 124. In some embodiments, the first agent reservoir 212 may be operably coupled with control unit 108 and flow sensor 124. Accordingly, in some embodiments, control unit 108 may control operation of the first agent reservoir 212 to facilitate at least partial release of agent 214 from the agent reservoir 212. The second agent reservoir 212A is configured as an aerosol canister that includes a canister body and a valve stem that extends from the canister body into a port 106. The second agent reservoir 212A includes a controllable valve 258. The controllable valve 258 that is operably coupled to the second agent reservoir 212A is illustrated as being closed as indicated by a closed circle. An aerosol canister content release mechanism 270 is illustrated with a pushrod actuator 256 operably coupled with the second agent reservoir 212A. The aerosol canister content release mechanism 270 is operably coupled with a control unit 108. The control unit 108 is configured to direct operation of the aerosol canister content release mechanism 270 to control the pushrod actuator 256 to facilitate at least partial release from the second agent reservoir 212A. The propellant reservoir 216 is configured as an aerosol canister that includes a canister body and a valve stem that extends from the canister body into port 106. The propellant reservoir 216 includes a controllable valve 258. The controllable valve 258 that is operably coupled to the propellant reservoir 216 is illustrated as being closed as indicated by a closed star. Flow through the flow channel 104 is illustrated by two arrows pointing in opposite directions indicating bidirectional flow through the flow channel 104. A flow sensor 124 is operably coupled to the flow channel 104 and configured to detect flow through the flow channel 104. An aerosol canister content release mechanism 270 is illustrated with a pushrod actuator 256 operably coupled with the propellant reservoir 216. The aerosol canister content release mechanism 270 is operably coupled with a control unit 108. The control unit 108 is configured to direct operation of the aerosol canister content release mechanism 270 to control the pushrod actuator 256 to facilitate at least partial release from the propellant reservoir 216. The control unit 108 is operably coupled with flow sensor 124. A flow indicator 116 is illustrated as showing a moderate level of flow through the flow channel 104 disposed within the inhaler. A controllable flow valve 274 is illustrated as being in an open state to allow flow through the flow channel 104 disposed within the inhaler. The controllable flow valve 274 is operably coupled with control unit 108.

FIG. 13A illustrates a partial cross-sectional side view of system 1300 that is configured as an embodiment of an inhaler in an activated state to release one or more agents 214 from one or more agent reservoirs 212 and propellant 218 from a propellant reservoir 216. The inhaler includes a housing 102 having a flow channel 104 disposed therein. Also illustrated are three ports 106 disposed in the housing 102 in fluid communication with the flow channel 104. A first agent reservoir 212 is illustrated as being operably coupled to one of the ports 106. A second agent reservoir 212A is illustrated as being operably coupled to one of the ports 106. A propellant reservoir 216 is illustrated as being operably coupled to one of the ports 106. The first agent reservoir 212, second agent reservoir 212A, and the propellant reservoir 216 are illustrated as being held within a reservoir support 192. The first agent reservoir 212 includes a conveyor with a conveying drive configured to advance a blister strip that includes a plurality of blister packs that are filled with a powdered agent 214. The conveyor of the first agent reservoir 212 is configured to advance the blister packs past a blister pack puncture mechanism 272 that includes a pushrod actuator 256 that is configured to puncture a blister pack and propel the powdered agent 214 contained within the blister pack through port 106 and into the flow channel 104. In some embodiments, the first agent reservoir 212 may be operably coupled with control unit 108. In some embodiments, the first agent reservoir 212 may be operably coupled with a flow sensor 124. In some embodiments, the first agent reservoir 212 may be operably coupled with control unit 108 and flow sensor 124. Accordingly, in some embodiments, control unit 108 may control operation of the first agent reservoir 212 to facilitate at least partial release of agent 214 from the agent reservoir 212. The second agent reservoir 212A is configured as aerosol canister that includes a canister body and a valve stem that extends from the canister body into a port 106. The agent reservoir 212 includes a controllable valve 258. The controllable valve 258 that is operably coupled to the agent reservoir 212 is illustrated as being closed as indicated by a closed circle. An aerosol canister content release mechanism 270 is illustrated with a pushrod actuator 256 operably coupled with the second agent reservoir 212A. The aerosol canister content release mechanism 270 is operably coupled with a control unit 108. The control unit 108 is configured to direct operation of the aerosol canister content release mechanism 270 to control the pushrod actuator 256 to facilitate at least partial release from the second agent reservoir 212A. The propellant reservoir 216 is configured as an aerosol canister that includes a canister body and a valve stem that extends from the canister body into port 106. The propellant reservoir 216 includes a controllable valve 258. The controllable valve 258 that is operably coupled to the propellant reservoir 216 is illustrated as being open as indicated by an open star. Flow of propellant 218 through the flow channel 104 is illustrated by an arrow pointing from right to left toward the mouthpiece 268. A flow sensor 124 is operably coupled to the flow channel 104 and configured to detect flow through the flow channel 104. An aerosol canister content release mechanism 270 is illustrated with a pushrod actuator 256 operably coupled with the propellant reservoir 216. The aerosol canister content release mechanism 270 is operably coupled with a control unit 108. The control unit 108 is configured to direct operation of the aerosol canister content release mechanism 270 to control the pushrod actuator 256 to facilitate at least partial release from the propellant reservoir 216. The control unit 108 is operably coupled with flow sensor 124. A flow indicator 116 is illustrated as showing a high level of flow through the flow channel 104 disposed within the inhaler. A controllable flow valve 274 is illustrated as being in a closed state to direct flow through the flow channel 104 disposed within the inhaler toward the mouthpiece 268. The controllable flow valve 274 is operably coupled with control unit 108.

Figure 13:
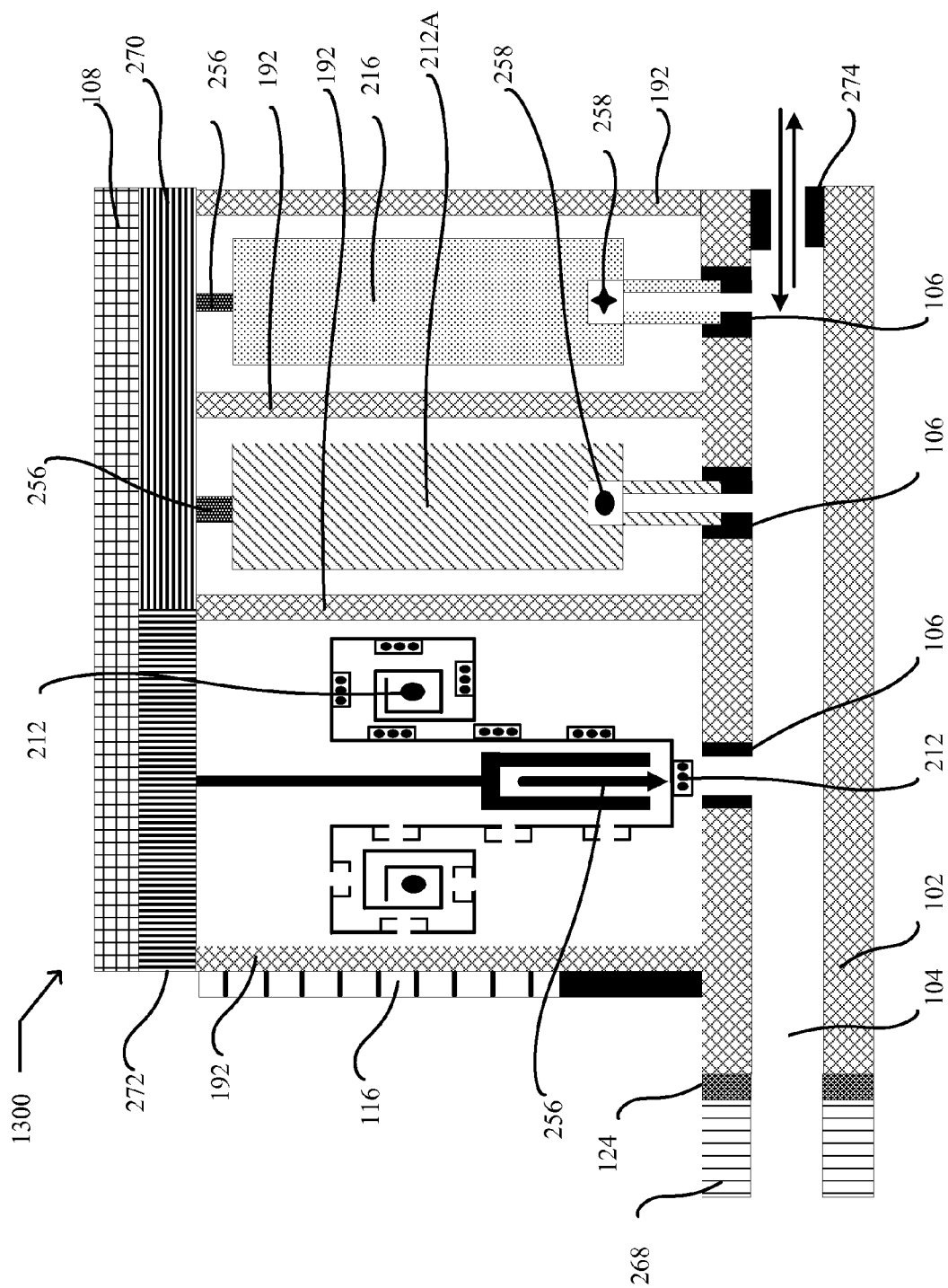
FIG. 13 illustrates a cross-sectional partial side view of an example inhaler 1300 in which embodiments may be implemented.
Figure 13A:
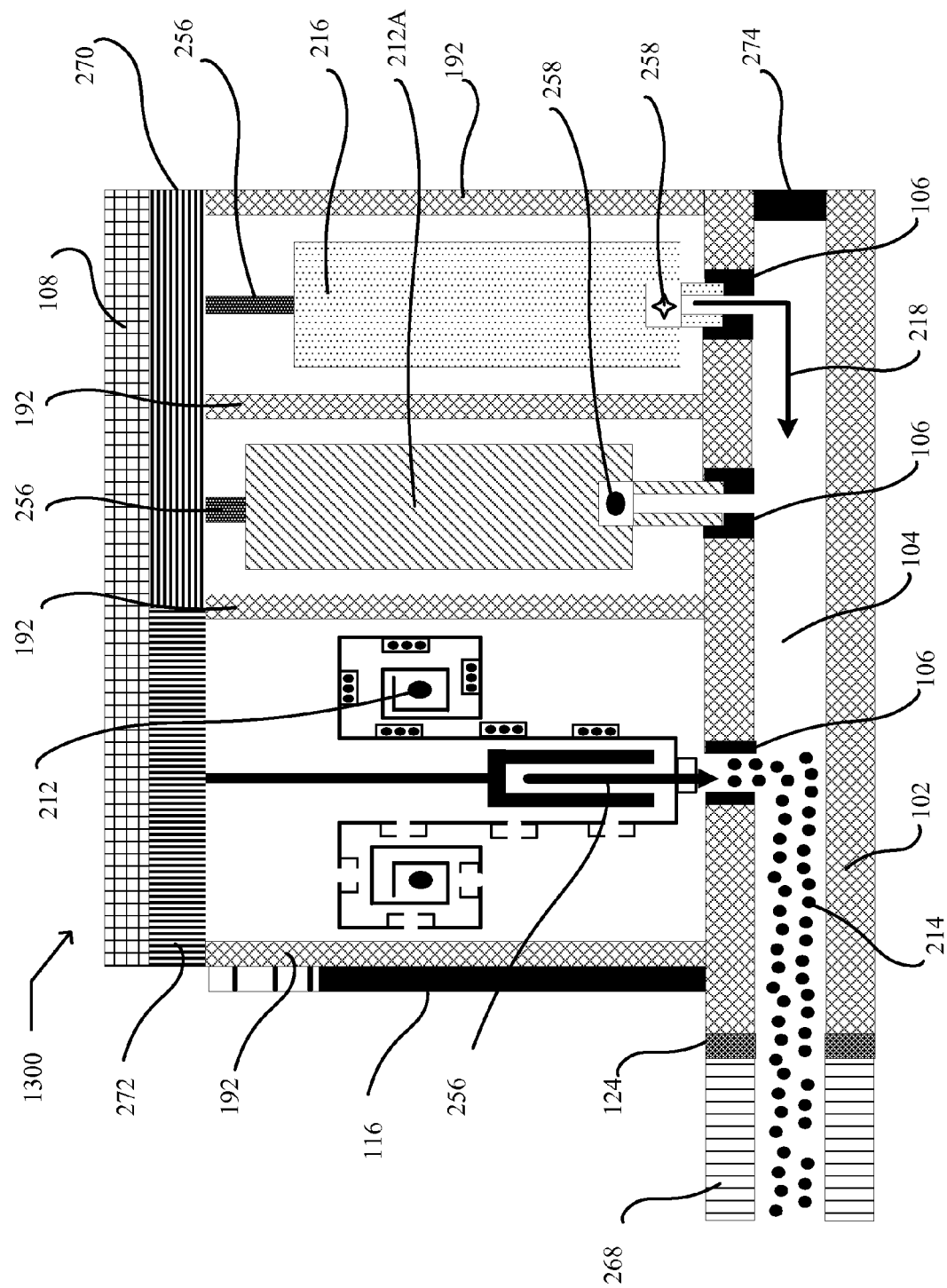
FIG. 13A illustrates a cross-sectional partial side view of an example inhaler 1300 in which embodiments may be implemented.
Figure 13B:
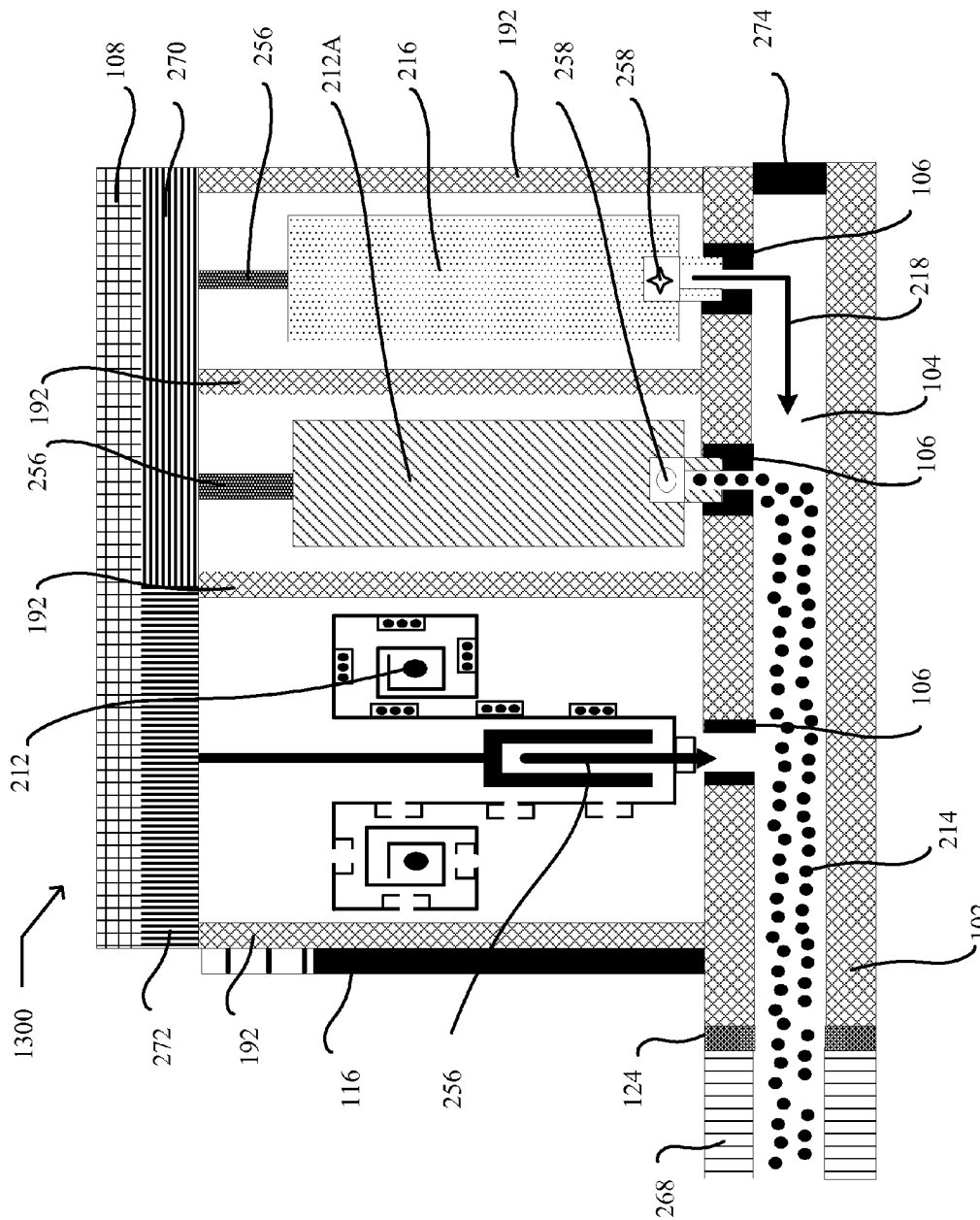
FIG. 13B illustrates a cross-sectional partial side view of an example inhaler 1300 in which embodiments may be implemented.

FIG. 13B illustrates a partial cross-sectional side view of system 1300 that is configured as an embodiment of an inhaler in an activated state to release one or more agents 214 from one or more agent reservoirs 212 and propellant 218 from a propellant reservoir 216. The inhaler includes a housing 102 having a flow channel 104 disposed therein. Also illustrated are three ports 106 disposed in the housing 102 in fluid communication with the flow channel 104. A first agent reservoir 212 is illustrated as being operably coupled to one of the ports 106. A second agent reservoir 212A is illustrated as being operably coupled to one of the ports 106. A propellant reservoir 216 is illustrated as being operably coupled to one of the ports 106. The first agent reservoir 212, second agent reservoir 212A, and the propellant reservoir 216 are illustrated as being held within a reservoir support 192. The first agent reservoir 212 includes a conveyor with a conveying drive configured to advance a blister strip that includes a plurality of blister packs that are filled with a powdered agent 214. The conveyor of the first agent reservoir 212 is configured to advance the blister packs past a blister pack puncture mechanism 272 that includes a pushrod actuator 256 that is configured to puncture a blister pack and propel the powdered agent 214 contained within the blister pack through port 106 and into the flow channel 104. In some embodiments, the first agent reservoir 212 may be operably coupled with control unit 108. In some embodiments, the first agent reservoir 212 may be operably coupled with a flow sensor 124. In some embodiments, the first agent reservoir 212 may be operably coupled with control unit 108 and flow sensor 124. Accordingly, in some embodiments, control unit 108 may control operation of the first agent reservoir 212 to facilitate at least partial release of agent 214 from the agent reservoir 212. The second agent reservoir 212A is configured as aerosol canister that includes a canister body and a valve stem that extends from the canister body into a port 106. The agent reservoir 212 includes a controllable valve 258. The controllable valve 258 that is operably coupled to the agent reservoir 212 is illustrated as being open as indicated by an open circle. An aerosol canister content release mechanism 270 is illustrated with a pushrod actuator 256 operably coupled with the second agent reservoir 212A. The aerosol canister content release mechanism 270 is operably coupled with a control unit 108. The control unit 108 is configured to direct operation of the aerosol canister content release mechanism 270 to control the pushrod actuator 256 to facilitate at least partial release from the second agent reservoir 212A. The propellant reservoir 216 is configured as an aerosol canister that includes a canister body and a valve stem that extends from the canister body into port 106. The propellant reservoir 216 includes a controllable valve 258. The controllable valve 258 that is operably coupled to the propellant reservoir 216 is illustrated as being open as indicated by an open star. Flow of propellant 218 through the flow channel 104 is illustrated by an arrow pointing from right to left toward the mouthpiece 268. A flow sensor 124 is operably coupled to the flow channel 104 and configured to detect flow through the flow channel 104. An aerosol canister content release mechanism 270 is illustrated with a pushrod actuator 256 operably coupled with the propellant reservoir 216. The aerosol canister content release mechanism 270 is operably coupled with a control unit 108. The control unit 108 is configured to direct operation of the aerosol canister content release mechanism 270 to control the pushrod actuator 256 to facilitate at least partial release from the propellant reservoir 216. The control unit 108 is operably coupled with flow sensor 124. A flow indicator 116 is illustrated as showing a high level of flow through the flow channel 104 disposed within the inhaler. A controllable flow valve 274 is illustrated as being in a closed state to direct flow through the flow channel 104 disposed within the inhaler toward the mouthpiece 268. The controllable flow valve 274 is operably coupled with control unit 108.

FIG. 14 illustrates operational flow 1400 that includes operation 1410 that includes assessing one or more parameters associated with flow through at least one flow channel 104 disposed within an inhaler used by a subject to obtain at least one assessed flow value, operation 1420 that includes calculating an amount of propellant 218 that will increase flow through the at least one flow channel 104 to meet or exceed a threshold flow value if the at least one assessed flow value is below the threshold flow value, and operation 1430 that includes dispensing at least one agent 214 with the amount of propellant 218 that will cause the flow through the at least one flow channel 104 to meet or exceed the threshold flow value.

Figure 14:
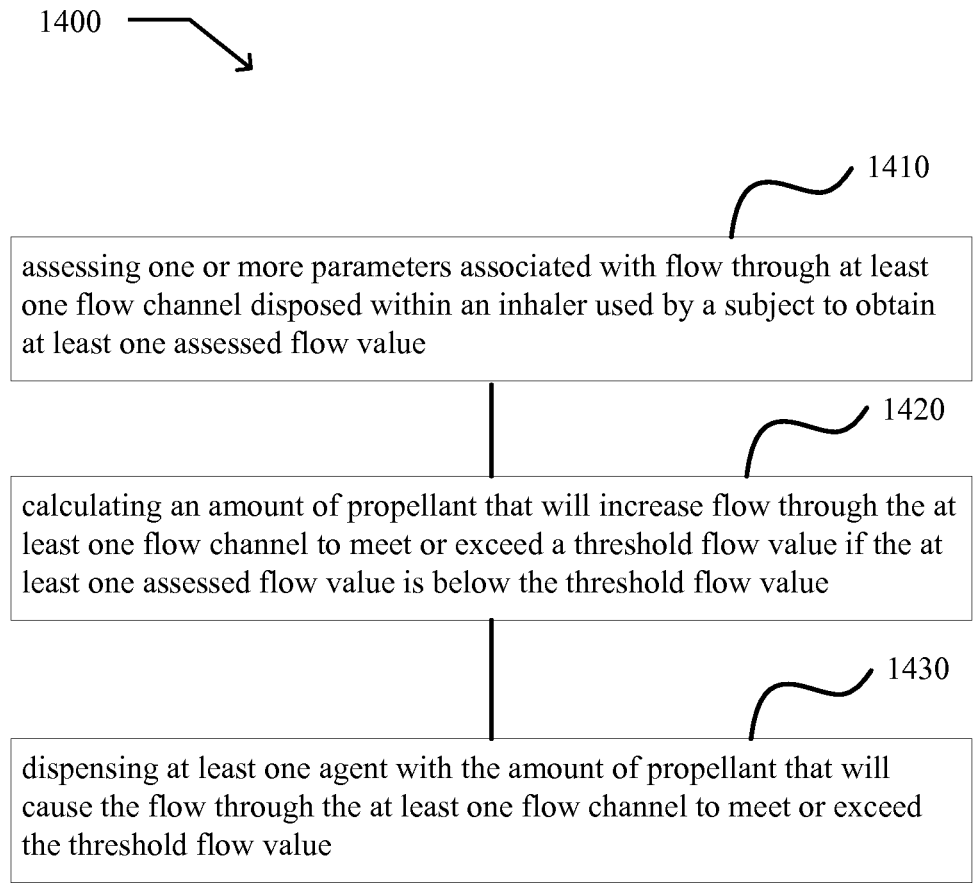
FIG. 14 illustrates an example operational flow 1400 in which embodiments may be implemented.

In FIG. 14 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1410 includes assessing one or more parameters associated with flow through at least one flow channel 104 disposed within an inhaler used by a subject to obtain at least one assessed flow value. In some embodiments, system 100 may be used to assess one or more parameters associated with flow through at least one flow channel 104 disposed within an inhaler used by a subject to obtain at least one assessed flow value. For example, in some embodiments, a sensor 114 may be used to assess one or more parameters associated with flow through at least one flow channel 104 disposed within an inhaler. In some embodiments, a control unit 108 may be used to assess flow through at least one flow channel 104 disposed within an inhaler. In some embodiments, a flow indicator 116 may be used to assess flow through at least one flow channel 104 disposed within an inhaler. In some embodiments, a user interface 110 may be used to assess flow through at least one flow channel 104 disposed within an inhaler. Numerous parameters associated with flow through at least one flow channel 104 disposed within an inhaler may be assessed. Examples of such parameters include, but are not limited to, volume of agent 214 and/or propellant 218 flowing through a flow channel 104, quantity of agent 214 flowing through a flow channel 104, velocity of flow through a flow channel 104, and the like.

Operation 1420 includes calculating an amount of propellant 218 that will increase flow through the at least one flow channel 104 to meet or exceed a threshold flow value if the at least one assessed flow value is below the threshold flow value. In some embodiments, system 100 may be used to calculate an amount of propellant 218 that will increase flow through at least one flow channel 104 to meet or exceed a threshold flow value if at least one assessed flow value is below a threshold flow value. For example, in some embodiments, a control unit 108 may receive one or more assessed values associated with flow through a flow channel 104 disposed within an inhaler from a sensor 114 that is operably coupled with the flow channel 104. The control unit 108 may then compare the assessed value to a threshold flow value and calculate a quantity of propellant 218 that will increase flow to meet or exceed the threshold flow value. In some embodiments, assessed values may be associated with flow of agent 214 through a flow channel 104. In some embodiments, assessed values may be associated with flow of propellant 218 through a flow channel 104. Accordingly, an assessed value may be associated with numerous parameters related to flow through a flow channel 104. The control unit 108 may compare an assessed value to a threshold value that is associated with a subject using an inhaler. In some embodiments, such threshold values may be associated with a specific subject using an inhaler. For example, in some embodiments, a threshold value may be related to the lung volume of a subject using an inhaler. Examples of parameters associated with lung volume include, but are not limited to, total lung volume, tidal volume, residual volume, inspiratory capacity, inspiratory vital capacity, vital capacity, and the like. In some embodiments, a threshold value may be related to the age of a subject using an inhaler. In some embodiments, a threshold value may be related to one or more physical characteristics associated with a subject using an inhaler. Examples of such physical characteristics include, but are not limited to, height, weight, endurance, respiratory performance, disease state, physical fitness, and the like. Accordingly, threshold values may selected that are related to numerous parameters associated with a specific subject using an inhaler.

Operation 1430 includes dispensing at least one agent 214 with the amount of propellant 218 that will cause the flow through the at least one flow channel 104 to meet or exceed a threshold flow value. In some embodiments, system 100 may be used to dispense at least one agent 214 with an amount of propellant 218 that will cause flow through at least one flow channel 104 to meet or exceed a threshold flow value. For example, in some embodiments, a control unit 108 may calculate an amount of propellant 218 that will increase flow through at least one flow channel 104 to meet or exceed a threshold flow value if at least one assessed flow value is below a threshold flow value. The control unit 108 may transmit one or more signals 112 that direct one or more actuators 120 to facilitate release of an amount of propellant 218 from one or more propellant reservoirs 216 into a flow channel 104 that increases flow to meet or exceed a threshold flow value.

In some embodiments, operation 1410 includes assessing a volume of gas flowing through the at least one flow channel 104 (not shown). In some embodiments, system 100 may be used to assess a volume of gas flowing through at least one flow channel 104. For example, in some embodiments, a flow sensor 124 that is operably coupled to a flow channel 104 disposed within an inhaler may be used to assess flow through the flow channel 104. In some embodiments, a flow sensor 124 may transmit one or more signals 112 that include one or more values associated with flow through a flow channel 104 to a control unit 108. The control unit 108 may then calculate an amount of additional propellant 218 to be released into the flow channel 104 to increase the flow to meet or exceed a threshold value. The control unit 108 may then direct one or more actuators 120 to facilitate release of propellant 218 from one or more propellant reservoirs 216 to meet or exceed the threshold flow value.

In some embodiments, operation 1410 includes assessing gas pressure within the at least one flow channel 104 (not shown). In some embodiments, system 100 may be used to assess gas pressure within at least one flow channel 104. For example, in some embodiments, a pressure sensor 130 that is operably coupled to a flow channel 104 disposed within an inhaler may be used to assess pressure within the flow channel 104. In some embodiments, a pressure sensor 130 may transmit one or more signals 112 that include one or more values associated with pressure within a flow channel 104 to a control unit 108. The control unit 108 may then calculate an amount of additional propellant 218 to be released into the flow channel 104 to increase the pressure to meet or exceed a threshold value. The control unit 108 may then direct one or more actuators 120 to facilitate release of propellant 218 from one or more propellant reservoirs 216 to meet or exceed the threshold flow value.

In some embodiments, operation 1410 includes assessing vacuum pressure within the at least one flow channel 104 (not shown). In some embodiments, system 100 may be used to assess vacuum pressure within at least one flow channel 104. For example, in some embodiments, a vacuum sensor 132 that is operably coupled to a flow channel 104 disposed within an inhaler may be used to assess vacuum applied to the flow channel 104. In some embodiments, a vacuum sensor 132 may transmit one or more signals 112 that include one or more values associated with vacuum applied to a flow channel 104 to a control unit 108. The control unit 108 may then calculate an amount of propellant 218 to be released into the flow channel 104 to meet or exceed a threshold value. The control unit 108 may then direct one or more actuators 120 to facilitate release of propellant 218 from one or more propellant reservoirs 216 to meet or exceed the threshold flow value.

In some embodiments, operation 1410 includes assessing velocity of gas flow through the at least one flow channel 104 (not shown). In some embodiments, system 100 may be used to assess velocity of gas flow through at least one flow channel 104. For example, in some embodiments, a velocimeter 138 that is operably coupled to a flow channel 104 disposed within an inhaler may be used to assess the velocity of flow through the flow channel 104. In some embodiments, a velocimeter 138 may transmit one or more signals 112 that include one or more values associated with the velocity of flow through a flow channel 104 to a control unit 108. The control unit 108 may then calculate an amount of propellant 218 to be released into the flow channel 104 to increase the velocity of flow through the flow channel 104 to meet or exceed a threshold value. The control unit 108 may then direct one or more actuators 120 to facilitate release of propellant 218 from one or more propellant reservoirs 216 to meet or exceed the threshold velocity value.

In some embodiments, operation 1410 includes assessing one or more time periods associated with at least one of an inhalation cycle, a breath hold cycle, or an exhalation cycle through the at least one flow channel 104 (not shown). In some embodiments, system 100 may be used to assess one or more time periods associated with at least one of an inhalation cycle, a breath hold cycle, or an exhalation cycle through at least one flow channel 104. For example, in some embodiments, a timer 134 that is operably coupled to a flow channel 104 disposed within an inhaler may be used to assess one or more time values associated with flow through the flow channel 104. In some embodiments, a timer 134 may transmit one or more signals 112 that include one or more time values associated with flow through a flow channel 104 to a control unit 108. The control unit 108 may then calculate an amount of propellant 218 to be released into the flow channel 104 to meet or exceed a threshold value associated with flow through a flow channel 104. In some embodiments, the control unit 108 may also assess a time period when propellant 218 should be released from one or more propellant reservoirs 216 to deliver agent 214 to a subject using an inhaler during an inhalation cycle. The control unit 108 may then direct one or more actuators 120 to facilitate release of propellant 218 from one or more propellant reservoirs 216 in accordance with one or more time values.

In some embodiments, operation 1410 includes assessing a quantity of the at least one agent 214 flowing through the at least one flow channel 104 (not shown). In some embodiments, system 100 may be used to assess a quantity of the at least one agent 214 flowing through at least one flow channel 104. For example, in some embodiments, a sensor 130 that is operably coupled to a flow channel 104 disposed within an inhaler may be used to assess a quantity of agent 214 flowing through the flow channel 104. Numerous types of sensors 114 may be used to determine a quantity of agent 214 flowing through a flow channel 104. Examples of such sensors 114 include, but are not limited to, optical sensors 126, phase Doppler interferometers 136, ultrasonic flow meters 140, and the like. In some embodiments, a sensor 114 may transmit one or more signals 112 that include one or more values associated with a quantity of agent 214 flowing through a flow channel 104 to a control unit 108. The control unit 108 may then calculate an amount of additional agent 214 to be released into the flow channel 104 to meet a desired dosage level. The control unit 108 may then direct one or more actuators 120 to facilitate release of agent 214 from one or more agent reservoirs 212 meet a desired dosage level.

In some embodiments, operation 1410 includes assessing a quantity of the at least one agent 214 flowing through the at least one flow channel 104 with an optical sensor 126 (not shown). In some embodiments, system 100 may be used to assess a quantity of the at least one agent 214 flowing through at least one flow channel 104 with an optical sensor 126. For example, in some embodiments, an optical sensor 126 that is operably coupled to a flow channel 104 disposed within an inhaler may be used to assess a quantity of agent 214 flowing through the flow channel 104. Numerous types of optical sensors 126 may be used to determine a quantity of agent 214 flowing through a flow channel 104. Examples of such optical sensors 126 include, but are not limited to, fiber optic optical sensors 126, electro-optical sensors 126, photointerrupter optical sensors 126, and the like. In some embodiments, an optical sensor 126 may transmit one or more signals 112 that include one or more values associated with a quantity of agent 214 flowing through a flow channel 104 to a control unit 108. The control unit 108 may then calculate an amount of additional agent 214 to be released into the flow channel 104 to meet a desired dosage level. The control unit 108 may then direct one or more actuators 120 to facilitate release of agent 214 from one or more agent reservoirs 212 meet a desired dosage level.

In some embodiments, operation 1410 includes assessing a quantity of the at least one agent 214 flowing through the at least one flow channel 104 with a phase Doppler interferometer 136 (not shown). In some embodiments, system 100 may be used to assess a quantity of the at least one agent 214 flowing through at least one flow channel 104 with a phase Doppler interferometer 136. For example, in some embodiments, a phase Doppler interferometer 136 that is operably coupled to a flow channel 104 disposed within an inhaler may be used to assess a quantity of agent 214 flowing through the flow channel 104. In some embodiments, a phase Doppler interferometer 136 may transmit one or more signals 112 that include one or more values associated with a quantity of agent 214 flowing through a flow channel 104 to a control unit 108. The control unit 108 may then calculate an amount of additional agent 214 to be released into the flow channel 104 to meet a desired dosage level. The control unit 108 may then direct one or more actuators 120 to facilitate release of agent 214 from one or more agent reservoirs 212 meet a desired dosage level.

In some embodiments, operation 1410 includes assessing flow through the at least one flow channel 104 with a spirometer (not shown). In some embodiments, system 100 may be used to assess flow through at least one flow channel 104 with a spirometer. For example, in some embodiments, a flow sensor 124 configured as a spirometer is operably coupled to a flow channel 104 disposed within an inhaler and may be used to assess flow through the flow channel 104. In some embodiments, spirometer may transmit one or more signals 112 that include one or more values associated with flow through a flow channel 104 to a control unit 108. The control unit 108 may then calculate an amount of additional propellant 218 to be released into the flow channel 104 to increase the flow to meet or exceed a threshold value. The control unit 108 may then direct one or more actuators 120 to facilitate release of propellant 218 from one or more propellant reservoirs 216 to meet or exceed the threshold flow value.

In some embodiments, operation 1420 includes comparing the at least one assessed flow value to a threshold flow value related to the subject (not shown). In some embodiments, system 100 may be used to compare at least one assessed flow value to a threshold flow value related to a subject. For example, in some embodiments, a control unit 108 may receive one or more threshold values related to a subject using an inhaler. Such threshold values may include, but are not limited to, values related to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with characteristics associated with a subject. For example, in some embodiments, a database may include threshold values that are related to the age of a subject, the height of a subject, the lung capacity of a subject, the tidal volume of a subject, the health status of a subject, and the like. Accordingly, threshold values may be related to numerous characteristics of a subject using an inhaler. In some embodiments, a control unit 108 may compare a threshold value related to a subject to one or more assessed flow values. For example, in some embodiments, a control unit 108 may compare a threshold value associated with flow through a flow channel 104 disposed within an inhaler to an assessed flow value associated with use of the inhaler by a subject. If the assessed value is less than the threshold value, the control unit 108 may calculate an amount of propellant 218 that will supplement flow through the flow channel 104 to meet or exceed the threshold flow value. In some embodiments, supplemental propellant 218 flow may be used to deliver an agent 214 to a subject having impaired respiratory function. For example, in some embodiments, supplemental propellant 218 flow may be used to deliver an agent 214 to a subject undergoing an asthma attack.

In some embodiments, operation 1420 includes comparing the at least one assessed flow value to a threshold flow value related to an age of the subject (not shown). In some embodiments, system 100 may be used to compare at least one assessed flow value to a threshold flow value related to an age of a subject. For example, in some embodiments, a control unit 108 may receive one or more threshold values related to the age of a subject using an inhaler. Such threshold values may include, but are not limited to, values related to volume of propellant 218 to be delivered to the subject, velocity of propellant 218 to be delivered to the subject, quantity of agent 214 to be delivered to the subject, location within the respiratory tract where agent 214 is to be delivered, and the like. For example, in asthmatic children aged 3-10 years, a mean peak inspiratory flow rate was determined to be 104 liters/minute (see e.g., Nielson et al., Flow-dependent effect of formoterol dry-powder inhaled from the Aerolizer, Eur. Respir. J., 10:2105-2109 (1997), herein incorporated by reference). The peak inspiratory flow rate varied from about 60 liters/minute in 3 year old asthmatic children to about 140 liters/minute in 10 year old asthmatic children. Accordingly, such flow rates may be used to set threshold values based on age. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with characteristics associated with a subject. For example, in some embodiments, a database may include threshold values that relate the age of a subject to a volume of propellant that should be delivered to the subject, the velocity at which propellant should be delivered to the subject, and the like. In some embodiments, a control unit 108 may compare a threshold value related to a subject to one or more assessed flow values. For example, in some embodiments, a control unit 108 may compare a threshold value associated with flow through a flow channel 104 disposed within an inhaler to an assessed flow value associated with use of the inhaler by a subject. If the assessed value is less than the threshold value, the control unit 108 may calculate an amount of propellant 218 that will supplement flow through the flow channel 104 to meet or exceed the threshold flow value. In some embodiments, supplemental propellant 218 flow may be used to deliver an agent 214 to a subject having impaired respiratory function. For example, in some embodiments, supplemental propellant 218 flow may be used to deliver an agent 214 to a subject undergoing an asthma attack.

In some embodiments, operation 1420 includes comparing the at least one assessed flow value to a threshold flow value related to a physical characteristic of the subject (not shown). In some embodiments, system 100 may be used to compare at least one assessed flow value to a threshold flow value related to a physical characteristic of a subject. For example, in some embodiments, a control unit 108 may receive one or more threshold values related to a physical characteristic of a subject using an inhaler. Threshold values may be related to numerous physical characteristics that include, but are not limited to, height, weight, lung volume, respiratory volume, fitness level, and the like. Such threshold values may relate to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with physical characteristics related to subject. In some embodiments, a control unit 108 may compare a threshold value associated with a physical characteristic related to a subject to one or more assessed flow values. For example, in some embodiments, a control unit 108 may compare a threshold value associated with lung volume to an assessed flow volume associated with use of the inhaler by a subject. If the assessed value is less than the threshold value, the control unit 108 may calculate an amount of propellant 218 that will supplement flow through the flow channel 104 to meet or exceed the threshold volume value.

In some embodiments, operation 1420 includes comparing the at least one assessed flow value to a threshold flow value related to lung volume of the subject (not shown). In some embodiments, system 100 may be used to compare at least one assessed flow value to a threshold flow value related to lung volume of a subject. For example, in some embodiments, a control unit 108 may receive one or more threshold values related to the lung volume of a subject using an inhaler. Such threshold values may relate to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with the lung volume of a subject. In some embodiments, a control unit 108 may compare a threshold value associated with the lung volume of a subject to one or more assessed flow values. For example, in some embodiments, a control unit 108 may compare a threshold value associated with lung volume to an assessed flow volume associated with use of the inhaler by a subject. If the assessed value is less than the threshold value, the control unit 108 may calculate an amount of propellant 218 that will supplement flow through the flow channel 104 to meet or exceed the threshold volume value.

In some embodiments, operation 1420 includes comparing the at least one assessed flow value to a threshold flow value related to lung capacity of the subject (not shown). In some embodiments, system 100 may be used to compare at least one assessed flow value to a threshold flow value related to lung capacity of a subject. For example, in some embodiments, a control unit 108 may receive one or more threshold values related to the lung capacity of a subject using an inhaler. Such threshold values may relate to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with the lung capacity of a subject. In some embodiments, a control unit 108 may compare a threshold value associated with the lung capacity of a subject to one or more assessed flow values. For example, in some embodiments, a control unit 108 may compare a threshold value associated with lung capacity to an assessed flow volume associated with use of the inhaler by a subject. If the assessed value is less than the threshold value, the control unit 108 may calculate an amount of propellant 218 that will supplement flow through the flow channel 104 to meet or exceed the threshold capacity value.

In some embodiments, operation 1420 includes comparing the at least one assessed flow value to a threshold flow value related to tidal volume of the subject (not shown). In some embodiments, system 100 may be used to compare at least one assessed flow value to a threshold flow value related to tidal volume of a subject. For example, in some embodiments, a control unit 108 may receive one or more threshold values related to the tidal volume of a subject using an inhaler. Such threshold values may relate to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with the tidal volume of a subject. In some embodiments, a control unit 108 may compare a threshold value associated with the tidal volume of a subject to one or more assessed flow values. For example, in some embodiments, a control unit 108 may compare a threshold value associated with tidal volume to an assessed flow volume associated with use of the inhaler by a subject. If the assessed value is less than the threshold value, the control unit 108 may calculate an amount of propellant 218 that will supplement flow through the flow channel 104 to meet or exceed the threshold tidal volume value.

In some embodiments, operation 1420 includes comparing the at least one assessed flow value to a threshold flow value related to inspiratory capacity of the subject (not shown). In some embodiments, system 100 may be used to compare at least one assessed flow value to a threshold flow value related to inspiratory capacity of a subject. For example, in some embodiments, a control unit 108 may receive one or more threshold values related to the inspiratory capacity of a subject using an inhaler. Such threshold values may relate to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with the inspiratory capacity of a subject. In some embodiments, a control unit 108 may compare a threshold value associated with the inspiratory capacity of a subject to one or more assessed flow values. For example, in some embodiments, a control unit 108 may compare a threshold value associated with inspiratory capacity to an assessed flow volume associated with use of the inhaler by a subject. If the assessed value is less than the threshold value, the control unit 108 may calculate an amount of propellant 218 that will supplement flow through the flow channel 104 to meet or exceed the threshold inspiratory capacity value.

In some embodiments, operation 1420 includes comparing the at least one assessed flow value to a threshold flow value related to vital capacity of the subject (not shown). In some embodiments, system 100 may be used to compare at least one assessed flow value to a threshold flow value related to vital capacity of a subject. For example, in some embodiments, a control unit 108 may receive one or more threshold values related to the vital capacity of a subject using an inhaler. Such threshold values may relate to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with the vital capacity of a subject. In some embodiments, a control unit 108 may compare a threshold value associated with the vital capacity of a subject to one or more assessed flow values. For example, in some embodiments, a control unit 108 may compare a threshold value associated with vital capacity to an assessed flow volume associated with use of the inhaler by a subject. If the assessed value is less than the threshold value, the control unit 108 may calculate an amount of propellant 218 that will supplement flow through the flow channel 104 to meet or exceed the threshold vital capacity value.

In some embodiments, operation 1420 includes comparing the at least one assessed flow value to a threshold flow value related to one or more physiological parameters associated with the subject (not shown). In some embodiments, system 100 may be used to compare at least one assessed flow value to a threshold flow value related to one or more physiological parameters associated with a subject. For example, in some embodiments, a control unit 108 may receive one or more threshold values related to one or more physiological parameters associated with a subject using an inhaler. Examples of physiological parameters include, but are not limited to, breathing rate, rate that an agent 214 is metabolized, base metabolic rate, and the like. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with one or more physiological parameters related to a subject. In some embodiments, a control unit 108 may compare a threshold value associated with one or more physiological parameters related a subject to one or more assessed flow values. For example, in some embodiments, a control unit 108 may compare a threshold value associated with the rate at which an agent 214 is metabolized to an assessed quantity of agent 214 flowing through a flow channel 104 disposed within an inhaler used by a subject. If the assessed quantity of agent 214 is less than the threshold value associated with a desired dosage of agent 214, the control unit 108 may calculate an amount of agent 214 that should be administered to the subject to reach a desired dosage level.

In some embodiments, operation 1420 includes comparing the at least one assessed flow value to a threshold flow value related to a disease state associated with the subject (not shown). In some embodiments, system 100 may be used to compare at least one assessed flow value to a threshold flow value related to a disease state associated with a subject. For example, in some embodiments, a control unit 108 may receive one or more threshold values related to the disease state of a subject using an inhaler. Examples of parameters related to a disease state include, but are not limited to, parameters related to bronchitis, asthma, cystic fibrosis, emphysema, lung cancer, pneumonia, pneumothorax, pulmonary fibrosis, pulmonary hypertension, and the like. Such threshold values may relate to volume of propellant 218 to be delivered to the subject, velocity of propellant 218 to be delivered to the subject, quantity of agent 214 to be delivered to the subject, location within the respiratory tract where agent 214 is to be delivered, and the like. In some embodiments, a threshold flow value related to a disease state may include values related to a level of respiratory function that is impaired due to a disease. For example, in some embodiments, a subject having asthma may exhibit reduced inhalation performance. Accordingly, in some embodiments, an amount of supplemental propellant 218 may be released into the flow channel of an inhaler used by the subject to deliver an agent 214 to the subject. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with the disease state of a subject. In some embodiments, a control unit 108 may compare a threshold value associated with the disease state of a subject to one or more assessed flow values. For example, in some embodiments, a control unit 108 may compare a threshold value associated with a disease state to an assessed flow volume associated with use of the inhaler by a subject. If the assessed value is less than the threshold value, the control unit 108 may calculate an amount of propellant 218 that will supplement flow through the flow channel 104 to meet or exceed the threshold disease state value.

In some embodiments, operation 1420 includes comparing the at least one assessed flow value to a threshold flow value related to delivery of the at least one agent 214 to a location within the respiratory tract of the subject (not shown). In some embodiments, system 100 may be used to compare at least one assessed flow value to a threshold flow value related to delivery of at least one agent 214 to a location within the respiratory tract of a subject. For example, in some embodiments, a control unit 108 may receive one or more threshold values related to delivery of at least one agent to a location within the respiratory tract of a subject using an inhaler. Examples of parameters related to delivery of at least one agent to a location within the respiratory tract of a subject include, but are not limited to, those related to delivery of an agent to the upper respiratory tract, delivery of an agent to the middle respiratory tract, delivery of an agent to the lower respiratory tract, and the like. Such threshold values may relate to volume of propellant 218 to be delivered to the subject, velocity of propellant 218 to be delivered to the subject, quantity of agent 214 to be delivered to the subject, and the like. For example, in some embodiments, threshold parameters may be related to delivery of an agent to the upper respiratory tract of a subject using an inhaler. Accordingly, in some embodiments, a threshold value may relate to a time during the respiratory cycle when an agent 214 is released for delivery to the upper respiratory tract. In some embodiments, a threshold value may relate to a volume of propellant 218 that is released to deliver an agent 214 to the lower respiratory tract. Accordingly, numerous threshold parameters may be related to delivery of an agent 214 to a location in the respiratory tract of a subject. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with delivery of an agent to a location in the respiratory tract of a subject. In some embodiments, such threshold parameters may be correlated with one or more characteristics associated with the subject. Such characteristics may include, but are not limited to, physical characteristics, disease states, and the like. In some embodiments, a control unit 108 may compare a threshold value associated with parameters related to delivery of at least one agent 214 to a location within the respiratory tract of a subject to one or more assessed flow values. For example, in some embodiments, a control unit 108 may compare such a threshold value to an assessed flow volume associated with use of the inhaler by a subject. If the assessed value is less than the threshold value, the control unit 108 may calculate an amount of propellant 218 that will supplement flow through the flow channel 104 to deliver an agent to a location in the respiratory tract of a subject.

In some embodiments, operation 1420 includes comparing the at least one assessed flow value to a threshold flow value related to delivery of the at least one agent 214 to a location within the upper respiratory tract of the subject (not shown). In some embodiments, system 100 may be used to compare at least one assessed flow value to a threshold flow value related to delivery of the at least one agent 214 to a location within the upper respiratory tract of a subject. For example, in some embodiments, a control unit 108 may receive one or more threshold values related to delivery of an agent 214 to a location within the upper respiratory tract of a subject. Such threshold values may relate to volume of propellant 218 to be delivered to the subject, velocity of propellant 218 to be delivered to the subject, quantity of agent 214 to be delivered to the subject, and the like. For example, in some embodiments, a threshold value may relate to a time during the respiratory cycle when an agent 214 is released for delivery to the upper respiratory tract. In some embodiments, a threshold value may relate to a volume of propellant 218 that is released to deliver an agent 214 to the lower respiratory tract. Accordingly, numerous threshold parameters may be related to delivery of an agent 214 to the upper respiratory tract of a subject. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with delivery of an agent to the upper respiratory tract of a subject. In some embodiments, such threshold parameters may be correlated with one or more characteristics associated with the subject. Such characteristics may include, but are not limited to, physical characteristics, disease states, and the like. In some embodiments, a control unit 108 may compare a threshold value associated with parameters related to delivery of at least one agent 214 to the upper respiratory tract of a subject to one or more assessed flow values. For example, in some embodiments, a control unit 108 may compare such a threshold value to an assessed flow volume associated with use of the inhaler by a subject. If the assessed value is less than the threshold value, the control unit 108 may calculate an amount of propellant 218 that will supplement flow through the flow channel 104 to deliver an agent to upper respiratory tract of a subject.

In some embodiments, operation 1420 includes comparing the at least one assessed flow value to a threshold flow value related to delivery of the at least one agent to a location within the middle respiratory tract of the subject (not shown). In some embodiments, system 100 may be used to compare at least one assessed flow value to a threshold flow value related to delivery of the at least one agent to a location within the middle respiratory tract of a subject. For example, in some embodiments, a control unit 108 may receive one or more threshold values related to delivery of an agent 214 to a location within the middle respiratory tract of a subject. Such threshold values may relate to volume of propellant 218 to be delivered to the subject, velocity of propellant 218 to be delivered to the subject, quantity of agent 214 to be delivered to the subject, and the like. For example, in some embodiments, a threshold value may relate to a time during the respiratory cycle when an agent 214 is released for delivery to the middle respiratory tract. In some embodiments, a threshold value may relate to a volume of propellant 218 that is released to deliver an agent 214 to the middle respiratory tract. Accordingly, numerous threshold parameters may be related to delivery of an agent 214 to the middle respiratory tract of a subject. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with delivery of an agent to the middle respiratory tract of a subject. In some embodiments, such threshold parameters may be correlated with one or more characteristics associated with the subject. Such characteristics may include, but are not limited to, physical characteristics, disease states, and the like. In some embodiments, a control unit 108 may compare a threshold value associated with parameters related to delivery of an agent 214 to the middle respiratory tract of a subject to one or more assessed flow values. For example, in some embodiments, a control unit 108 may compare such a threshold value to an assessed flow volume associated with use of the inhaler by a subject. If the assessed value is less than the threshold value, the control unit 108 may calculate an amount of propellant 218 that will supplement flow through the flow channel 104 to deliver an agent 214 to the middle respiratory tract of a subject.

In some embodiments, operation 1420 includes comparing the at least one assessed flow value to a threshold flow value related to delivery of the at least one agent to a location within the lower respiratory tract of the subject (not shown). In some embodiments, system 100 may be used to compare at least one assessed flow value to a threshold flow value related to delivery of the at least one agent to a location within the lower respiratory tract of a subject. For example, in some embodiments, a control unit 108 may receive one or more threshold values related to delivery of an agent 214 to a location within the lower respiratory tract of a subject. Such threshold values may relate to volume of propellant 218 to be delivered to the subject, velocity of propellant 218 to be delivered to the subject, quantity of agent 214 to be delivered to the subject, and the like. For example, in some embodiments, a threshold value may relate to a time during the respiratory cycle when an agent 214 is released for delivery to the lower respiratory tract. In some embodiments, a threshold value may relate to a volume of propellant 218 that is released to deliver an agent 214 to the lower respiratory tract. Accordingly, numerous threshold parameters may be related to delivery of an agent 214 to the lower respiratory tract of a subject. In some embodiments, such threshold values may be input into a user interface 110 that transmits the information to the control unit 108. In some embodiments, a subject may provide a threshold value. In some embodiments, a medical practitioner may provide a threshold value. In some embodiments, a threshold value may be included within a lookup table that is accessed by a control unit 108. In some embodiments, a threshold value may be obtained from a database that includes threshold values that are correlated with delivery of an agent to the lower respiratory tract of a subject. In some embodiments, such threshold parameters may be correlated with one or more characteristics associated with the subject. Such characteristics may include, but are not limited to, physical characteristics, disease states, and the like. In some embodiments, a control unit 108 may compare a threshold value associated with parameters related to delivery of an agent 214 to the lower respiratory tract of a subject to one or more assessed flow values. For example, in some embodiments, a control unit 108 may compare such a threshold value to an assessed flow volume associated with use of the inhaler by a subject. If the assessed value is less than the threshold value, the control unit 108 may calculate an amount of propellant 218 that will supplement flow through the flow channel 104 to deliver an agent 214 to the lower respiratory tract of a subject.

In some embodiments, operation 1420 includes calculating the amount of propellant 218 that will cause the pressure within the at least one flow channel 104 to be between about 5 centimeters of water and 50 centimeters of water (not shown). In some embodiments, system 100 may be used to calculate the amount of propellant 218 that will cause the pressure within at least one flow channel 104 to be between about 5 centimeters of water and 50 centimeters of water. For example, in some embodiments, a control unit 108 may receive one or more assessed values associated with pressure within a flow channel 104 disposed within an inhaler from a pressure sensor 130 that is operably coupled to the flow channel 104. The control unit 108 may then calculate an amount of propellant 218 to be released into the flow channel 104 that will cause the pressure within the flow channel 104 to be between about 5 centimeters of water and 50 centimeters of water. The control unit 108 may then direct one or more actuators 120 to release an amount of propellant 218 from one or more propellant reservoirs 216 that will cause the pressure within the flow channel 104 to be between about 5 centimeters of water and 50 centimeters of water.

In some embodiments, operation 1420 includes calculating the amount of propellant 218 that will cause the pressure within the at least one flow channel 104 to be between about 10 centimeters of water and 40 centimeters of water (not shown). In some embodiments, system 100 may be used to calculate the amount of propellant 218 that will cause the pressure within at least one flow channel 104 to be between about 10 centimeters of water and 40 centimeters of water. For example, in some embodiments, a control unit 108 may receive one or more assessed values associated with pressure within a flow channel 104 disposed within an inhaler from a pressure sensor 130 that is operably coupled to the flow channel 104. The control unit 108 may then calculate an amount of propellant 218 to be released into the flow channel 104 that will cause the pressure within the flow channel 104 to be between about 10 centimeters of water and 40 centimeters of water. The control unit 108 may then direct one or more actuators 120 to release an amount of propellant 218 from one or more propellant reservoirs 216 that will cause the pressure within the flow channel 104 to be between about 10 centimeters of water and 40 centimeters of water.

In some embodiments, operation 1420 includes calculating the amount of propellant 218 that will cause the pressure within the at least one flow channel 104 to be between about 15 centimeters of water and 30 centimeters of water (not shown). In some embodiments, system 100 may be used to calculate the amount of propellant 218 that will cause the pressure within at least one flow channel 104 to be between about 15 centimeters of water and 30 centimeters of water. For example, in some embodiments, a control unit 108 may receive one or more assessed values associated with pressure within a flow channel 104 disposed within an inhaler from a pressure sensor 130 that is operably coupled to the flow channel 104. The control unit 108 may then calculate an amount of propellant 218 to be released into the flow channel 104 that will cause the pressure within the flow channel 104 to be between about 15 centimeters of water and 30 centimeters of water. The control unit 108 may then direct one or more actuators 120 to release an amount of propellant 218 from one or more propellant reservoirs 216 that will cause the pressure within the flow channel 104 to be between about 15 centimeters of water and 30 centimeters of water.

In some embodiments, operation 1420 includes calculating the amount of propellant 218 that will cause the pressure within the at least one flow channel 104 to be between about 20 centimeters of water and 30 centimeters of water (not shown). In some embodiments, system 100 may be used to calculate the amount of propellant 218 that will cause the pressure within at least one flow channel 104 to be between about 20 centimeters of water and 30 centimeters of water.

For example, in some embodiments, a control unit 108 may receive one or more assessed values associated with pressure within a flow channel 104 disposed within an inhaler from a pressure sensor 130 that is operably coupled to the flow channel 104. The control unit 108 may then calculate an amount of propellant 218 to be released into the flow channel 104 that will cause the pressure within the flow channel 104 to be between about 20 centimeters of water and 30 centimeters of water. The control unit 108 may then direct one or more actuators 120 to release an amount of propellant 218 from one or more propellant reservoirs 216 that will cause the pressure within the flow channel 104 to be between about 20 centimeters of water and 30 centimeters of water.

In some embodiments, operation 1420 includes calculating the amount of propellant 218 that will cause the pressure within the at least one flow channel 104 to be about 35 centimeters of water (not shown). In some embodiments, system 100 may be used to calculate the amount of propellant 218 that will cause the pressure within at least one flow channel 104 to be about 35 centimeters of water. For example, in some embodiments, a control unit 108 may receive one or more assessed values associated with pressure within a flow channel 104 disposed within an inhaler from a pressure sensor 130 that is operably coupled to the flow channel 104. The control unit 108 may then calculate an amount of propellant 218 to be released into the flow channel 104 that will cause the pressure within the flow channel 104 to be about 35 centimeters of water. The control unit 108 may then direct one or more actuators 120 to release an amount of propellant 218 from one or more propellant reservoirs 216 that will cause the pressure within the flow channel 104 to be about 35 centimeters of water.

In some embodiments, operation 1420 includes calculating the amount of propellant 218 that will cause a flow rate of between about 5 liters per minute and about 200 liters per minute through the at least one flow channel 104 (not shown). In some embodiments, system 100 may be used to calculate the amount of propellant 218 that will cause a flow rate of between about 5 liters per minute and about 200 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 5 liters per minute and about 200 liters per minute through the flow channel 104. The control unit 108 may then direct one or more actuators 120 to release an amount of propellant 218 from one or more propellant reservoirs 216 that will cause a flow rate of between about 5 liters per minute and about 200 liters per minute through the flow channel 104.

In some embodiments, operation 1420 includes calculating the amount of propellant 218 that will cause a flow rate of between about 30 liters per minute and about 150 liters per minute through the at least one flow channel 104 (not shown). In some embodiments, system 100 may be used to calculate the amount of propellant 218 that will cause a flow rate of between about 30 liters per minute and about 150 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 30 liters per minute and about 150 liters per minute through the flow channel 104. The control unit 108 may then direct one or more actuators 120 to release an amount of propellant 218 from one or more propellant reservoirs 216 that will cause a flow rate of between about 30 liters per minute and about 150 liters per minute through the flow channel 104.

In some embodiments, operation 1420 includes calculating the amount of propellant 218 that will cause a flow rate of between about 50 liters per minute and about 100 liters per minute through the at least one flow channel 104 (not shown). In some embodiments, system 100 may be used to calculate the amount of propellant 218 that will cause a flow rate of between about 50 liters per minute and about 100 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 50 liters per minute and about 100 liters per minute through the flow channel 104. The control unit 108 may then direct one or more actuators 120 to release an amount of propellant 218 from one or more propellant reservoirs 216 that will cause a flow rate of between about 50 liters per minute and about 100 liters per minute through the flow channel 104.

In some embodiments, operation 1420 includes calculating the amount of propellant 218 that will cause a flow rate of between about 20 liters per minute and about 60 liters per minute through the at least one flow channel 104 (not shown). In some embodiments, system 100 may be used to calculate the amount of propellant 218 that will cause a flow rate of between about 20 liters per minute and about 60 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 20 liters per minute and about 60 liters per minute through the flow channel 104. The control unit 108 may then direct one or more actuators 120 to release an amount of propellant 218 from one or more propellant reservoirs 216 that will cause a flow rate of between about 20 liters per minute and about 60 liters per minute through the flow channel 104.

In some embodiments, operation 1420 includes calculating the amount of propellant 218 that will cause a flow rate of between about 30 liters per minute and about 50 liters per minute through the at least one flow channel 104 (not shown). In some embodiments, system 100 may be used to calculate the amount of propellant 218 that will cause a flow rate of between about 30 liters per minute and about 50 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 30 liters per minute and about 50 liters per minute through the flow channel 104. The control unit 108 may then direct one or more actuators 120 to release an amount of propellant 218 from one or more propellant reservoirs 216 that will cause a flow rate of between about 30 liters per minute and about 50 liters per minute through the flow channel 104.

In some embodiments, operation 1420 includes calculating the amount of propellant 218 that will cause a flow rate of between about 50 liters per minute and about 200 liters per minute through the at least one flow channel 104 (not shown). In some embodiments, system 100 may be used to calculate the amount of propellant 218 that will cause a flow rate of between about 50 liters per minute and about 200 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 50 liters per minute and about 200 liters per minute through the flow channel 104. The control unit 108 may then direct one or more actuators 120 to release an amount of propellant 218 from one or more propellant reservoirs 216 that will cause a flow rate of between about 50 liters per minute and about 200 liters per minute through the flow channel 104.

In some embodiments, operation 1420 includes calculating the amount of propellant 218 that will cause a flow rate of between about 75 liters per minute and about 200 liters per minute through the at least one flow channel 104 (not shown). In some embodiments, system 100 may be used to calculate the amount of propellant 218 that will cause a flow rate of between about 75 liters per minute and about 200 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 75 liters per minute and about 200 liters per minute through the flow channel 104. The control unit 108 may then direct one or more actuators 120 to release an amount of propellant 218 from one or more propellant reservoirs 216 that will cause a flow rate of between about 75 liters per minute and about 200 liters per minute through the flow channel 104.

In some embodiments, operation 1420 includes calculating the amount of propellant 218 that will cause a flow rate of between about 100 liters per minute and about 200 liters per minute through the at least one flow channel 104 (not shown). In some embodiments, system 100 may be used to calculate the amount of propellant 218 that will cause a flow rate of between about 100 liters per minute and about 200 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 100 liters per minute and about 200 liters per minute through the flow channel 104. The control unit 108 may then direct one or more actuators 120 to release an amount of propellant 218 from one or more propellant reservoirs 216 that will cause a flow rate of between about 100 liters per minute and about 200 liters per minute through the flow channel 104.

In some embodiments, operation 1420 includes calculating the amount of propellant 218 that will cause a flow rate of between about 125 liters per minute and about 200 liters per minute through the at least one flow channel 104 (not shown). In some embodiments, system 100 may be used to calculate the amount of propellant 218 that will cause a flow rate of between about 125 liters per minute and about 200 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 125 liters per minute and about 200 liters per minute through the flow channel 104. The control unit 108 may then direct one or more actuators 120 to release an amount of propellant 218 from one or more propellant reservoirs 216 that will cause a flow rate of between about 125 liters per minute and about 200 liters per minute through the flow channel 104.

In some embodiments, operation 1420 includes calculating the amount of propellant 218 that will cause a flow rate of between about 150 liters per minute and about 200 liters per minute through the at least one flow channel 104 (not shown). In some embodiments, system 100 may be used to calculate the amount of propellant 218 that will cause a flow rate of between about 150 liters per minute and about 200 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 150 liters per minute and about 200 liters per minute through the flow channel 104. The control unit 108 may then direct one or more actuators 120 to release an amount of propellant 218 from one or more propellant reservoirs 216 that will cause a flow rate of between about 150 liters per minute and about 200 liters per minute through the flow channel 104.

In some embodiments, operation 1420 includes calculating the amount of propellant 218 that will cause a flow rate of between about 175 liters per minute and about 200 liters per minute through the at least one flow channel 104 (not shown). In some embodiments, system 100 may be used to calculate the amount of propellant 218 that will cause a flow rate of between about 175 liters per minute and about 200 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 175 liters per minute and about 200 liters per minute through the flow channel 104. The control unit 108 may then direct one or more actuators 120 to release an amount of propellant 218 from one or more propellant reservoirs 216 that will cause a flow rate of between about 175 liters per minute and about 200 liters per minute through the flow channel 104.

In some embodiments, operation 1420 includes calculating the amount of propellant 218 that will cause a flow rate of between about 50 liters per minute and about 150 liters per minute through the at least one flow channel 104 (not shown). In some embodiments, system 100 may be used to calculate the amount of propellant 218 that will cause a flow rate of between about 50 liters per minute and about 150 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 50 liters per minute and about 150 liters per minute through the flow channel 104. The control unit 108 may then direct one or more actuators 120 to release an amount of propellant 218 from one or more propellant reservoirs 216 that will cause a flow rate of between about 50 liters per minute and about 150 liters per minute through the flow channel 104.

In some embodiments, operation 1420 includes calculating the amount of propellant 218 that will cause a flow rate of between about 60 liters per minute and about 150 liters per minute through the at least one flow channel 104 (not shown). In some embodiments, system 100 may be used to calculate the amount of propellant 218 that will cause a flow rate of between about 60 liters per minute and about 150 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 60 liters per minute and about 150 liters per minute through the flow channel 104. The control unit 108 may then direct one or more actuators 120 to release an amount of propellant 218 from one or more propellant reservoirs 216 that will cause a flow rate of between about 60 liters per minute and about 150 liters per minute through the flow channel 104.

In some embodiments, operation 1420 includes calculating the amount of propellant 218 that will cause a flow rate of between about 60 liters per minute and about 120 liters per minute through the at least one flow channel 104 (not shown). In some embodiments, system 100 may be used to calculate the amount of propellant 218 that will cause a flow rate of between about 60 liters per minute and about 120 liters per minute through at least one flow channel 104. For example, in some embodiments, a control unit 108 may receive one or more assessed values associated with flow rate within a flow channel 104 disposed within an inhaler from a flow sensor 124 that is operably coupled to the flow channel 104. The control unit 108 may then calculate an amount of propellant 218 that will cause a flow rate of between about 60 liters per minute and about 120 liters per minute through the flow channel 104. The control unit 108 may then direct one or more actuators 120 to release an amount of propellant 218 from one or more propellant reservoirs 216 that will cause a flow rate of between about 60 liters per minute and about 120 liters per minute through the flow channel 104.

In some embodiments, operation 1420 includes calculating the amount of propellant 218 that will deliver the at least one agent 214 to a selected location in the respiratory tract of the subject (not shown). In some embodiments, system 100 may be used to calculate the amount of propellant 218 that will deliver at least one agent 214 to a selected location in the respiratory tract of a subject. In some embodiments, a control unit 108 may calculate the amount of propellant 218 that will deliver the at least one agent 214 to a selected location in the respiratory tract of the subject. In some embodiments, a control unit 108 may calculate an amount of propellant 218 based on the total lung capacity of a subject using an inhaler. In some embodiments, a control unit 108 may accept information associated with the total lung volume of a subject and then use the information to calculate an amount of propellant 218 to be dispensed within a flow channel 104 disposed within an inhaler that will deliver an agent 214 to a selected location in the respiratory tract of a subject using the inhaler. For example, in some embodiments, a control unit 108 may calculate an amount of propellant 218 that is equal to half of the total lung volume that will deliver an agent 214 to the middle respiratory tract of the subject. In some embodiments, a control unit 108 may calculate an amount of propellant 218 that is equal to a tenth of the total lung volume that will deliver an agent 214 to the upper respiratory tract of the subject. In some embodiments, a control unit 108 may also determine one or more times during a respiration cycle of a subject using an inhaler that propellant 218 and agent 214 should be released in combination with calculating an amount of propellant 218 that should be released to deliver an agent 214 to a select location within the respiratory tract of a subject.

In some embodiments, operation 1420 includes calculating the amount of propellant 218 that will deliver the at least one agent 214 to the upper respiratory tract of the subject (not shown). In some embodiments, system 100 may be used to calculate the amount of propellant 218 that will deliver at least one agent 214 to the upper respiratory tract of a subject. In some embodiments, a control unit 108 may calculate an amount of propellant 218 that will deliver an agent 214 to the upper respiratory tract of a subject. In some embodiments, a control unit 108 may calculate an amount of propellant 218 based on the total lung capacity of a subject using an inhaler. In some embodiments, a control unit 108 may accept information associated with the total lung volume of a subject and then use the information to calculate an amount of propellant 218 to be dispensed within a flow channel 104 disposed within an inhaler that will deliver an agent 214 to the upper respiratory tract of a subject using the inhaler. For example, in some embodiments, a control unit 108 may calculate an amount of propellant 218 that is equal to a tenth of the total lung volume that will deliver an agent 214 to the upper respiratory tract of the subject. In some embodiments, a control unit 108 may also determine one or more times during a respiration cycle of a subject using an inhaler that propellant 218 and agent 214 should be released in combination with calculating an amount of propellant 218 that should be released to deliver an agent 214 to the upper respiratory tract of a subject.

In some embodiments, operation 1420 includes calculating the amount of propellant that will deliver the at least one agent to the middle respiratory tract of the subject (not shown). In some embodiments, system 100 may be used to calculate the amount of propellant that will deliver at least one agent to the middle respiratory tract of a subject. In some embodiments, a control unit 108 may calculate an amount of propellant 218 that will deliver an agent 214 to the middle respiratory tract of a subject. In some embodiments, a control unit 108 may calculate an amount of propellant 218 based on the total lung capacity of a subject using an inhaler. In some embodiments, a control unit 108 may accept information associated with the total lung volume of a subject and then use the information to calculate an amount of propellant 218 to be dispensed within a flow channel 104 disposed within an inhaler that will deliver an agent 214 to the middle respiratory tract of a subject using the inhaler. For example, in some embodiments, a control unit 108 may calculate an amount of propellant 218 that is equal to half of the total lung volume that will deliver an agent 214 to the middle respiratory tract of the subject. In some embodiments, a control unit 108 may also determine one or more times during a respiration cycle of a subject using an inhaler that propellant 218 and agent 214 should be released in combination with calculating an amount of propellant 218 that should be released to deliver an agent 214 to the middle respiratory tract of a subject.

In some embodiments, operation 1420 includes calculating the amount of propellant 218 that will deliver the at least one agent 214 to the lower respiratory tract of the subject (not shown). In some embodiments, system 100 may be used to calculate the amount of propellant 218 that will deliver at least one agent 214 to the lower respiratory tract of a subject. In some embodiments, a control unit 108 may calculate an amount of propellant 218 that will deliver an agent 214 to the lower respiratory tract of a subject. In some embodiments, a control unit 108 may calculate an amount of propellant 218 based on the total lung capacity of a subject using an inhaler. In some embodiments, a control unit 108 may accept information associated with the total lung volume of a subject and then use the information to calculate an amount of propellant 218 to be dispensed within a flow channel 104 disposed within an inhaler that will deliver an agent 214 to the lower respiratory tract of a subject using the inhaler. For example, in some embodiments, a control unit 108 may calculate an amount of propellant 218 that is equal to eight tenths of the total lung volume that will deliver an agent 214 to the lower respiratory tract of the subject. In some embodiments, a control unit 108 may also determine one or more times during a respiration cycle of a subject using an inhaler that propellant 218 and agent 214 should be released in combination with calculating an amount of propellant 218 that should be released to deliver an agent 214 to the lower respiratory tract of a subject.

In some embodiments, operation 1420 includes calculating the amount of propellant 218 that will deliver the at least one agent 214 to deep lung tissue in the respiratory tract of the subject (not shown). In some embodiments, system 100 may be used to calculate the amount of propellant 218 that will deliver at least one agent 214 to deep lung tissue in the respiratory tract of a subject. In some embodiments, a control unit 108 may calculate an amount of propellant 218 that will deliver an agent 214 to deep lung tissue in the respiratory tract of a subject. In some embodiments, a control unit 108 may calculate an amount of propellant 218 based on the total lung capacity of a subject using an inhaler. In some embodiments, a control unit 108 may accept information associated with the total lung volume of a subject and then use the information to calculate an amount of propellant 218 to be dispensed within a flow channel 104 disposed within an inhaler that will deliver an agent 214 to deep lung tissue of a subject using the inhaler. For example, in some embodiments, a control unit 108 may calculate an amount of propellant 218 that is equal to the total lung volume that will deliver an agent 214 to deep lung tissue of the subject. In some embodiments, a control unit 108 may also determine one or more times during a respiration cycle of a subject using an inhaler that propellant 218 and agent 214 should be released in combination with calculating an amount of propellant 218 that should be released to deliver an agent 214 to deep lung tissue of a subject. For example, in some embodiments, a control unit may direct one or more actuators to facilitate release of agent 214 from an agent reservoir 212 and propellant 218 from a propellant reservoir 216 at an early stage of an inhalation cycle by a subject using an inhaler to deliver the agent 214 to deep lung tissue in the subject.

In some embodiments, operation 1430 includes dispensing the at least one agent 214 from at least one agent reservoir 212 that contains an aerosolized agent 214 (not shown). In some embodiments, system 100 may be used to dispense an agent 214 from an agent reservoir 212 that contains an aerosolized agent 214. For example, in some embodiments, a control unit 108 may direct one or more actuators 120 to facilitate at least partial release of an aerosolized agent 214 from an aerosol canister that includes the aerosolized agent 214 into a flow channel 104 disposed within an inhaler. In some embodiments, an aerosol canister content release mechanism 270 may be used to facilitate release of an aerosolized agent 214 from an aerosol canister.

In some embodiments, operation 1430 includes dispensing the at least one agent 214 from at least one agent reservoir 212 that contains a dry powdered agent 214 (not shown). In some embodiments, system 100 may be used to dispensing the at least one agent 214 from at least one agent reservoir 212 that contains a dry powdered agent 214. In some embodiments, a control unit 108 may direct one or more actuators 120 to facilitate at least partial release of an agent 214 from an agent reservoir 212 that contains a dry powdered agent 214. For example, in some embodiments, an agent reservoir 212 may include a conveyor with at least one conveying drive to advance a blister strip that includes a plurality of blister packs that are filled with a powdered agent 214. In some embodiments, a control unit 108 may direct the operation of the conveying drive to advance the blister strip. In some embodiments, a control unit 108 may direct the operation of a blister pack puncture mechanism 272 to puncture a blister pack and propel a dry powdered agent 214 into a flow channel 104 disposed within an inhaler.

In some embodiments, operation 1430 includes dispensing the amount of propellant 218 that will cause the flow through the at least one flow channel 104 to meet or exceed the threshold flow value from a propellant reservoir 216 (not shown). In some embodiments, system 100 may be used to dispense the amount of propellant 218 that will cause flow through at least one flow channel 104 to meet or exceed a threshold flow value from a propellant reservoir 216. For example, in some embodiments, a control unit 108 may compare a threshold value associated with flow through a flow channel 104 disposed within an inhaler to an assessed flow value associated with use of the inhaler by a subject. If the assessed value is less than the threshold value, the control unit 108 may calculate an amount of propellant 218 that will supplement flow through the flow channel 104 to meet or exceed the threshold flow value. The control unit 108 may then direct one or more actuators 120 to facilitate at least partial release of propellant 218 from one or more propellant reservoirs 216 to cause propellant 218 flow through a flow channel 104 to meet or exceed the threshold value associated with flow.

In some embodiments, operation 1430 includes dispensing the propellant 218 from a propellant reservoir 216 operably coupled to a controllable regulator 260 (not shown). In some embodiments, system 100 may be used to dispense propellant 218 from a propellant reservoir 216 operably coupled to a controllable regulator 260. In some embodiments, a control unit 108 may direct the operation of a regulator 260 that is operably coupled to a propellant reservoir 216 to at least partially release propellant 218 from the propellant reservoir 216.

In some embodiments, operation 1430 includes dispensing one or more chlorofluorocarbons (not shown). In some embodiments, system 100 may be used to dispense one or more chlorofluorocarbons. In some embodiments, a control unit 108 may direct the operation of an actuator 120 that is operably coupled to a propellant reservoir 216 that includes one or more chlorofluorocarbons to at least partially release the one or more chlorofluorocarbons from the propellant reservoir 216.

In some embodiments, operation 1430 includes dispensing one or more hydrofluoroalkanes (not shown). In some embodiments, system 100 may be used to dispense one or more hydrofluoroalkanes. In some embodiments, a control unit 108 may direct the operation of an actuator 120 that is operably coupled to a propellant reservoir 216 that includes one or more hydrofluoroalkanes to at least partially release the one or more hydrofluoroalkanes from the propellant reservoir 216.

In some embodiments, operation 1430 includes dispensing compressed gas (not shown). In some embodiments, system 100 may be used to dispense compressed gas. In some embodiments, a control unit 108 may direct the operation of an actuator 120 that is operably coupled to a propellant reservoir 216 that includes compressed gas to at least partially release the compressed gas from the propellant reservoir 216.

In some embodiments, operation 1430 includes dispensing the propellant 218 with a compressor (not shown). In some embodiments, system 100 may be used to dispense propellant 218 with a compressor. In some embodiments, a control unit 108 may direct the operation of a compressor that is operably coupled to a flow channel disposed within an inhaler to deliver compressed gas into the flow channel 104.

In some embodiments, operation 1430 includes dispensing the at least one agent 214 to a preselected location within the respiratory tract of the subject (not shown). In some embodiments, system 100 may be used to dispense at least one agent 214 to a preselected location within the respiratory tract of a subject. In some embodiments, a control unit 108 may calculate an amount of propellant 218 that should be released from a propellant reservoir 216 to delivery an agent 214 to a preselected location within the respiratory tract of a subject using an inhaler. In some embodiments, a control unit 108 may calculate an amount of propellant 218 based on the total lung volume of the subject. For example, in some embodiments, a control unit 108 may calculate an amount of propellant 218 that is equal to one tenth of the total lung capacity of a subject using an inhaler and then direct one or more actuators 120 to facilitate release of the calculated amount of propellant 218 from one or more propellant reservoirs 216 to deliver an agent 214 to the upper respiratory tract of the subject. In some embodiments, a control unit 108 may calculate an amount of propellant 218 that is equal to one half of the total lung capacity of a subject using an inhaler and then direct one or more actuators 120 to facilitate release of the calculated amount of propellant 218 from one or more propellant reservoirs 216 to deliver an agent 214 to the middle respiratory tract of the subject. In some embodiments, a control unit 108 may direct one or more actuators 120 to facilitate release of an agent 214 from one or more agent reservoirs 212 and propellant 218 from one or more propellant reservoirs 216 at a selected time during a respiration cycle of a subject using an inhaler to deliver agent 214 to a preselected location within the respiratory tract of a subject. For example, in some embodiments, a control unit 108 may direct one or more actuators 120 to facilitate release of an agent 214 during an early stage of an inhalation cycle of a subject using an inhaler to deliver the agent 214 to the lower respiratory tract of the subject. In some embodiments, a control unit 108 may direct one or more actuators 120 to facilitate release of an agent 214 during a late stage of an inhalation cycle of a subject using an inhaler to deliver the agent 214 to the upper respiratory tract of the subject. Accordingly, in some embodiments, a control unit 108 may facilitate release of agent 214 and propellant 218 in a coordinated fashion to deliver an agent 214 to a preselected location in the respiratory tract of a subject using an inhaler.

In some embodiments, operation 1430 includes dispensing the at least one agent 214 to the upper respiratory tract of the subject (not shown). In some embodiments, system 100 may be used to dispense at least one agent 214 to the upper respiratory tract of a subject. In some embodiments, a control unit 108 may calculate an amount of propellant 218 that should be released from a propellant reservoir 216 to delivery an agent 214 to the upper respiratory tract of a subject using an inhaler. In some embodiments, a control unit 108 may calculate an amount of propellant 218 based on the total lung volume of the subject. For example, in some embodiments, a control unit 108 may calculate an amount of propellant 218 that is equal to one tenth of the total lung capacity of a subject using an inhaler and then direct one or more actuators 120 to facilitate release of the calculated amount of propellant 218 from one or more propellant reservoirs 216 to deliver an agent 214 to the upper respiratory tract of the subject. In some embodiments, a control unit 108 may direct one or more actuators 120 to facilitate release of an agent 214 from one or more agent reservoirs 212 and propellant 218 from one or more propellant reservoirs 216 at a selected time during a respiration cycle of a subject using an inhaler to deliver agent 214 to a preselected location within the respiratory tract of a subject. For example, in some embodiments, a control unit 108 may direct one or more actuators 120 to facilitate release of an agent 214 during a late stage of an inhalation cycle of a subject using an inhaler to deliver the agent 214 to the upper respiratory tract of the subject. Accordingly, in some embodiments, a control unit 108 may facilitate release of agent 214 and propellant 218 in a coordinated fashion to deliver an agent 214 to the upper respiratory tract of a subject using an inhaler.

In some embodiments, operation 1430 includes dispensing the at least one agent 214 to the middle respiratory tract of the subject (not shown). In some embodiments, system 100 may be used to dispense at least one agent to the middle respiratory tract of a subject. In some embodiments, a control unit 108 may calculate an amount of propellant 218 that should be released from a propellant reservoir 216 to delivery an agent 214 to the middle respiratory tract of a subject using an inhaler. In some embodiments, a control unit 108 may calculate an amount of propellant 218 based on the total lung volume of the subject. For example, in some embodiments, a control unit 108 may calculate an amount of propellant 218 that is equal to one half of the total lung capacity of a subject using an inhaler and then direct one or more actuators 120 to facilitate release of the calculated amount of propellant 218 from one or more propellant reservoirs 216 to deliver an agent 214 to the middle respiratory tract of the subject. In some embodiments, a control unit 108 may direct one or more actuators 120 to facilitate release of an agent 214 from one or more agent reservoirs 212 and propellant 218 from one or more propellant reservoirs 216 at a selected time during a respiration cycle of a subject using an inhaler to deliver agent 214 to the middle respiratory tract of a subject. For example, in some embodiments, a control unit 108 may direct one or more actuators 120 to facilitate release of an agent 214 during a middle stage of an inhalation cycle of a subject using an inhaler to deliver the agent 214 to the middle respiratory tract of the subject. Accordingly, in some embodiments, a control unit 108 may facilitate release of agent 214 and propellant 218 in a coordinated fashion to deliver an agent 214 to the middle respiratory tract of a subject using an inhaler.

In some embodiments, operation 1430 includes dispensing the at least one agent 214 to the lower respiratory tract of the subject (not shown). In some embodiments, system 100 may be used to dispense at least one agent 214 to the lower respiratory tract of a subject. In some embodiments, a control unit 108 may calculate an amount of propellant 218 that should be released from a propellant reservoir 216 to delivery an agent 214 to the lower respiratory tract of a subject using an inhaler. In some embodiments, a control unit 108 may calculate an amount of propellant 218 based on the total lung volume of the subject. For example, in some embodiments, a control unit 108 may calculate an amount of propellant 218 that is equal to eight tenths of the total lung capacity of a subject using an inhaler and then direct one or more actuators 120 to facilitate release of the calculated amount of propellant 218 from one or more propellant reservoirs 216 to deliver an agent 214 to the lower respiratory tract of the subject. In some embodiments, a control unit 108 may direct one or more actuators 120 to facilitate release of an agent 214 from one or more agent reservoirs 212 and propellant 218 from one or more propellant reservoirs 216 at a selected time during a respiration cycle of a subject using an inhaler to deliver agent 214 to the lower respiratory tract of a subject. For example, in some embodiments, a control unit 108 may direct one or more actuators 120 to facilitate release of an agent 214 during an early stage of an inhalation cycle of a subject using an inhaler to deliver the agent 214 to the lower respiratory tract of the subject. Accordingly, in some embodiments, a control unit 108 may facilitate release of agent 214 and propellant 218 in a coordinated fashion to deliver an agent 214 to the lower respiratory tract of a subject using an inhaler.

In some embodiments, operation 1430 includes dispensing the at least one agent 214 at the beginning of an inhalation cycle (not shown). In some embodiments, system 100 may be used to dispense at least one agent 214 at the beginning of an inhalation cycle. For example, in some embodiments, a control unit 108 may direct one or more actuators 120 to facilitate at least partial release of agent 214 from one or more agent reservoirs 212 at the beginning of an inhalation cycle of a subject using an inhaler.

In some embodiments, operation 1430 includes dispensing the at least one agent 214 in the middle of an inhalation cycle (not shown). In some embodiments, system 100 may be used to dispense at least one agent 214 in the middle of an inhalation cycle. For example, in some embodiments, a control unit 108 may direct one or more actuators 120 to facilitate at least partial release of agent 214 from one or more agent reservoirs 212 in the middle of an inhalation cycle of a subject using an inhaler.

In some embodiments, operation 1430 includes dispensing the at least one agent 214 at the end of an inhalation cycle (not shown). In some embodiments, system 100 may be used to dispense at least one agent 214 at the end of an inhalation cycle. For example, in some embodiments, a control unit 108 may direct one or more actuators 120 to facilitate at least partial release of agent 214 from one or more agent reservoirs 212 at the end of an inhalation cycle of a subject using an inhaler.

In some embodiments, operation 1430 includes dispensing the at least one agent 214 until a preselected quantity of the at least one agent 214 is dispensed (not shown). In some embodiments, system 100 may be used to dispense at least one agent 214 until a preselected quantity of agent 214 is dispensed. In some embodiments, a control unit 108 may receive one or more signals 112 that include information associated with a quantity of agent 214 flowing through a flow channel 104 disposed within an inhaler used by a subject from one or more sensors 114 that are operably coupled with the flow channel 104. The control unit 108 may then calculate an additional quantity of agent 214 that needs to be dispensed to the subject to reach a desired dosage. The control unit 108 may then direct one or more actuators 120 to facilitate at least partial release of agent 214 from one or more agent reservoirs 212 to dispense the agent 214 to reach the desired dosage.

In some embodiments, operation 1430 includes storing one or more parameters associated with the dispensing (not shown). In some embodiments, system 100 may be used to storing one or more parameters associated with the dispensing. In some embodiments, a control unit 108 may store information associated with one or more parameters associated with dispensing one or more agents 214. In some embodiments, such information may be stored in control memory 204.

In some embodiments, operation 1430 includes modifying the dispensing of at least one agent 214 during a later respiratory cycle in response to one or more stored parameters associated with the dispensing of at least one agent 214 during an earlier respiratory cycle (not shown). In some embodiments, system 100 may be used to modify the dispensing of an agent 214 during a later respiratory cycle in response to one or more stored parameters associated with dispensing of the agent 214 during an earlier respiratory cycle. In some embodiments, a control unit 108 may be configured to modify dispensing of an agent 214 during a later respiratory cycle in response to one or more stored parameters associated with dispensing the agent 214 during an earlier respiratory cycle. For example, in some embodiments, a control unit 108 may direct one or more actuators 120 to facilitate at least partial release of agent 214 from one or more agent reservoirs 212 during an early stage of a respiration cycle of a subject using an inhaler. The control unit 108 may then direct one or more actuators 120 to facilitate at least partial release of agent 214 from one or more agent reservoirs 212 during a middle stage of a respiration cycle of a subject using an inhaler. The control unit 108 may then direct one or more actuators 120 to facilitate at least partial release of agent 214 from one or more agent reservoirs 212 during a late stage of a respiration cycle of a subject using an inhaler. Accordingly, numerous parameters associated with dispensing an agent 214 may be modified in response to one or more stored parameters.

Figure 15:
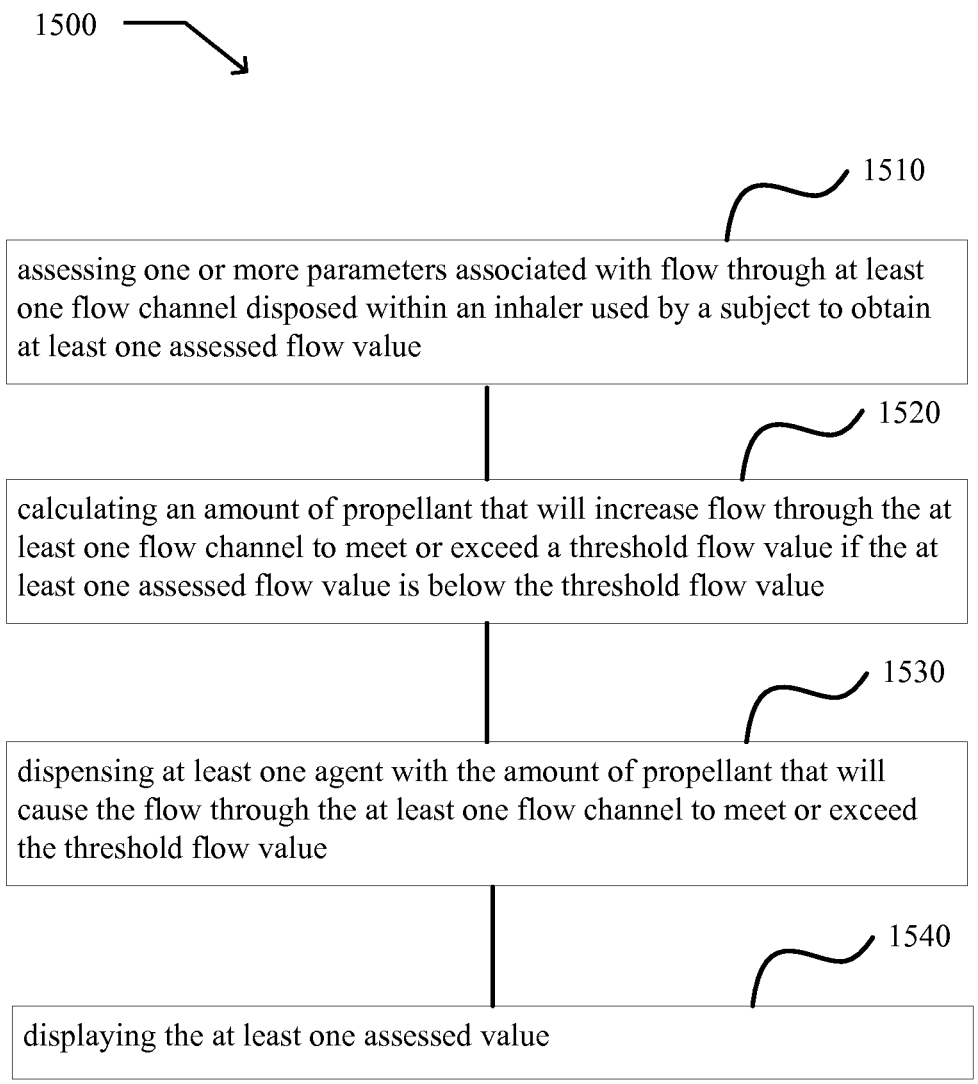
FIG. 15 illustrates an example operational flow 1500 in which embodiments may be implemented.

FIG. 15 illustrates operational flow 1500 that includes operation 1510 that includes assessing one or more parameters associated with flow through at least one flow channel disposed within an inhaler used by a subject to obtain at least one assessed flow value, operation 1520 that includes calculating an amount of propellant that will increase flow through the at least one flow channel to meet or exceed a threshold flow value if the at least one assessed flow value is below the threshold flow value, operation 1530 that includes dispensing at least one agent with the amount of propellant that will cause the flow through the at least one flow channel to meet or exceed the threshold flow value, and operation 1540 that includes displaying the at least one assessed value. Operations 1510, 1520, and 1530 correspond to operations 1410, 1420, and 1430 as previously described with reference to FIG. 14.

In FIG. 15 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1540 includes displaying the at least one assessed value. In some embodiments, system 100 may be used to display at least one assessed value. In some embodiments, a sensor 114 may assess one or more values and then transmit one or more signals 112 that include an assessed value to a user interface 110 that displays the assessed value. In some embodiments, a sensor 114 may assess one or more values and then transmit one or more signals 112 that include an assessed value to a control unit 108 that transmits the information to a user interface 110 that displays the assessed value. In some embodiments, a flow sensor 124 may assess one or more flow values and then transmit one or more signals 112 that include an assessed flow value to a flow indicator 116 that displays the assessed flow value. Accordingly, an assessed value may be displayed in numerous ways.

In some embodiments, operation 1540 includes displaying at least one measured flow value (not shown). In some embodiments, system 100 may be used to display at least one measured flow value. In some embodiments, a flow sensor 124 may assess one or more flow values and then transmit one or more signals 112 that include an assessed flow value to a flow indicator 116 that displays the assessed flow value. In some embodiments, a flow sensor 124 may assess one or more flow values and then transmit one or more signals 112 that include an assessed flow value to a user interface 110 that displays the assessed flow value. Accordingly, an assessed value may be displayed in numerous ways.

In some embodiments, operation 1540 includes displaying at least one comparison of the at least one assessed flow value to the threshold flow value (not shown). In some embodiments, system 100 may be used to display at least one comparison of at least one assessed flow value to a threshold flow value. In some embodiments, a control unit 108 may receive one or more signals 112 that include information associated with flow through one or more flow channels 104 disposed within an inhaler from a flow sensor 124 that is operably coupled to the flow channel 104. The control unit 108 may compare the assessed flow value to a threshold flow value. The control unit 108 may then transmit information associated with the comparison to a user interface 110 that displays the comparison. In some embodiments, the control unit 108 may transmit information associated with the comparison to a flow indicator 116 that displays the comparison.

In some embodiments, operation 1540 includes displaying at least one ratio of the at least one assessed flow value to the threshold flow value (not shown). In some embodiments, system 100 may be used to displaying at least one ratio of the at least one assessed flow value to the threshold flow value. In some embodiments, a control unit 108 may receive one or more signals 112 that include information associated with flow through one or more flow channels 104 disposed within an inhaler from a flow sensor 124 that is operably coupled to the flow channel 104. The control unit 108 may determine at least one ratio of the assessed flow value to a threshold flow value. The control unit 108 may then transmit information associated with the ratio to a user interface 110 that displays the comparison. In some embodiments, the control unit 108 may transmit information associated with the ratio to a flow indicator 116 that displays the comparison.

Figure 16:
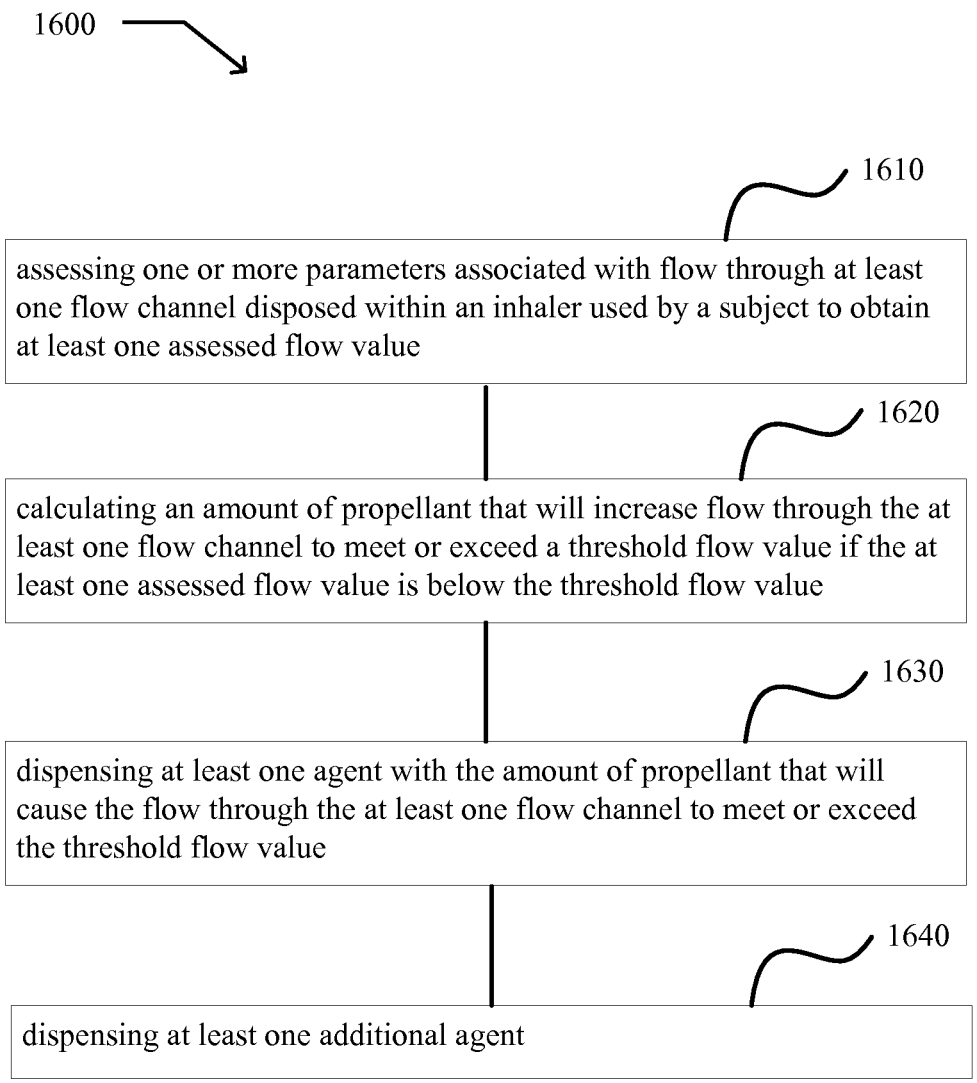
FIG. 16 illustrates an example operational flow 1600 in which embodiments may be implemented.

FIG. 16 illustrates operational flow 1600 that includes operation 1610 that includes assessing one or more parameters associated with flow through at least one flow channel 104 disposed within an inhaler used by a subject to obtain at least one assessed flow value, operation 1620 that includes calculating an amount of propellant 218 that will increase flow through the at least one flow channel 104 to meet or exceed a threshold flow value if the at least one assessed flow value is below the threshold flow value, operation 1630 that includes dispensing at least one agent 214 with the amount of propellant 218 that will cause the flow through the at least one flow channel 104 to meet or exceed the threshold flow value, and operation 1640 that includes dispensing at least one additional agent 214. Operations 1610, 1620, and 1630 correspond to operations 1410, 1420, and 1430 as previously described with reference to FIG. 14.

In FIG. 16 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1640 includes dispensing at least one additional agent 214. In some embodiments, system 100 may be used to dispense at least one additional agent 214. In some embodiments, a control unit 108 may direct an actuator 120 to facilitate at least partial release of an agent 214 from a first agent reservoir 212 into a flow channel 104 disposed within an inhaler and then direct an actuator 120 to facilitate at least partial release of a second agent 214 from a second agent reservoir 212 into the flow channel 104 disposed within the inhaler.

In some embodiments, operation 1640 includes dispensing at least one vasodilator (not shown). In some embodiments, system 100 may be used to dispense at least one vasodilator. In some embodiments, a control unit 108 may direct an actuator 120 to facilitate at least partial release of a vasodilator from an agent reservoir 212 into a flow channel 104 disposed within an inhaler. Numerous types of vasodilators may be dispensed. Examples of such vasodilators include, but are not limited to, nitric oxide, prostacyclin, phosphodiesterase inhibitors, endothelin and thromboxane antagonists, adrenomedullin, sodium nitrorusside, nitroglycerin, and the like (see e.g., *Remingtion: The Science and Practice of Pharmacy*, Lippincott, Williams & Wilkins, 20th edition, Baltimore, Md., USA (2000), *Physicians' Desk Reference,* Thomson PDR, 58th edition, Montvale, N.J. (2004); *Merck Index,* Merck and Co., 13th edition., Whitehouse Station, N.J. (2001); which are hereby incorporated by reference).

In some embodiments, operation 1640 includes dispensing at least one anti-inflammatory agent (not shown). In some embodiments, system 100 may be used to dispense at least one anti-inflammatory agent. In some embodiments, a control unit 108 may direct an actuator 120 to facilitate at least partial release of an anti-inflammatory agent from an agent reservoir 212 into a flow channel 104 disposed within an inhaler. Numerous types of an anti-inflammatory agent may be dispensed. Examples of such anti-inflammatory agents include, but are not limited to, steroids, corticosteroids, mast cell stabilizers, leukotriene modifiers, immunomodulators, and the like (see e.g., *Remington: The Science and Practice of Pharmacy,* Lippincott, Williams & Wilkins, 20th edition, Baltimore, Md., USA (2000), *Physicians' Desk Reference,* Thomson PDR, 58th edition, Montvale, N.J. (2004); *Merck Index,* Merck and Co., 13th edition., Whitehouse Station, N.J. (2001); which are hereby incorporated by reference).

In some embodiments, a system includes a computer program for executing a computer process on a computing device that may be used to control an inhaler. In some embodiments, such a system is provided that includes a non-transitory signal-bearing medium bearing one or more instructions that, when executed by one or more processing components, direct performance of operations that include at least: assessing one or more parameters associated with flow through at least one flow channel disposed within an inhaler used by a subject to obtain at least one assessed flow value; calculating an amount of propellant that will increase flow through the at least one flow channel to meet or exceed a threshold flow value if the at least one assessed flow value is below the threshold flow value; and dispensing at least one agent with the amount of propellant that will cause the flow through the at least one flow channel to meet or exceed the threshold flow value. In some embodiments, the non-transitory signal-bearing medium may further include one or more instructions that direct performance of an operation that includes at least displaying the at least one assessed value. In some embodiments, the non-transitory signal-bearing medium may further include one or more instructions that direct performance of an operation that includes at least dispensing at least one additional agent. The one or more instructions may be, for example, computer executable and/or logic-implemented instructions. In some embodiments, the non-transitory signal-bearing medium may include a computer-readable medium. In some embodiments, the non-transitory signal-bearing medium may include a recordable medium. In some embodiments, the non-transitory signal-bearing medium may include a communications medium.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof, limited to patentable subject matter under 35 U.S.C. 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. 101, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof, limited to patentable subject matter under 35 U.S.C. 101; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Although user 116 is described herein as a single individual, those skilled in the art will appreciate that user 116 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   circuitry configured to assess one or more parameters associated with flow through at least one flow channel disposed within an inhaler used by a subject to obtain at least one assessed flow value;
   circuitry configured to calculate an amount of propellant that will increase flow through the at least one flow channel to meet or exceed a threshold flow value if the at least one assessed flow value is below the threshold flow value including at least circuitry configured to compare the at least one assessed flow value to a particular threshold flow value related to the subject; and
   circuitry configured to dispense at least one agent with the amount of propellant that will cause the flow through the at least one flow channel to meet or exceed the particular threshold flow value.

2. The system of claim 1, wherein the circuitry configured to assess one or more parameters associated with flow through at least one flow channel disposed within an inhaler used by a subject to obtain at least one assessed flow value comprises:
   circuitry configured to assess a volume of gas flowing through the at least one flow channel.

3. The system of claim 1, wherein the circuitry configured to assess one or more parameters associated with flow through at least one flow channel disposed within an inhaler used by a subject to obtain at least one assessed flow value comprises:
   circuitry configured to assess gas pressure within the at least one flow channel.

4. The system of claim 1, wherein the circuitry configured to assess one or more parameters associated with flow through at least one flow channel disposed within an inhaler used by a subject to obtain at least one assessed flow value comprises:
   circuitry configured to assess a quantity of the at least one agent flowing through the at least one flow channel.

5. The system of claim 1, wherein the circuitry configured to dispense at least one agent with the amount of propellant that will cause the flow through the at least one flow channel to meet or exceed the threshold flow value comprises:
   circuitry configured to transmit one or more signals that direct one or more actuators to facilitate release of the amount of propellant from one or more propellant reservoirs into the at least one flow channel that increases flow to meet or exceed the threshold flow value.

6. The system of claim 1, wherein the circuitry configured to dispense at least one agent with the amount of propellant that will cause the flow through the at least one flow channel to meet or exceed the threshold flow value comprises:
   circuitry configured to dispense the propellant through use of a controllable regulator.

7. The system of claim 1, wherein the circuitry configured to dispense at least one agent with the amount of propellant that will cause the flow through the at least one flow channel to meet or exceed the threshold flow value comprises:
   circuitry configured to dispense the at least one agent during a stage of a respiratory cycle selected to deliver the at least one agent to a preselected location within the respiratory tract of the subject.

8. The system of claim 1, wherein the circuitry configured to dispense at least one agent with the amount of propellant that will cause the flow through the at least one flow channel to meet or exceed the threshold flow value comprises:
   circuitry configured to dispense the at least one agent to the subject at the beginning of an inhalation cycle.

9. The system of claim 1, wherein the circuitry configured to dispense at least one agent with the amount of propellant that will cause the flow through the at least one flow channel to meet or exceed the threshold flow value comprises:
   circuitry configured to dispense the at least one agent until a preselected quantity of the at least one agent is dispensed.

10. The system of claim 1, further comprising:
    circuitry configured to display the at least one assessed value.

11. A system comprising:
    a non-transitory signal-bearing medium bearing one or more instructions that, when executed by one or more processing components, direct performance of operations that include at least:
        assessing one or more parameters associated with flow through at least one flow channel disposed within an inhaler used by a subject to obtain at least one assessed flow value;
        calculating an amount of propellant that will increase flow through the at least one flow channel to meet or exceed a threshold flow value if the at least one assessed flow value is below the threshold flow value; and
        dispensing at least one agent with the amount of propellant that will cause the flow through the at least one flow channel to meet or exceed the threshold flow value.

12. The system of claim 11, further comprising:
    one or more instructions that direct performance of an operation that includes at least displaying the at least one assessed value.

13. The system of claim 11, further comprising:
one or more instructions that direct performance of an operation that includes at least dispensing at least one additional agent.

14. A system comprising:
at least one control unit operatively configured to control a flow propellant from a propellant reservoir, the at least one control unit including at least one processor and a memory bearing one or more instructions that, when executed by the at least one processor, configure the at least one control unit to perform operations including at least:
assess one or more parameters associated with flow through at least one flow channel disposed within an inhaler used by a subject to obtain at least one assessed flow value;
calculate an amount of propellant that will increase flow through the at least one flow channel to meet or exceed a threshold flow value if the at least one assessed flow value is below the threshold flow value including at least circuitry configured to compare the at least one assessed flow value to a particular threshold flow value related to the subject; and
dispense at least one agent with the amount of propellant that will cause the flow through the at least one flow channel to meet or exceed the particular threshold flow value.

15. The system of claim 14 further comprising:
the inhaler including at least:
a housing having the at least one flow channel disposed therein;
at least one port disposed in the housing operably coupled to the at least one flow channel and configured to provide fluid communication between at least one agent reservoir and at least one propellant reservoir and the at least one flow channel;
at least one sensor operably coupled with the at least one flow channel;
at least one actuator configured to facilitate at least partial release from either or both of the at least one agent reservoir and the at least one propellant reservoir when the at least one agent reservoir and the at least one propellant reservoir are operably coupled to the at least one port; and
wherein the at least one control unit is configured to receive information from the at least one sensor and direct the at least one actuator to facilitate at least partial release from either or both of the at least one agent reservoir and the at least one propellant reservoir.

16. The system of claim 15 wherein the at least one port disposed in the housing operably coupled to the at least one flow channel and configured to provide fluid communication between at least one agent reservoir and at least one propellant reservoir and the at least one flow channel includes:
at least one port configured to receive at least one agent reservoir including an aerosol canister that includes a canister body and a valve stem that extends from the canister body.

17. The system of claim 15 wherein the at least one port disposed in the housing operably coupled to the at least one flow channel and configured to provide fluid communication between at least one agent reservoir and at least one propellant reservoir and the at least one flow channel includes:
at least one controllable regulator.

18. The system of claim 15 wherein the at least one sensor operably coupled with the at least one flow channel includes:
at least one flow sensor.

19. The system of claim 15 wherein the at least one sensor operably coupled with the at least one flow channel includes:
at least one pressure sensor.

20. The system of claim 15 wherein the at least one sensor operably coupled with the at least one flow channel includes:
at least one sensor configured to assess one or more values associated with one or more respiration parameters.

21. The system of claim 15 wherein the at least one sensor operably coupled with the at least one flow channel includes:
at least one sensor configured to assess flow of at least one agent through the at least one flow channel.

22. The system of claim 15 wherein the at least one actuator configured to facilitate at least partial release from either or both of the at least one agent reservoir and the at least one propellant reservoir when the at least one agent reservoir and the at least one propellant reservoir are operably coupled to the at least one port includes:
at least one aerosol canister content release mechanism.

23. The system of claim 15 wherein the at least one actuator configured to facilitate at least partial release from either or both of the at least one agent reservoir and the at least one propellant reservoir when the at least one agent reservoir and the at least one propellant reservoir are operably coupled to the at least one port includes:
at least one propellant control valve.

24. The system of claim 15 wherein the at least one control unit configured to receive information from the at least one sensor and direct the at least one actuator to facilitate at least partial release from either or both of the at least one agent reservoir and the at least one propellant reservoir includes:
at least one control unit in operable communication with at least one sensor configured to assess one or more values associated with one or more respiration parameters.

25. The system of claim 15 wherein the at least one control unit configured to receive information from the at least one sensor and direct the at least one actuator to facilitate at least partial release from either or both of the at least one agent reservoir and the at least one propellant reservoir includes:
at least one control unit in operable communication with at least one flow sensor.

26. The system of claim 15 wherein the inhaler further includes:
at least one agent reservoir operably coupled to the at least one port.

27. The system of claim 15 wherein the inhaler includes:
at least one propellant reservoir operably coupled to the at least one port.

28. The system of claim 27 wherein the at least one propellant reservoir operably coupled to the at least one port comprises:
a compressed gas canister.

29. The system of claim 15 wherein the inhaler includes:
at least one dose counter.

30. The system of claim 15 wherein the inhaler includes:
at least one flow indicator.

31. The system of claim 30 wherein the at least one flow indicator comprise:
at least one flow indicator configured to indicate one or more values associated with one or more respiration parameters.

32. The system of claim 15 wherein the inhaler includes:
at least one controllable flow valve operably coupled with the at least one flow channel.

33. The system of claim 32 wherein the at least one controllable flow valve operably coupled with the at least one flow channel comprises:
    at least one controllable valve configured to substantially block flow through a distal opening associated with the at least one flow channel in response to activation of the at least one actuator.

\* \* \* \* \*